United States Patent
Seitz et al.

(10) Patent No.: US 6,448,201 B1
(45) Date of Patent: Sep. 10, 2002

(54) BENZOYLCYCLOHEXANEDIONES AND BENZOYLPYRAZOLES, THEIR PREPARATION, AND THEIR USE AS HERBICIDES AND PLANT GROWTH REGULATORS

(75) Inventors: Thomas Seitz, Viernheim; Lothar Willms, Hofheim; Thomas Auler, Bad Soden; Hermann Bieringer, Eppstein; Felix Thürwächter, Bad Homburg, all of (DE)

(73) Assignee: Aventis CropScience GmbH, Frankfurt (DE)

( * ) Notice: Subject to any disclaimer, the term of this patent is extended or adjusted under 35 U.S.C. 154(b) by 0 days.

(21) Appl. No.: 09/705,001

(22) Filed: Nov. 2, 2000

(30) Foreign Application Priority Data

Nov. 4, 1999 (DE) .......................................... 199 53 136

(51) Int. Cl.[7] ........................ A01N 43/02; A01N 43/72; C07D 409/10; C07D 411/10; C07D 413/10
(52) U.S. Cl. ...................... 504/130; 504/139; 504/244; 504/282; 546/276.1; 548/364.1; 548/365.7; 548/110; 548/128; 548/131; 548/143; 548/203; 548/204; 548/214; 548/247; 548/240; 548/255; 548/266.2; 548/312.4; 544/96; 544/182
(58) Field of Search ................................. 504/282, 130, 504/139, 244; 548/365, 364.1, 365.7, 110, 128, 131, 143, 203, 204, 214, 240, 247, 255, 266.2, 312.4; 544/96, 182

(56) References Cited

U.S. PATENT DOCUMENTS

| | | | |
|---|---|---|---|
| 6,156,702 A | * | 12/2000 | Engel et al. ................ 504/282 |
| 6,207,618 B1 | * | 3/2001 | Engel et al. ................ 504/282 |

FOREIGN PATENT DOCUMENTS

| | | |
|---|---|---|
| EP | 0 2000 101 | 12/1986 |
| WO | WO 99/07697 | 2/1999 |
| WO | WO 99/10327 | 3/1999 |
| WO | WO 99/10328 | 3/1999 |

OTHER PUBLICATIONS

Database XFIRE; Registry No.: 3555871, also referred to as XP0021509602.
Database XFIRE; Registry No.: 3558085, also referred to as XP 002159603.
Database XFIRE; Registry No.: 3555047, also referred to as XP 002159604.
Database XFIRE; Registry No.: 7822088, also referred to as XP 002159605.
Database XFIRE; Registry No.: 7818187, also referred to as XP 002159606.
Database XFIRE; Registry No.: 7145572, also referred to as XP 002159608.
Database XFIRE; Registry No.: 8518285, also referred to as XP 002159609.

* cited by examiner

*Primary Examiner*—Richard L. Raymond
*Assistant Examiner*—Kahsay Habte
(74) *Attorney, Agent, or Firm*—Frommer Lawrence & Haug LLP

(57) ABSTRACT

Benzoylcyclohexanediones and benzoylpyrazoles, their preparation and their use as herbicides and plant growth regulators.

There are described benzoyl compounds of the formula (I), their preparation and their use as herbicides and plant growth regulators.

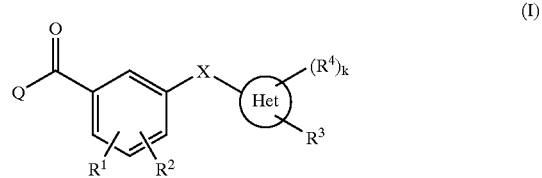

(I)

In this formula (I), $R^1$, $R^2$, $R^3$ and $R^4$ are various radicals, X is an alkylene chain which may contain a hetero atom and Het is a heterocycle or heteroaromatic ring.

17 Claims, No Drawings

BENZOYLCYCLOHEXANEDIONES AND BENZOYLPYRAZOLES, THEIR PREPARATION, AND THEIR USE AS HERBICIDES AND PLANT GROWTH REGULATORS

DESCRIPTION

Benzoylcyclohexanediones and benzoylpyrazoles, their preparation and their use as herbicides and plant growth regulators.

The invention relates to the technical field of the herbicides and plant growth regulators, in particular that of the herbicides for the selective control of broad-leaved weeds and grass weeds in crops of useful plants.

It is already known from various publications that certain benzoyl derivatives, including those which have, in the 3-position of their phenyl ring, for example a heterocyclic radical which is bound directly or via a monoatomic or polyatomic bridge, have herbicidal properties. Thus, WO 99/07697 describes benzoylpyrazoles which have attached to them in the abovementioned position an optionally substituted heterocyclic radical which is bound via a carbon atom chain. WO 99/10327 and WO 99/10328 disclose benzoylcyclohexanediones and benzoylpyrazoles, respectively, which have attached to them an optionally substituted heterocyclic radical which is bound via a chain of carbon atoms and a hetero atom.

However, the use of the benzoyl derivatives known from these publications frequently entails disadvantages in practice. Thus, the herbicidal or plant-growth-regulatory activity of the known compounds is not always sufficient, or, if the herbicidal activity is sufficient, then undesired damage to the useful plants is observed.

The object of the present invention is to provide compounds which have a herbicidal and plant-growth-regulatory action and- which overcome the disadvantages known from the prior art.

The present invention therefore relates to benzoyl derivatives of the formula (I) which are specifically substituted in the 3-position of the phenyl ring

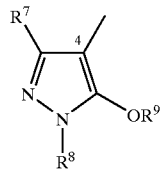
(I)

in which

Q is a radical of the formula (Q1) which is linked in the 2-position or a radical of the formula (Q2) which is linked in the 4-position

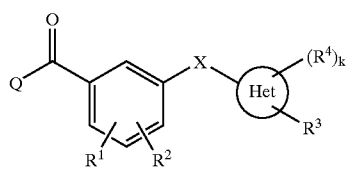
(Q1)

-continued

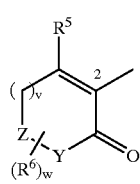
(Q2)

X is a straight-chain or branched $(C_1-C_6)$alkylene, $(C_2-C_6)$-alkenylene or $(C_2-C_6)$-alkynylene chain, which is substituted by w radicals selected from the group consisting of $OR^{3a}$, $OCOR^{3a}$, halogen, $OCONHR^{3a}$, $OSO_2R^{3a}$, $(C_1-C_6)$alkyl, $(C_2-C_6)$alkenyl, $(C_2-C_6)$alkynyl, phenyl and phenyl-$(C_1-C_6)$-alkyl, and which is interrupted by a hetero atom selected from the group consisting of oxygen and sulfur or which has this hetero atom attached to one of its chain ends, the abovementioned alkyl, alkenyl, alkynyl and phenyl radicals optionally being substituted by one or more radicals selected from the group consisting of halogen, hydroxyl, mercapto, amino, cyano, nitro, formyl, $(C_1-C_4)$-alkylamino, $(C_1-C_4)$-dialkylamino, $(C_1-C_4)$-alkoxycarbonyl, $(C_1-C_4)$-alkylcarbonyl, $(C_1-C_4)$-alkoxycarbonyloxy, $(C_1-C_4)$-alkyl, halo-$(C_1-C_4)$-alkyl, $(C_1-C_4)$-alkylthio, halo-$(C_1-C_4)$-alkylthio, $(C_1-C_4)$-alkoxy, halo-$(C_1-C_4)$-alkoxy;

Het is heterocyclyl or heteroaryl containing, as ring atom, at least one nitrogen atom and optionally additionally one, two or three hetero atoms selected from the group consisting of nitrogen, oxygen and sulfur;

$R^1$ and $R^2$ independently of one another are hydrogen, mercapto, nitro, halogen, cyano, thiocyanato, $(C_1-C_6)$-alkyl, $(C_1-C_6)$-alkoxy-$(C_1-C_6)$-alkyl, halo-$(C_1-C_6)$-alkyl, $(C_2-C_6)$-alkenyl, $(C_2-C_6)$-alkynyl, $OS(O)_nR^{10}$, $(C_1-C_6)$-alkyl-A, $(C_2-C_6)$-alkenyl-A, $(C_2-C_6)$-alkynyl-A, $(C_1-C_6)$-alkoxy-$(C_1-C_6)$-alkyl-A, or are $(C_2-C_6)$-alkenyloxy-$(C_1-C_6)$-alkyl-$(A)_p$, $(C_2-C_6)$-alkynyloxy-$(C_1-C_6)$-alkyl-$(A)_p$, $(C_3-C_9)$-cycloalkyl-$(A)_p$, $(C_3-C_9)$-cycloalkenyl-$(A)_p$, $(C_1-C_6)$-alkyl-$(C_3-C_9)$-cycloalkyl-$(A)_p$, $(C_1-C_6)$-alkyl-$(C_3-C_9)$-cycloalkyl-$(C_1-C_6)$-alkyl-$(A)_p$, $(C_1-C_6)$-alkyl-$(C_3-C_9)$-cycloalkenyl-$(A)_p$, $(C_1-C_6)$-alkyl-$(C_3-C_9)$-cycloalkenyl-$(C_1-C_6)$-alkyl-$(A)_p$, $(C_2-C_6)$-alkenyl-$(C_3-C_9)$-cycloalkyl-$(A)_p$, $(C_2-C_6)$-alkenyl-$(C_3-C_9)$-cycloalkyl-$(C_1-C_6)$-alkyl-$(A)_p$, $(C_2-C_6)$-alkenyl-$(C_3-C_9)$-cycloalkenyl-$(A)_p$, $(C_2-C_6)$-alkenyl-$(C_3-C_9)$-cycloalkenyl-$(C_1-C_6)$-alkyl-$(A)_p$, $(C_2-C_6)$-alkynyl-$(C_3-C_9)$-cycloalkyl-$(A)_p$, $(C_2-C_6)$-alkynyl-$(C_3-C_9)$-cycloalkyl-$(C_1-C_6)$-alkyl-$(A)_p$, $(C_2-C_6)$-alkynyl-$(C_3-C_9)$-cycloalkyenyl-$(A)_p$, $(C_2-C_6)$-alkynyl-$(C_3-C_6)$-cycloalkenyl-$(C_1-C_6)$-alkyl-$(A)_p$, $OR^{10}$, $OCOR^{10}$, $S(O)_nR^{10}$, $SO_2N(R^{10})_2$, $NR^{10}SO_2R^{10}$ or $NR^{10}COR^{10}$, each of which is substituted by m radicals selected from the group consisting of cyano and nitro and w radicals selected from the halogen group;

$R^3$ is hydrogen, hydroxyl, halogen, mercapto, amino, cyano, nitro, formyl, or is $(C_1-C_4)$-alkylamino, $(C_1-C_4)$-dialkylamino, $(C_1-C_4)$-alkoxycarbonyl, $(C_1-C_4)$-alkylcarbonyl, $(C_1-C_4)$-alkylcarbonyloxy, $(C_1-C_4)$-alkyl, halo$(C_1-C_4)$-alkyl, $(C_1-C_4)$-alkylthio, halo$(C_1-C_4)$-alkylthio, $(C_1-C_4)$-alkoxy or halo $(C_1-C_4)$-alkoxy, each of which is substituted by m radicals selected from the group consisting of cyano, formyl, nitro, $(C_1-C_4)$-alkylamino, $(C_1-C_4)$-dialkylamino, $(C_1-C_4)$-alkoxycarbonyl, $(C_1-C_4)$- alkylcarbonyl, ($C_1$–$C_4$)-alkylcarbonyloxy, ($C_1$–$C_4$)-alkyl, ($C_2$–$C_4$)-alkenyl, ($C_2$–$C_4$)-alkynyl, halo($C_1$–$C_4$)-alkyl, ($C_2$–$C_4$)-haloalkenyl, ($C_2$–$C_4$)-haloalkynyl, ($C_1$–$C_4$)-alkylthio, halo($C_1$–$C_4$)-alkylthio, ($C_1$–$C_4$)-alkoxy and halo($C_1$–$C_4$)-alkoxy;

$R^{3a}$ is hydrogen, ($C_1$–$C_6$)-alkyl, ($C_2$–$C_6$)-alkenyl, ($C_2$–$C_6$)-alkynyl, phenyl, phenyl-($C_1$–$C_6$)-alkyl, it being possible for the five last-mentioned radicals to be substituted in their nonaromatic moiety by w radicals selected from the group consisting of hydroxyl, halogen, amino, cyano, nitro, formyl, ($C_1$–$C_4$)-alkylamino, ($C_1$–$C_4$)-dialkylamino, ($C_1$–$C_4$)-alkoxycarbonyl, ($C_1$–$C_4$)-alkylcarbonyl, halo-($C_1$–$C_4$)-alkyl, ($C_1$–$C_4$)-alkylthio, halo-($C_1$–$C_4$)-alkylthio, ($C_1$–$C_4$)-alkoxy and halo-($C_1$–$C_4$)alkoxy;

$R^4$ is straight-chain or branched $[C(R^{11})_2]_m$-$(A)_p$-$[C(R^{11})_2]_m$-$R^{12}$;

A is oxygen or sulfur;

$R^5$ is $OR^{16}$, ($C_1$–$C_6$)-alkylthio, halo-($C_1$–$C_6$)-alkylthio, ($C_2$–$C_6$)-alkenylthio, halo-($C_2$–$C_6$)-alkenylthio, ($C_2$–$C_6$)-alkynylthio, halo-($C_2$–$C_6$)-alkynylthio, ($C_1$–$C_6$)-alkylsulfinyl, halo-($C_1$–$C_6$)-alkylsulfinyl, ($C_2$–$C_6$)-alkenylsulfinyl, halo-($C_2$–$C_6$)-alkenylsulfinyl, ($C_2$–$C_6$)-alkynylsulfinyl, halo-($C_2$–$C_6$)-alkynylsulfinyl, ($C_1$–$C_6$)-alkylsulfonyl, halo-($C_1$–$C_6$)-alkylsulfonyl, ($C_2$–$C_6$)-alkenylsulfonyl, halo-($C_2$–$C_6$)-alkenylsulfonyl, ($C_2$–$C_6$)-alkynylsulfonyl, halo-($C_2$–$C_6$)-alkynylsulfonyl, cyano, cyanato, thiocyanato or halogen;

$R^6$ is hydrogen, tetrahydropyran-3-yl, tetrahydropyran-4-yl, tetrahydrothiopyran-3-yl, or is ($C_1$–$C_6$)-alkyl, ($C_3$–$C_6$)-cycloalkyl, ($C_1$–$C_6$)-alkoxy, ($C_1$–$C_6$)-alkylcarbonyl, ($C_1$–$C_6$)-alkoxy-($C_1$–$C_6$)-alkyl, ($C_1$–$C_6$)-alkoxycarbonyl, ($C_1$–$C_6$)-alkylthio or phenyl, each of which is substituted by w radicals selected from the group consisting of halogen, ($C_1$–$C_6$)-alkylthio and ($C_1$–$C_6$)-alkoxy, or two radicals $R^6$ bound to a joint carbon atom form a chain selected from the group consisting of $OCH_2CH_2O$, $OCH_2CH_2CH_2O$, $SCH_2CH_2S$ and $SCH_2CH_2CH_2S$ which is optionally substituted by one to four methyl groups;

$R^7$ is hydrogen, ($C_1$–$C_6$)-alkyl or ($C_1$–$C_6$)-haloalkyl;

$R^8$ is ($C_1$–$C_6$)-alkyl, halo-($C_1$–$C_6$)-alkyl, or is phenyl which is optionally substituted by one or more radicals selected from the group consisting of halogen, nitro, cyano, ($C_1$–$C_4$)-alkyl, halo-($C_1$–$C_4$)-alkyl, ($C_1$–$C_4$)-alkoxy and halo-($C_1$–$C_4$)-alkoxy;

$R^9$ is hydrogen, ($C_1$–$C_6$)-alkyl, halo-($C_1$–$C_6$)-alkyl, ($C_1$–$C_6$)-alkylcarbonyl, halo-($C_1$–$C_6$)-alkylcarbonyl, ($C_1$–$C_6$)-alkoxycarbonyl, ($C_1$–$C_6$)-alkylsulfonyl, halo-($C_1$–$C_6$)-alkylsulfonyl, or is benzoyl, benzoylmethyl, phenoxycarbonyl or phenylsulfonyl, each of which is optionally substituted by one or more radicals selected from the group consisting of halogen, nitro, cyano, ($C_1$–$C_4$)-alkyl, halo-($C_1$–$C_4$)-alkyl, ($C_1$–$C_4$)-alkoxy and halo-($C_1$–$C_4$)-alkoxy;

$R^{10}$ is hydrogen, or is ($C_1$–$C_6$)-alkyl, halo-($C_1$–$C_6$)-alkyl, ($C_1$–$C_6$)-alkoxy, ($C_2$–$C_6$)-alkenyl, ($C_2$–$C_6$)-alkynyl, phenyl or phenyl-($C_1$–$C_6$)-alkyl, each of which is substituted by w radicals selected from the group consisting of hydroxyl, halogen, mercapto, amino, cyano, ($C_1$–$C_4$)-alkyl, ($C_1$–$C_4$)-alkoxy, ($C_1$–$C_4$)-alkylthio, di-($C_1$–$C_4$)-alkylamino, ($C_1$–$C_4$)-alkoxyimino, ($C_1$–$C_4$)-alkoxythiocarbonyl, ($C_1$–$C_4$)-alkylcarbonyl-($C_1$–$C_4$)-alkylamino, ($C_1$–$C_4$)-alkoxycarbonyl, ($C_1$–$C_4$)-alkylthiocarbonyl, di-($C_1$–$C_4$)-alkylaminocarbonyl, ($C_1$–$C_4$)-alkyliminooxy, ($C_1$–$C_4$)-alkoxyamino, ($C_1$–$C_4$)-alkylcarbonyl, ($C_1$–$C_4$)-alkoxy-($C_2$–$C_6$)-alkoxycarbonyl, ($C_1$–$C_4$)-alkylsulfonyl, heterocyclyl, heterocyclyloxy, phenyl, benzyl, heteroaryl, phenoxy, benzyloxy and heteroaryloxy;

$R^{11}$ is hydrogen, ($C_1$–$C_4$)-alkyl or halogen;

$R^{12}$ is cycloalkyl, cycloalkenyl, aryl, a heterocyclyl or heteroaryl containing one to four hetero atoms selected from the group consisting of oxygen, nitrogen, and sulfur, each of which is substituted by w radicals selected from the group consisting of halogen, cyano, formyl, nitro, ($C_1$–$C_4$)-alkyl, halo-($C_1$–$C_4$)-alkyl, ($C_1$–$C_4$)-alkoxy, halo-($C_1$–$C_4$)-alkoxy, ($C_1$–$C_4$)-alkylthio, halo-($C_1$–$C_4$)-alkylthio and $R^{13}$, or is a radical of the formula (Va) to (Vt):

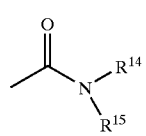

(Va)

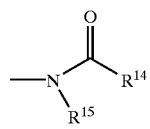

(Vb)

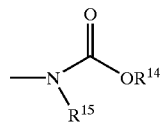

(Vc)

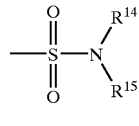

(Vd)

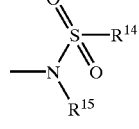

(Ve)

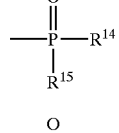

(Vf)

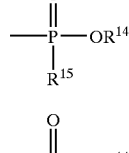

(Vg)

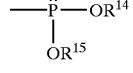

(Vh)

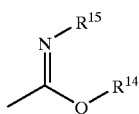 (Vi)

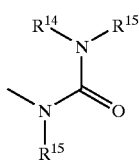 (Vj)

 (Vk)

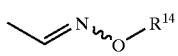 (Vl)

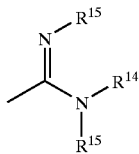 (Vm)

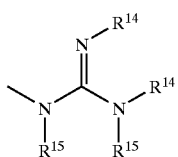 (Vn)

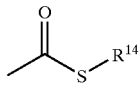 (Vo)

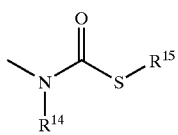 (Vp)

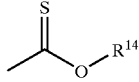 (Vq)

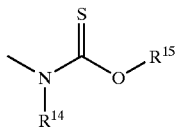 (Vr)

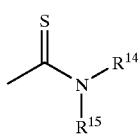 (Vs)

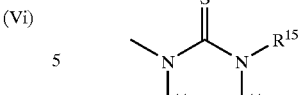 (Vt)

$R^{13}$ is [($C_1$–$C_4$)-alkylene-O—($C_1$–$C_4$)-alkylene]$_o$-O—($C_1$–$C_4$)-alkyl, or is ($C_1$–$C_4$)-alkyl, ($C_2$–$C_4$)-alkenyl or ($C_2$–$C_4$)-alkynyl, each of which is substituted by w halogen atoms;

$R^{14}$ is hydrogen, ($C_1$–$C_4$)-alkyl, ($C_1$–$C_4$)-alkoxy, ($C_2$–$C_4$)-alkenyl, ($C_2$–$C_4$)-alkynyl, ($C_3$–$C_9$)-cycloalkyl, aryl, aryl-($C_1$–$C_6$)-alkyl, heteroaryl, heterocyclyl, halo($C_1$–$C_4$)-alkyl;

$R^{15}$ is hydrogen, tetrahydrofuran-2-yl, ($C_1$–$C_4$)-alkyl, ($C_2$–$C_4$)-alkenyl, ($C_2$–$C_4$)-alkynyl, ($C_3$–$C_9$)-cycloalkyl, aryl, aryl-($C_1$–$C_6$)-alkyl, heteroaryl, heterocyclyl, halo($C_1$–$C_4$)-alkyl, or, if $R^{14}$ and $R^{15}$ are bound to one atom or to two directly adjacent atoms, they form together with the atoms binding them a saturated or partially or fully unsaturated five- to six-membered ring which optionally additionally contains a hetero atom selected from the group consisting of oxygen, nitrogen and sulfur;

$R^{16}$ is hydrogen, ($C_1$–$C_6$)-alkyl, halo-($C_1$–$C_6$)-alkyl, ($C_1$–$C_6$)-alkoxy($C_1$–$C_6$)-alkyl, formyl, ($C_1$–$C_6$)-alkylcarbonyl, ($C_1$–$C_6$)-alkoxycarbonyl, ($C_1$–$C_6$)-alkylaminocarbonyl, di-($C_1$–$C_6$)-alkylaminocarbonyl, ($C_1$–$C_6$)-alkylsulfonyl, halo-($C_1$–$C_6$)-alkylsulfonyl, benzoyl or phenylsulfonyl, the two last-mentioned groups being substituted by w identical or different radicals selected from the group consisting of ($C_1$–$C_6$)-alkyl, halo-($C_1$–$C_6$)-alkyl, ($C_1$–$C_6$)-alkoxy, halo-($C_1$–$C_6$)-alkoxy, halogen, cyano and nitro;

Y is a divalent unit selected from the group consisting of O, S, N—H, N—($C_1$–$C_6$)-alkyl, CHR$^6$ and C(R$^6$)$_2$;

Z is a direct bond or a divalent unit selected from the group consisting of O, S, SO, SO$_2$, N—H, N—($C_1$–$C_6$)-alkyl, CHR$^7$ or C(R$^7$)$_2$;

k in the event that Het is a bicyclic heteroaromatic ring or heterocycle, is 0, 1 or 2, and in the event that Het is a monocyclic heteroaromatic ring or heterocycle, 1 or 2;

m is 0, 1 or 2;

n is 0, 1 or 2;

o is 1, 2, 3 or 4;

p is 0 or 1;

v is 1 or 2;

w is 0, 1, 2, 3 or 4, and their agriculturally useful salts.

A large number of compounds of the formula (I) according to the invention may exist in various tautomeric structures, depending on external conditions such as solvent and pH. In the event that Q is Q$^1$ and R$^{12}$ is hydroxyl, several tautomeric structures are possible:

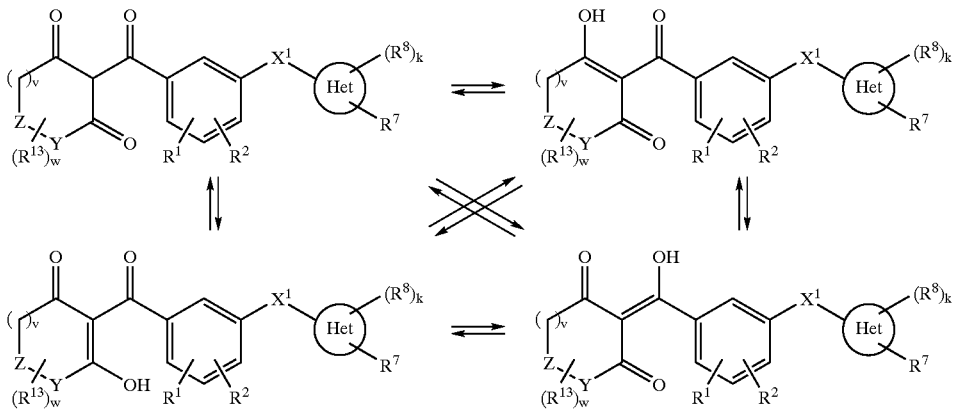

Depending on the nature of the substituents, the compounds of the formula (I) contain an acidic proton which can be eliminated by reaction with a base. Examples of suitable bases are hydrides, hydroxides and carbonates of lithium, sodium, potassium, magnesium and calcium, or else ammonia and organic amines such as triethylamine and pyridine. Such salts are also a subject matter of the invention.

In formula (I) and all subsequent formulae, chain-like carbon-containing radicals such as alkyl, alkoxy, haloalkyl, haloalkoxy, alkylamino and alkylthio and the corresponding unsaturated and/or substituted radicals in the carbon skeleton such as alkenyl and alkynyl can in each case be straight-chain or branched. Unless specified otherwise, the lower carbon skeletons, i.e. those having 1 to 6 carbon atoms, or in the case of unsaturated groups, those having 2 to 6 carbon atoms, are preferred amongst these radicals. Especially preferred are the groups having in each case up to 4 carbon atoms. Alkyl radicals, also in the composite meanings such as alkoxy, haloalkyl and the like, are, for example, methyl, ethyl, n- or i-propyl, n-, i-, t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals have the meaning of the unsaturated radicals which are possible and which correspond to the alkyl radicals; alkenyl is, for example, allyl, 1-methylprop-2-en-1-yl, 2-methyl-prop-2-en-1-yl, but-2-en-1-yl, but-3-en-1-yl, 1-methylbut-3-en-1-yl and 1-methylbut-2-en-1-yl; alkynyl is, for example, propargyl, but-2-in-1-yl, but-3-in-1-yl, 1-methylbut-3-in-1-yl. The multiple bond may be located in any position of the unsaturated radical.

Cycloalkyl without an indication of the number of carbon atoms in the ring is a carbocyclic saturated ring system, for example cyclopropyl, cyclopentyl or cyclohexyl. Analogously, cycloalkenyl is a monocyclic alkenyl group, for example cyclopropenyl, cyclobutenyl, cyclopentenyl and cyclohexenyl, where cycloalkenyl contains one double bond which can be located in any position.

In the case of a disubstituted amino group, such as dialkylamino, these two substituents can be identical or different.

Halogen is fluorine, chlorine, bromine or iodine. Haloalkyl, -alkenyl and -alkynyl are alkyl, alkenyl or alkynyl which are partially or fully substituted by halogen, preferably by fluorine or chlorine and/or by bromine, in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this also applies analogously to haloalkenyl and other halogen-substituted radicals.

The term heterocyclyl is to be understood as meaning the radicals of three-to ten-membered, saturated, partially or fully unsaturated, mono- or bicyclic heterocycles which, in addition to carbon ring members, contain one to four identical or different hetero atoms selected from the group consisting of nitrogen, oxygen and sulfur. If possible chemically, the linkage can take place at any position of the heterocycle. Heterocyclyl is preferably aziridinyl, tetrahydroquinolinyl, pyrrolidinyl, pyrrolinyl, pyrazolidinyl, pyrazolinyl, imidazolidinyl, imidazolinyl, oxazolidinyl, oxazolinyl, isoxazolidinyl, isoxazolinyl, thiazolinyl, thiazolidinyl, pyrazolidinyl, morpholinyl, piperidinyl, piperazinyl, azepanyl, 5,6,7,8-tetrahydrobenzoquinolinyl, 2-oxa-3-azabicyclo[3.3.0]-3-octenyl, 6-oxa-7-azabicyclo[4.3.0]-7-nonenyl and, unless heterocyclyl is to contain at least one nitrogen atom, tetrahydrofuranyl.

Heteroaryl represents the radical of a three- to ten-membered, mono- or bicyclic heteroaromatic ring which, in addition to carbon ring members, contains one to four identical or different hetero atoms selected from the group consisting of nitrogen, oxygen and sulfur. If possible chemically, the linkage may take place at any position of the heteroaromatic ring. Heteroaryl is preferably pyrrolyl, pyrazolyl, imidazolyl, oxazolyl, thiazolyl, isoxazolyl, isothiazolyl, 1,2,3-triazolyl, pyridazinyl, 1,2,4-triazolyl, 1,2,3-oxadiazolyl, 1,2,4-oxadiazolyl, 1,2,5-oxadiazolyl, tetrazolyl, 1,3,4-oxadiazolyl, 1,2,3-thiadiazolyl, 1,2,4-thiadiazolyl, 1,2,5-thiadiazolyl, 1,3,4-thiadiazolyl, pyridyl, pyrimidinyl, indolyl, pyrazinyl, 1,2,4-triazinyl, 1,3,5-triazinyl, benzoxazolyl, benzothiazolyl, quinolinyl, isoquinolinyl, quinazolinyl, quinoxalinyl, benzoxazolyl, benzothiazolyl, isoindolyl, isoquinolinyl, quinolinyl, quinazolinyl, 5,6,7,8-tetrahydrobenzoquinolinyl, quinoxalinyl, benzopyrazolyl, benzimidazolyl, benzotriazolyl and, unless heteroaryl is not to contain at least one nitrogen atom, furanyl and thienyl.

Aryl is an aromatic mono- or polycyclic hydrocarbon radical, for example phenyl, naphthyl, biphenyl and phenanthryl.

The term "partially or fully halogenated" is intended to express that some or all of the halogen atoms in the groups characterized thus can be replaced by identical or different halogen atoms as mentioned above.

If a group or a radical is polysubstituted, this is to be understood as meaning that the general principles of the structure of chemical compounds must be taken into consideration when combining the various substituents, i.e. to avoid the formation of compounds which are known to the expert as being chemically unstable or impossible. This also applies analogously to the combinations of individual radicals.

If a group or radical is polysubstituted by other radicals, these other radicals may be identical or different.

Depending on the type and linkage of the substituents, the compounds of the formula (I) may exist as stereoisomers. If, for example, one or more alkenyl groups are present, diastereomers can occur. If, for example, one or more asymmetric carbon atoms are present, enantiomers and diastereomers can occur. Stereoisomers can be obtained from the mixtures obtained from the preparation by customary separation methods, for example by chromatographic separation methods. Likewise, stereoisomers can be prepared selectively by employing stereoselective reactions using optically active starting materials and/or auxiliaries. The invention also relates to all stereoisomers and their mixtures which are covered by the formula I, but not defined specifically.

The proviso for the choice of the meanings of "Y" and "Z" is that "Y" and "Z" do not in each case simultaneously represent a heteroatomic divalent unit.

Benzoyl compounds of the formula (I) which are of greater interest in this context are those in which $R^1$ is nitro, halogen, cyano, $(C_1-C_6)$-alkyl, halo-$(C_1-C_6)$-alkyl, $(C_2-C_6)$-alkenyl, $(C_2-C_6)$-alkynyl, $OR^{10}$ or $S(O)_nR^{10}$;

$R^2$ is hydrogen, nitro, halogen, cyano, $(C_1-C_6)$-alkyl, halo-$(C_1-C_6)$-alkyl, $(C_2-C_6)$-alkenyl, $(C_2-C_6)$-alkynyl, $OR^{10}$ or $S(O)_nR^{10}$ and $R^{12}$ is $(C_3-C_6)$-cycloalkyl, substituted $(C_3-C_6)$-cycloalkenyl, phenyl, or a 5- to 6-membered heterocyclyl or heteroaryl—which contains one to four hetero atoms selected from the group consisting of oxygen, nitrogen and sulfur—each of which is substituted by w radicals selected from the group consisting of halogen, cyano, formyl, nitro, $(C_1-C_4)$-alkyl, halo-$(C_1-C_4)$-alkyl, $(C_1-C_4)$-alkoxy, halo-$(C_1-C_4)$-alkoxy, $(C_1-C_4)$-alkylthio, halo-$(C_1-C_4)$-alkylthio and $R^{13}$, or is a radical of the formula (Va) to (Vh).

Benzoyl compounds of the formula (I) which are of particular interest are those in which X is a $(C_1-C_3)$-alkylene, $(C_2-C_4)$-alkenylene or $(C_2-C_4)$-alkynylene chain which is interrupted by an oxygen atom or which has an oxygen atom attached to one of the chain ends, and $R^1$ is in the 2-position and $R^2$ in the 4-position of the benzoyl ring.

Benzoyl compounds of the formula (I) which are of very particular interest are those in which $R^1$ is chlorine, bromine, iodine, nitro or methyl;

$R^2$ is chlorine, bromine, trifluoromethyl or $(C_1-C_4)$-alkylsulfonyl;

$R^3$ is hydrogen and

X is a chain selected from the group consisting of $OCH_2$, $CH_2O$, $OCH_2CH_2$, $CH_2OCH_2$, $CH_2OCH_2CH=CH$, $CH=CHCH_2O$ and $C\equiv C-CH_2O$.

Benzoyl compounds of the formula (I) which are preferred are those in which k is 1;

Het is a radical from the group consisting of isoxazolidinyl, isoxazolinyl and isoxazolyl, and A is oxygen.

Benzoyl compounds of the formula (I) which are likewise preferred are those in which Het is a radical of the group consisting of 1,2,4-oxadiazolyl, 1,3,4-oxadiazolyl, oxazolyl and thiazolyl, and k is 1.

Benzoyl compounds of the formula (I) which are furthermore preferred are those in which Het is a radical selected from the group consisting of quinolinyl, 5,6,7,8-tetrahydroquinolinyl, benzoxazolyl and benzothiazolyl, and k is 0.

Benzoyl compounds of the formula (I) which are especially preferred are those in which Q is the radical of the formula Q1.

Benzoyl compounds of the formula (I) which are very especially preferred are those in which Q1 is a cyclohexane-1,3-dione ring of the formula (Q1a) which is linked in the 2-position;

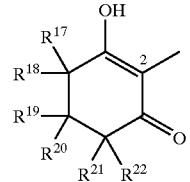

(Q1a)

$R^{17}$, $R^{18}$, $R^{20}$ and $R^{22}$ independently of one another are hydrogen or $(C_1-C_4)$-alkyl;

$R^{19}$ is hydrogen, tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, or is 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, each of which is optionally substituted by one to three $(C_1-C_4)$alkyl radicals, or is $(C_1-C_4)$-alkyl or $(C_1-C_3)$-cycloalkyl, each of which is substituted by w radicals selected from the group consisting of halogen, $(C_1-C_4)$-alkylthio and $(C_1-C_4)$-alkoxy;

$R^{21}$ is hydrogen, $(C_1-C_4)$-alkyl or $(C_1-C_6)$-alkoxycarbonyl, or $R^{19}$ and $R^{22}$ form a bond or a three- to six-membered ring, or $R^{19}$ and $R^{20}$ together with the carbon atom binding them form a carbonyl group.

In all the formulae mentioned hereinbelow, the substituents and symbols have the same meanings as described under formula (I), unless otherwise specified.

Depending on the meaning of the substituents, the compounds according to the invention can be prepared for example by one or more of the methods stated in the schemes which follow.

Compounds of the formula (I) according to the invention in which Q is Q1 and $R^5$ is hydroxyl can be prepared for example in accordance with Scheme 1. To this end, a cyclohexanedione of the formula (Q1b) is reacted in the presence of dehydrating agents such as dicyclohexylcarbodiimide, (in the event that R equals hydroxyl) or with base catalysis and in the presence of a cyanide source (in the event that R equals bromine or chlorine) or directly with base catalysis with a benzoic acid derivative of the formula (IVa) in which R is a nucleophilically exchangeable leaving group, an alkoxy group or hydroxyl. These methods are described, for example, in EP-A 0 369 803, EP-B 0 283 261 and WO 99/10327.

Scheme 1

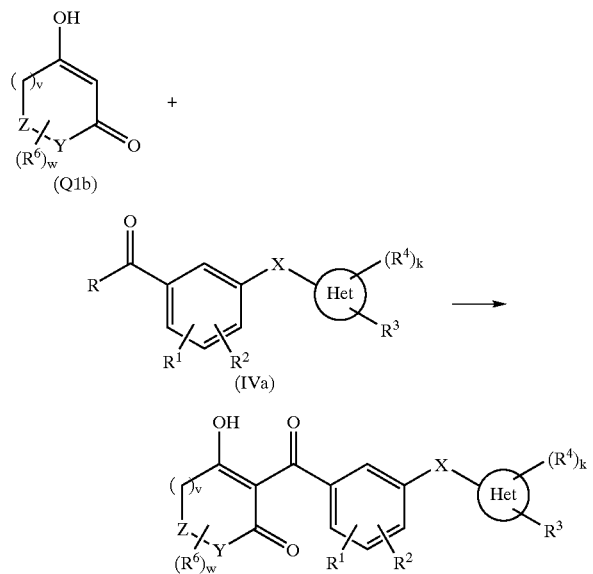

Compounds of the formula (I) according to the invention in which Q is Q2 can be prepared for example in accordance with Scheme 2 by means of the reaction of a pyrazole of the formula (Q2a) with a benzoic acid of the formula (IVb), which reaction is known from WO 99/10328.

Scheme 2

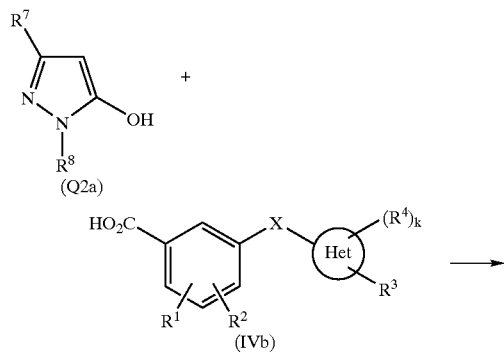

-continued

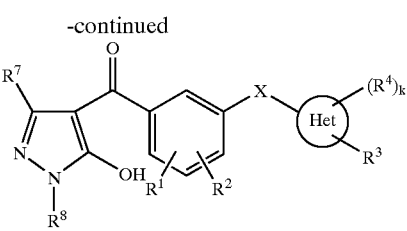

Compounds of the formula (I) according to the invention in Which Q is Q1 and $R^5$ is $OR^{16}$ can be obtained for example in accordance with Scheme 3 by electrophilic substitution reactions from the compounds prepared in accordance with Scheme 1 by reacting them with a compound of the formula $L^1$–$R^{16}$ (in which L is a nucleophilically exchangeable leaving group such as halogen, imidazolyl, pyridyl, acetate, trifluoroacetate, mesylate, triflate). Such reactions are known, for example, from WO 99/10328.

Scheme 3

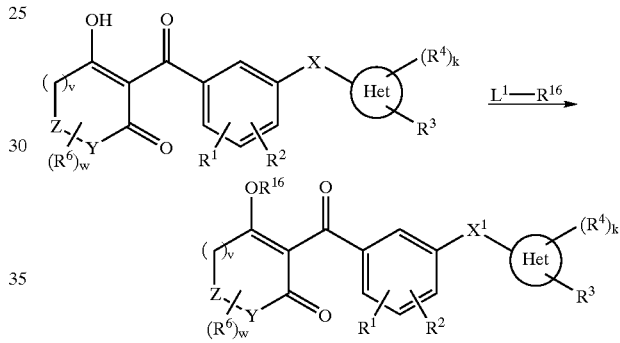

The reaction shown in Scheme 4 of a compound of the formula (Ia) according to the invention in which Q is Q1 and $R^5$ is hydroxyl with a halogenating reagent such as oxalyl chloride or oxalyl bromide gives compounds (1b) according to the invention which, when reacted with nucleophiles such as alkali metal cyanides, alkali metal cyanates, alkali metal thiocyanates, alkylthio alcohols and thiophenols, if appropriate with base catalysis, give further compounds (Ic) according to the invention in which $R^5$ is alkylthio, haloalkylthio, alkenylthio, haloalkenylthio, alkynylthio, haloalkynylthio, alkylsulfinyl, cyano, cyanato or thiocyanato. Such reactions are described, for example, in *Synthesis* 12, 1287 (1992). The reaction of compounds Ic, in which $R^5$ is a sulfur-containing radical, with an oxidant such as peroxyacetic acid, hydrogen peroxide, m-chloroperoxybenzoic acid and potassium peroxymonosulfate, yields further compounds of the formula (Ic) according to the invention in which $R^5$ is alkylsulfinyl, haloalkylsulfinyl, alkenylsulfinyl, haloalkenylsulfinyl, alkynylsulfinyl, haloalkynylsulfinyl, alkylsulfonyl, haloalkylsulfonyl, alkenylsulfonyl, haloalkenylsulfonyl, alkynylsulfonyl, optionally substituted phenylthio or haloalkynylsulfonyl. Such reactions are described, for example, in *J. Org. Chem.* 53, 532 (1988), *Tetrahedron Lett.* 21, 1287 (1981).

Scheme 4

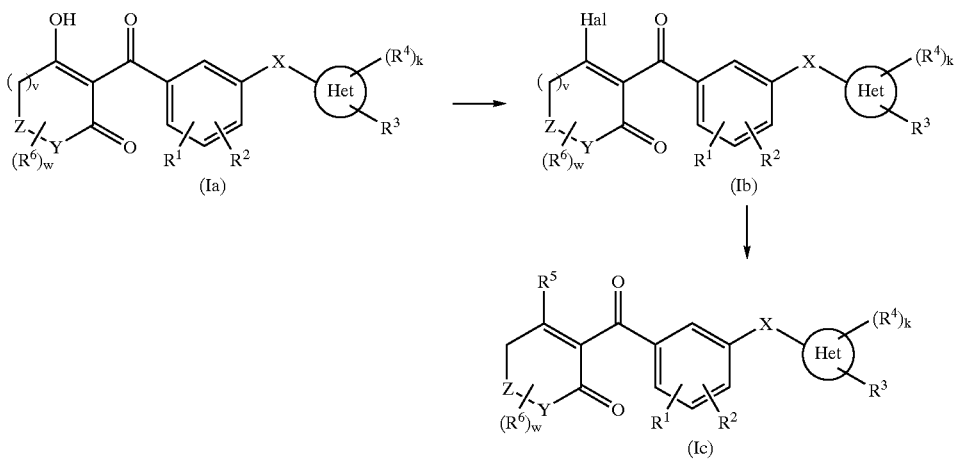

Compounds of the formula (I) according to the invention in which Q is Q2 and $R^9$ radicals other than hydrogen can be obtained for example in accordance with Scheme 5 by electrophilic substitution reactions from the compounds prepared in accordance with Scheme 2 by reacting them with a compound of the formula $L^2$–$R^9$ (in which $L^2$ is a nucleophilically exchangeable leaving group). Such reactions are known for example from WO 99110328.

Scheme 5

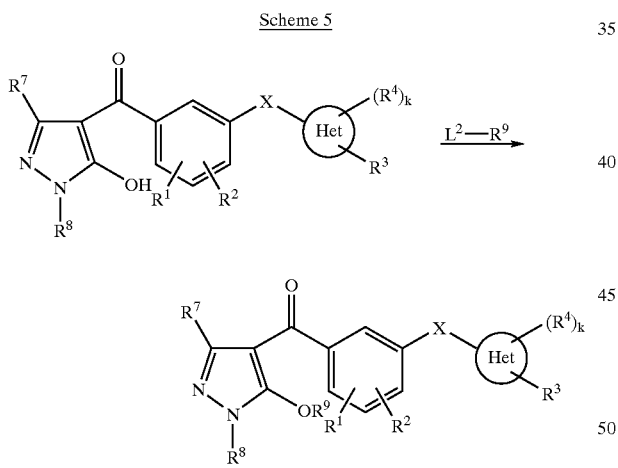

The benzoic acid derivatives of the formulae (IVa) and (IVb) which are employed in Schemes 1 and 2 can be prepared by reactions known to the skilled worker. For example, benzoic acid derivatives of the formula (IVa) in which R is alkoxy can be prepared in accordance with Scheme 6a by reacting a benzoic ester of the formula (IVc) with a heterocycle or heteroaromatic rings of the formula (VIa). Here, $X^1$ and $X^2$ denote in each case subsections of X. Such reactions are known for example from Houben-Weyl, Methoden der Organischen Chemie [Methods in Organic Chemistry], Volume E8a, pp. 45 to 176 (1993), and Volume E8c, pp. 397 to 630 (1994) Georg Thieme Verlag.

Scheme 6a

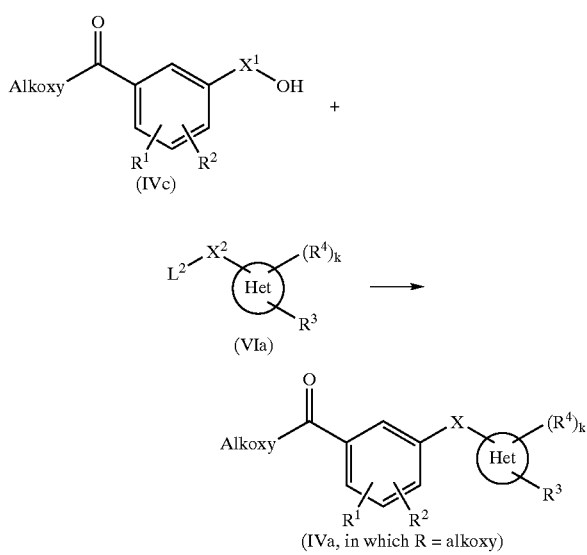

Benzoic acid derivatives of the formula (IVa) in which R is alkoxy can also be prepared according to Scheme 6b by reacting a benzoic ester of the formula (IVd) with a heterocycle or heteroaromatic ring of the formula (VIb). The reactions stated in Schemes 6a and 6b are known, for example, from Houben-Weyl, Methoden der Organischen Chemie, Volume VI/3, 4th Ed., pp. 493 et seq., Georg Thieme Verlag, 1965.

Scheme 6b

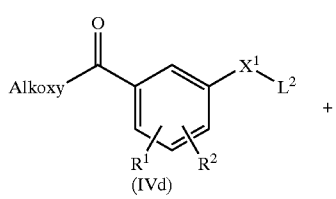

-continued

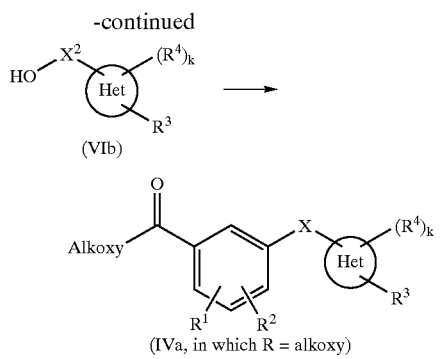

(VIb)

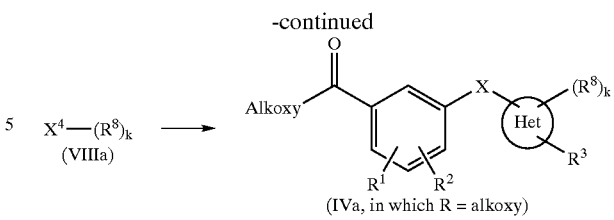

(IVa, in which R = alkoxy)

Benzoic acid derivatives of the formula (IVa) in which R is alkoxy can also be prepared in accordance with Scheme 6c by subjecting a benzoic ester of the formula (IVf) and a 1,3-dipolar compound of the formula (VIIa) to a so-called 1,3-dipolar cycloaddition reaction. Here, $X^3$ is an alkenylene or alkynylene unit which, if appropriate, has attached to it an oxygen or sulfur atom. A-B-C is the 1,3-dipolar unit of the compound (VIIa). Examples are axides, nitrile oxides and diazo compounds.

Scheme 6c

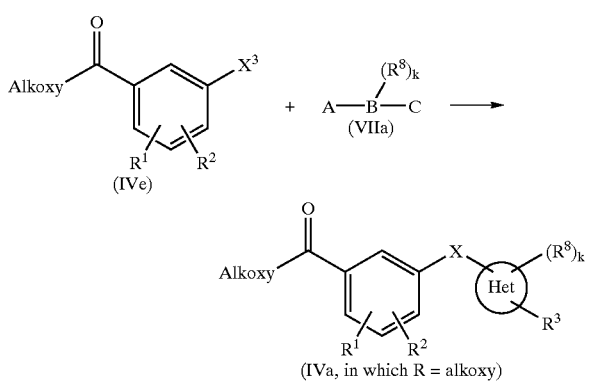

A 1,3-dipolar cycloaddition reaction may likewise be used to prepare benzoic acid derivatives of the formula (IVa) in accordance with Scheme 6d from a compound of the formula (IVf) and a compound of the formula (VIIIa). Here, $X^4$ is an alkenylene or alkynylene unit which optionally has attached to it an oxygen or sulfur atom. The abovementioned 1,3-dipolar cycloaddition reactions and the preparation of the 1,3-dipolar compounds are known, for example, from Houben-Weyl, Methoden der Organischen Chemie, Volume 10/4, pp. 55 to 91 (1968), Volume E5, pp. 1591 to 1592 and 1607 (1985), Volume E4b, pp. 968 to 1051 (1990), and Volume 8b, pp. 499 to 506 (1994) Georg Thieme Verlag.

Scheme 6d

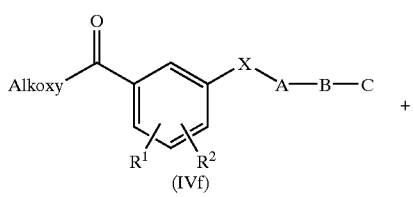

+

$X^4$—$(R^8)_k$
(VIIIa)

→

(IVa, in which R = alkoxy)

Benzoic acids of the formula (IVa) are new and also a subject matter of the invention.

The compounds of the formula (I) according to the invention have an outstanding herbicidal activity against a broad range of economically important monocotyledonous and dicotyledonous harmful plants. The active substances also act efficiently on perennial weeds which produce shoots from rhizomes, rootstocks or other perennial organs and which are difficult to control. In this context, it generally does not matter whether the substances are applied pre-planting, pre-emergence or post-emergence. Specifically, examples may be mentioned of some representatives of the monocotyledonous and dicotyledonous weed flora which can be controlled by the compounds according to the invention, without the enumeration leading to a restriction to certain species. Examples of weed species on which the active substances act efficiently are, from amongst the monocotyledons, Avena, Lolium, Alopecurus, Phalaris, Echinochloa, Digitaria, Setaria and also Cyperus species from the annual sector and from amongst the perennial species Agropyron, Cynodon, Imperata and Sorghum and also perennial Cyperus species. In the case of dicotyledonous species, the range of action extends to species such as, for example, Galium, Viola, Veronica, Lamium, Stellaria, Amaranthus, Sinapis, lpomoea, Sida, Matricaria and Abutilon from amongst the annuals, and Convolvulus, Cirsium, Rumex and Artemisia in the case of the perennial weeds. The active substances according to the inventon also effect outstanding control of weeds which occur under the specific conditions of rice growing, such as, for example, Echinochloa, Sagittaria, Alisma, Eleocharis, Scirpus and Cyperus. If the compounds according to the invention are applied to the soil surface before germination, the weed seedlings are either completely prevented from emerging, or the weeds grow until they have reached the cotyledon stage but then their growth stops, and, eventually, after three to four weeks have elapsed, they die completely. If the active substances are applied to the green parts of the plants post-emergence, growth likewise stops drastically a very short time after the treatment and the weak plants remain at the growth stage of the point of time of application, or they die completely after a certain time, so that in this manner competition from the weeds, which is harmful to the crop plants, is eliminated at a very early point in time and in a sustained manner.

Even though the compounds according to the invention have an outstanding herbicidal activity against monocotyledonous and dicotyledonous weeds, crop plants of economically important crops such as, for example, wheat, barley, rye, rice, maize, sugar beet, cotton and soya, are damaged not at all, or only to a negligible extent. For these reasons, the present compounds are highly suitable for selectively controlling undesired plant growth in plantings for agricultural use or in plantings of ornamentals.

Owing to their herbicidal and plant-growth-regulatory properties, the active substances can also be employed for controlling harmful plants in crops of known genetically modified plants, or genetically modified plants yet to be developed. As a rule, the transgenic plants are distinguished by particular advantageous properties, for example by resistances to certain pesticides, mainly certain herbicides, resistances to plant diseases or pathogens of plant diseases such as certain insects or microorganisms such as fungi, bacteria or viruses. Other particular properties relate, for example, to the harvested materials with regard to quantity, quality, storage properties, composition and specific constituents. Thus, transgenic plants are known where the starch content is increased or the starch quality is altered, or where the harvested material has a different fatty acid spectrum.

The compounds of the formula (I) according to the invention or their salts are preferably employed in economically important transgenic crops of useful plants and ornamentals, for example of cereal such as wheat, barley, rye, oats, sorghum and millet, rice, cassava and maize, or else crops of sugar beet, cotton, soya, oilseed rape, potatoes, tomatoes, peas and other vegetables. The compounds of the formula (I) can preferably be employed as herbicides in crops of useful plants which are resistant to the phytotoxic effects of the herbicides or have been rendered thus by recombinant methods.

Traditional ways of generating novel plants which have modified characteristics in comparison with existing plants consist, for example, in traditional breeding methods and the generation of mutants. However, it is also possible to generate novel plants with altered characteristics with the aid of recombinant methods (see, for example, EP-A-0221044, EP-A-0131624). For example, several cases have been described of recombinant modifications of crop plants with the purpose of modifying the starch synthesized in the plants (for example WO 92/11376, WO 92/14827, WO 91/19806), transgenic crop plants which are resistant to certain herbicides of the glufosinate type (cf., for example, EP-A-0242236, EP-A-242246) or the glyphosate type (WO 92/00377) or the sulfonylurea type (EP-A-0257993, U.S. Pat. No. 5,013,659), transgenic crop plants, for example cotton, which are capable of producing *Bacillus thuringiensis* toxins (Bt toxins) which make the plants resistant to specific pests (EP-A-0142924, EP-A-0193259), transgenic crop plants with a modified fatty acid spectrum (WO 91/13972).

A large number of techniques in molecular biology by means of which novel transgenic plants with altered characteristics can be generated are known in principle; see, for example, Sambrook et al., 1989, Molecular Cloning, A Laboratory Manual, 2nd Ed., Cold Spring Harbor Laboratory Press, Cold Spring Harbor, N.Y.; or Winnacker "Gene und Klone" [Genes and Clones], VCH Weinheim 2nd Edition 1996, or Christou, "Trends in Plant Science" 1 (1996) 423–431).

In order to perform such recombinant manipulations, nucleic acid molecules may be introduced into plasmids which allow mutagenesis or a sequence change to take place by means of recombination of DNA sequences. It is possible, for example, with the aid of the abovementioned standard methods to perform base exchanges, to remove subsequences or to add natural or synthetic sequences. To connect the DNA fragments to each other, adapters or linkers may be attached to the fragments.

For example, plant cells with a reduced activity of a gene product can be generated by expressing at least one corresponding antisense RNA, a sense RNA to achieve a cosuppressory effect, or by expressing at least one ribozyme of suitable construction which specifically cleaves transcripts of the abovementioned gene product.

To this end it is possible to make use of, on the one hand, DNA molecules which encompass the entire coding sequence of a gene product inclusive of any flanking sequences which may be present, and on the other hand DNA molecules which only encompass parts of the coding sequence, these parts having to be long enough in order to effect, in the cells, an antisense effect. Use may also be made of DNA sequences which show a high degree of homology to the coding sequences of a gene product, but which are not completely identical.

When nucleic acid molecules are expressed in plants, the protein which has been synthesized may be located in any desired compartment of the plant cell. However, to achieve localization in a particular compartment, it is possible, for example, to link the coding region with DNA sequences which guarantee localization in a particular compartment. Such sequences are known to the skilled worker (see, for example, Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

The transgenic plant cells may be regenerated by known techniques to give rise to intact plants. In principle, the transgenic plants can be plants of any desired plant species, that is to say monocotyledonous and also dicotyledonous plants.

This allows transgenic plants to be obtained which exhibit altered characteristics by means of overexpression, suppression or inhibition of homologous (=natural) genes or gene sequences or by means of expression of heterologous (=foreign) genes or gene sequences.

The compounds according to the invention can preferably be employed in transgenic crops which are resistant to herbicides from the group of the sulfonylureas, glufosinate ammonium or glyphosate isopropylammonium and analogous active substances.

When the active substances according to the invention are used in transgenic crops, effects in addition to the herbicidal effects to be observed in other crops are frequently found which are specific for application in the particular transgenic crop, for example an altered or specifically widened weed spectrum which can be controlled, altered application rates which may be employed for application, preferably good combinability with the herbicides to which the transgenic crop is resistant, and an effect on growth and yield of the transgenic crop plants. The invention therefore also relates to the use of the compounds according to the invention as herbicides for controlling harmful plants in transgenic crop plants.

The substances according to the invention additionally also have growth-regulatory properties in crop plants. They engage in the plants' metabollism in a regulatory manner and can thus be employed to specifically affect plant constituents and to facilitate harvesting such as, for example by provoking desication and stunted growth. Moreover, they are also suitable for the general control and inhibition of undesired vegetative growth without killing the plants in the process. Inhibiting the vegetative growth plays an important role in a large number of mono- and dicotyledonous crops since lodging can be reduced hereby, or completely prevented.

The compounds according to the invention can be applied in the customary preparations in the form of wettable powders, emulsifiable concentrates, sprayable solutions, dusts or granules. A subject matter of the invention is therefore also herbicidal and plant-growth-regulatory compositions which comprise compounds of the formula (I).

The compounds of the formula (I) can be formulated in various ways, depending on the prevailing biological and/or chemical-physical parameters. Suitable possibilities of formulations are, for example, wettable powders (WP), water-soluble powders (SP), water-soluble concentrates, emulsifiable concentrates (EC), emulsions (EW), such as oil-in-water and water-in-oil emulsions, sprayable solutions, suspension concentrate (SC), oil- or water-based dispersions, oil-miscible solutions, capsule suspensions (CS), dusts (DP), seed-dressing products, granules for spreading and soil application, granules (GR) in the form of microgranules, spray granules, coated granules and adsorption granules, water-dispersible granules (WG), water-soluble granules (SG), ULV formulations, microcapsules and waxes. These individual types of formulations are known in principle and are described, for example, in Winnacker-Küchler, "Chemische Technologie" [Chemical Engineering], Volume 7, C. Hauser Verlag Munich, 4th Ed., 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required such as inert materials, surfactants, solvents and further additives are likewise known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Engineering], Volume 7, C. Hauser Verlag Munich, 4th Ed. 1986.

Wettable powders are preparations which are uniformly dispersible in water and which, besides the active substance, also comprise ionic and/or anionic surfactants (wetters, dispersants), for example polyoxethylated alkylphenols, polyoxethylated fatty alcohols, polyoxethylated fatty amines, fatty alcohol polyglycol ether sulfates, alkanesulfonates, alkylbenzenesulfonates, sodium 2,2'-dinaphthylmethane-6,6'-disulfonate, sodium ligninosulfonate, sodium dibutyinaphthalenesulfonate or else sodium oleoylmethyltaurinate, in addition to a diluent or inert substance. To prepare the wettable powders, the herbicidal active substances are ground finely, for example in customary apparatuses such as hammer mills, blower mills and air-jet mills, and simultaneously or subsequently mixed with the formulation auxiliaries.

Emulsifiable concentrates are prepared by dissolving the active substance in an organic solvent, for example butanol, cyclohexanone, dimethylformamide, xylene or else higher-boiling aromatics or hydrocarbons or mixtures of the organic solvents with addition of one or more ionic and/or nonionic surfactants (emulsifiers). The following can be used as emulsifiers: for example calcium alkylarylsulfonates such as calcium dodecylbenzenesulfonate or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as, for example, polyoxyethylene sorbitan fatty acid esters.

Dusts are obtained by grinding the active substance with finely divided solid materials, for example talc, natural clays such as kaolin, bentonite and pyrophyllite, or diatomaceous earth.

Suspension concentrates may be water- or oil-based. They can be prepared for example by wet-grinding by means of commercially available bead mills, if appropriate with addition of surfactants as, for example, have already been listed above in the case of the other formulation types.

Emulsions, for example, oil-in-water emulsions (EW) can be prepared for example by means of stirrers, colloid mills and/or static mixers using aqueous organic solvents and, if appropriate, surfactants as, have already been mentioned above in the case of the other formulation types.

Granules can be produced either by spraying the active substance onto adsorptive, granulated inert material or by applying active substance concentrates to the surface of carriers such as sand, kaolinites or of granulated inert material by means of binders, for example polyvinyl alcohol, sodium polyacrylate or else mineral oils. Suitable active substances may also be granulated in the manner which is conventional for the production of fertilizer granules, if desired as a mixture with fertilizers.

As a rule, water-dispersible granules are prepared by the customary methods such as spray-drying, fluidized-bed granulation, disc granulation, mixing by means of high-speed mixers and extrusion without solid inert material.

To prepare disc, fluidized-bed, extruder and spray granules, see, for example, methods in "Spray-Drying Handbook" 3rd Ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, pp. 8–57.

For further details on the formulation of crop protection products, see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

As a rule, the agrochemical preparations comprise 0.1 to 99% by weight, in particular 0.1 to 95% by weight, of active substance of the formula (I). In wettable powders, the active substance concentration is, for example, approximately 10 to 90% by weight, the remainder to 100% by weight being composed of customary formulation components. In the case of emulsifiable concentrates, the active substance concentration may be approximately 1 to 90, preferably 5 to 80%, by weight. Formulations in the form of dusts comprise 1 to 30% by weight of active substance, preferably in most cases 5 to 20% by weight of active substance, sprayable solutions comprise approximately 0.05 to 80, preferably 2 to 50%, by weight of active substance. In the case of water-dispersible granules, the active substance content depends partly on whether the active compound is in liquid or solid form and on which granulation auxiliaries, fillers and the like are being used. In the case of the water-dispersible granules, the active substance content is, for example, between 1 and 95% by weight, preferably between 10 and 80% by weight.

In addition, the active substance formulations mentioned comprise, if appropriate, the adhesives, wetters, dispersants, emulsifiers, penetrants, preservatives, antifreeze agents, solvents, fillers, carriers, colorants, antifoams, evaporation inhibitors, pH regulators and viscosity regulators which are conventional in each case.

Based on these formulations, it is also possible to prepare combinations with other pesticidally active substances such as, for example, insecticides, acaricides, herbicides, fungicides, or else with safeners, fertilizers and/or growth regulators, for example in the form of a readymix or a tank mix.

Components in combinations for the active substances according to the invention in formulation mixtures or in the tank mix which can be employed are, for example, known active substances as are described, for example, in Weed Research 26, 441–445 (1986) or "The Pesticide Manual", 11th edition, The British Crop Protection Council and the Royal Soc. of Chemistry, 1997 and the literature cited therein. Examples of known herbicides which can be combined with the compounds of the formula (I) are the following active substances (note: either the common name in accordance with the International Organization for Standardization (ISO) or the chemical name of the compounds, if appropriate together with a customary code number, is given):

acetochlor; acifluorfen; aclonifen; AKH 7088, i.e. [[[1-[5-[2-chloro-4-(trifluoromethyl)phenoxy]-2-nitrophenyl]-2-methoxyethylidene]-amino]oxy]acetic acid and its methyl ester; alachlor; alloxydim; ametryn; amidosulfuron; amitrol; AMS, i.e. ammonium sulfamate; anilofos; asulam; atrazine; azimsulfurone (DPX-A8947); aziprotryn; barban; BAS 516 H, i.e. 5-fluoro-2-phenyl-4H-3,1-benzoxazin-4-one; benazolin; benfluralin; benfuresate; bensulfuron-methyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone (ICI-A0051); CDAA, i.e. 2-chloro-N,N-di-2-propenylacetamide; CDEC, i.e. 2-chloroallyl diethyl dithiocarbamate; chlomethoxyfen; chloramben; chlorazifop-butyl, chlormesulon (ICI-A0051); chlorbromuron; chlorbufam; chlorfenac; chlorflurecol-methyl; chloridazon; chlorimuron-ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (for example butyl ester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofopmethyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carbox-amide; endothal; EPTC; esprocarb; ethalflu-ralin; ethametsulfuron-methyl; ethidimuron; ethiozin; ethofumesate; F5231, i.e. N-[2-chloro-4-fluoro-5[4-(3-fluoropropyl)-4,5-dihydro-5-oxo-1H-tetrazol-1-yl]phenyl]-ethanesulfon-amide; ethoxyfen and its esters (for example ethyl ester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flampropmethyl; flazasulfuron; fluazifop and fluazifop-P and their esters, for example fluazifop-butyl and fluazifop-P-butyl; fluchloralin; flumetsulam; flumeturon; flumiclorac and its esters (for example pentyl ester, S-23031); flumioxazin (S-482); flumipropyn; flupoxam (KNW-739); fluorodifen; fluoroglycofen-ethyl; flupropacil (UBIC-4243); fluridone; flurochloridone; fluroxypyr; flurtamone; fomesafen; fosamine; furyloxyfen; glufosinate; glyphosate; halosafen; halosulfuron and its esters (for example methyl ester, NC-319); haloxyfop and its esters; haloxyfop-P (=R-haloxyfop) and its esters; hexazinone; imazapyr; imazamethabenzmethyl; imazaquin and salts such as the ammonium salt; ioxynil; imazethamethapyr; imazethapyr; imazosulfuron; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; metham; methabenzthiazuron; methazole; methoxyphenone; methyidymron; metabenzuron, methobenzuron; metobromuron; metolachlor; metosulam (XRD 511); metoxuron; metribuzin; metsulfuron-methyl; MH; molinate; monalide; monolinuron; monuron; monocarbamide dihydrogensulfate; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; piperophos; piributicarb; pirifenopbutyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (for example propargyl ester); quinclorac; quinmerac; quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)-phenoxy]-2-naphthalenyl]oxy]propanoic acid and its methyl ester; sulfentrazon (FMC-97285, F-6285); sulfazuron; sulfometuron-methyl; sulfosate (ICI-A0224); TCA; tebutam (GCP-5544); tebuthiuron; terbacil; terbucarb; terbuchlor; terbumeton; terbuthylazine; terbutryn; TFH 450, i.e. N,N-Diethyl-3-[(2-ethyl-6-methylphenyl)sulfonyl]-1H-1,2,4-triazole-1-carboxamide; thenylchlor (NSK-850); thiazafluron; thiazopyr (Mon-13200); thidiazimin (SN-24085); thiobencarb; thifensulfuron-methyl; tiocarbazil; tralkoxydim; tri-allate; triasulfuron; triazofenamide; tribenuron-methyl; triclopyr; tridiphane; trietazine; trifluralin; triflusulfuron and its esters (for example methyl ester, DPX-66037); trimeturon; tsitodef; vernolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

For use, the formulations which are present in commercially available form are, if appropriate, diluted in the customary manner, for example using water in the case of wettable powders, emulsifiable concentrates, dispersions and water-dispersible granules. Preparations in the form of dusts, soil granules, granules for spreading, and sprayable solutions are usually not diluted any further with other inert substances prior to use.

The required application rate of the compounds of the formula (I) varies with the external conditions such as, inter alia, temperature, humidity and the nature of the herbicide used. It can vary within wide limits, for example between 0.001 and 10.0 kg/ha or more of active substance, but it is preferably between 0.005 and 5 kg/ha.

The examples hereinbelow illustrate the invention.

A. CHEMICAL EXAMPLES

The starting compound ethyl 2,4-dibromo-3-hydroxybenzoate was prepared in accordance with U.S. Pat. No. 5,026,896, and 2-chloro-3-hydroxy-4-methylsulfonylbenzoic acid was prepared in accordance with EP 0 195 247.

1. Preparation of 2-(2-Chloro-3-(3-phenylisoxazol-5-yl)methoxy-4-methylsulfonylbenzoyl)cyclohexane-1,3-dione Step 1: Methyl 2-Chloro-3-hydroxy-4-methylsulfonylbenzoate 22.94 g (91.5 mmol) of 2-chloro-3-hydroxy-4-methylsulfonylbenzoic acid were dissolved in 1000 ml of methanol. 82.3 ml (1545 mmol) of concentrated $H_2SO_4$ were added dropwise and the mixture was refluxed for 4 hours. The reaction mixture was concentrated on a rotary evaporator and the residue was taken up in methylene chloride. The mixture was washed with water, dried over $Na_2SO_4$ and evaporated completely on the rotary evaporator. This gave methyl 2-chloro-3-hydroxy-4-methylsulfonylbenzoate as white solid with a melting point of 124–126° C.

Yield: 16.02 g (66% of theory); $R_f$ (ethyl acetate): 0.25 $^1$H NMR: δ [CDCl3] 3.18 (s, 3H), 3.96 (s, 3H), 7.44 (d, 1H), 7.75 (d, 1H).

Step 2: Methyl 2-Chloro-3-(propargyl-3-oxy)-4-methylsulfonylbenzoate 4.18 g (30.2 mmol) of potassium carbonate and 3.56 g (30.2 mmol) of 3-bromopropyne were dissolved in 50 ml of N,N-dimethylformamide. 4.00 g (15.1 mol) of methyl 2-chloro-3-hydroxy-4-methylsulfonylbenzoate were added at RT and the mixture was heated at 70° C. for 5 hours. Then, it was poured into water and extracted with diethyl ether. The combined organic phases were washed with water, dried over $Na_2SO_4$ and evaporated completely on a rotary evaporator, which gave methyl 2-chloro-3-(propargyl-3-oxy)-4-methylsulfonylbenzoate as brown oil.

Yield: 4.39 g (96% of theory); $R_f$ (ethyl acetate) 0.88 $^1$H NMR: δ [CDCl3] 2.67 (m, 1H), 3.30 (s, 3H), 3.98 (s, 3H), 4.90 (d, 2H), 7.69 (d, 1H), 7.93 (d, 1H).

Step 3: Methyl 2-Chloro-3-(3-phenylisoxazol-5-yl)methoxy)-4-methylsulfonylbenzoate 4.39 g (14.5 mmol) of methyl 2-chloro-3-(propargyl-3-oxy)-4-methylsulfonylbenzoate and 4.22 g (34.8 mmol) of benzaldehyde oxime were introduced into 45 ml of methylene chloride. 20.43 g (35.7 mmol) of sodium hypochlorite solution (13% strength) were slowly added dropwise. The reaction mixture was stirred for 5 hours at RT. It was subsequently extracted with $CH_2Cl_2/H_2O$. The combined organic phases were washed with $H_2O$, dried over $Na_2SO_4$ and evaporated completely on a rotary evaporator. The crude product was chromatographed on silica gel with heptane/ethyl acetate 6:4, which gave methyl 2-chloro-3-(3-phenylisoxazol-5-yl)methoxy)-4-methylsulfonylbenzoate as yellow solid of melting point 134–140° C.

Yield: 2.76 g (45% of theory); $R_f$ (ethyl acetate): 0.86 $^1$H NMR: δ [CDCl3] 3.26 (s, 3H), 4.00 (s, 3H), 5.40 (s, 2H), 6.85 (s, 1H), 7.48 (m, 3H), 7.74 (d, 1H), 7.85 (m, 2H), 7.98 (d, 1H).

Step 4: 2–Chloro-3-(3-phenylisoxazol-5-ylmethoxy)-4-methylsulfonyl-benzoic Acid 2.71 g (6.4 mmol) of methyl 2-chloro-3-(3-phenylisoxazol-5-yl)methoxy)-4-methylsulfonylbenzoate were dissolved in a mixture of 20 ml of tetrahydrofuran and 20 ml of water, and 0.28 g (7.10 mmol) of sodium hydroxide was added. The mixture was stirred for 12 hours at RT and evaporated completely on a rotary evaporator. The residue was taken up in water, and the mixture was treated with 6 N HCl, during which process 2-chloro-3-(3-phenylisoxazol-5-yl)methoxy)-4-methylsulfonic acid precipitated as colorless solid which, after filtration with suction and drying, has a melting point of 188–193° C.

Yield: 2.51 g (96% of theory); $R_f$ (ethyl acetate): 0.03 $^1$H NMR: δ [d6-DMSO] 3.36 (s, 3H), 5.33 (s, 2H), 7.29 (s, 1H), 7.16 (d, 1H), 7.53 (m, 3H), 7.74 (d, 1H), 7.90 (m, 4H).

Step 5: 3-Oxo-1-cyclohexenyl 2-Chloro-3-((3-phenylisoxazol-5-yl)methoxy)-4-methylsulfonylbenzoate 0.80 g (2.00 mmol) of 2-chloro-3-(3-phenylisoxazol-5-yl)methoxy)-4-methylsulfonylbenzoic acid, 0.24 g (2.20 mmol) of cyclohexane-1,3-dione, 0.42 g (2.20 mmol) of N'-(3-dimethylaminopropyl)-N-ethylcarbodiimide hydrochloride and 0.002 g of dimethylaminopyridine were stirred for 10 hours at RT in 10 ml of $CH_2Cl_2$. The mixture was subsequently diluted with $CH_2Cl_2$ and washed with 0.5 N HCl, with water, with saturated $NaHCO_3$ solution and again with water. After the combined organic phases had been dried over $Na_2SO_4$ and evaporated completely on a rotary evaporator, 3-oxo-1-cyclohexenyl 2-chloro-3-((3-phenylisoxazol-5-yl)methoxy)-4-methylsulfonylbenzoate was obtained in the form of a brown resin.

Yield: 0.86 g (60% of theory) $R_f$ (ethyl acetate): 0.87 $^1$H NMR: δ [CDCl3] 2.17 (m, 2H), 2.49 (m, 2H), 2.69 (m, 2H), 3.28 (s, 3H), 5.43 (s, 2H), 6.08 (m, 1H), 6.84 (s, 1H), 7.16 (d, 1H), 7.47 (m, 3H), 7.82 (m, 5H), 8.05 (d, 1H).

Step 6: 2-(2-Chloro-3-(3-phenylisoxazol-5-yl)methoxy-4-methylsulfonylbenzoyl)cyclohexane-1,3-dione 0.50 g (1.00 mmol) of 3-oxo-1-cyclohexenyl 2-chloro-3-(3-phenylisoxazol-5-yl)methoxy)-4-methylsulfonylbenzoate were dissolved in 10 ml of acetonitrile. 3 drops of acetone cyanohydrin and 0.18 g (1.70 mmol) of triethylamine were added. The mixture was stirred for 2 hours at RT, whereupon 0.027 g (0.4 mmol) of potassium cyanide were added. After a further 10 hours at room temperature, the mixture was evaporated completely, and the residue was taken up in water and treated with 6 N hydrochloric acid. The mixture was subsequently extracted with methylene chloride. After the combined organic phases had been dried over $Na_2SO_4$ and evaporated completely on a rotary evaporator, (2-chloro-3-((3-phenylisoxazol-5-yl)methoxy)-4-methylsulfonylbenzoyl)cyclohexane-1,3-dione was obtained in the form of a brown solid of melting point 72–78° C.

Yield: 0.39 g (55% of theory); $R_f$ (ethyl acetate): 0.24 $^1$H NMR: δ [CDCl3] 2.08 (m, 2H), 2.58 (m, 2H), 2.83 (m, 2H), 3.26 (s, 3H), 5.38 (s, 2H), 6.83 (s, 1H), 7.16 (d, 1H), 7.46 (m, 3H), 7.82 (m, 2H), 7.97 (d, 1H).

2. Preparation of 2-(2,4-Dibromo-3-(3-phenylisoxazolin-5-yl)methoxy)-cyclohexane-1,3-dione Step 1: Methyl 2,4-Dibromo-3-(propargyl-3-oxy)benzoate 14.72 g (10.65 mmol) of potassium carbonate and 12.95 g (10.70 mmol) of 3-bromopropene were dissolved in 300 ml of N,N-dimethylformamide. 17.00 g (5.25 mol) of ethyl 2,4-dibromo-3-hydroxybenzoate were added at RT and the mixture was heated for 5 hours at 70° C. It was subsequently poured into water and extracted with diethyl ether. The combined organic phases were washed with water, dried over $Na_2SO_4$ and evaporated completely, which gave methyl 2,4-dibromo-3-(propargyl-3-oxy)benzoate as yellow oil.

Yield: 16.58 g (86% of theory); $R_f$(ethyl acetate): 0.93 $^1$H NMR: δ [CDCl3] 1.20 (t, 3H), 4.41 (q, 2H), 4.53 (dd, 2H), 5.38 (dd, 1H), 5.46 (dd, 1H), 6.19 (m, 1H), 7.34 (d, 1H), 7.53 (d, 1H).

Step 2: Ethyl 2,4-Dibromo-(3-phenylisoxazolin-5-yl)methoxy)-4-benzoate 4.00 g (11.00 mmol) of methyl 2,4-dibromo-3-(propargyl-3-oxy)benzoate and 1.60 g (13.2 mmol) of benzaldehyde oxime were introduced into 40 ml of methylene chloride. 7.78 g (13.50 mmol) of sodium hypochlorite solution (13% strength) were slowly added dropwise. The mixture was stirred for 10 hours at RT. Then, the mixture was extracted with methylene chloride/water. The combined organic phases were dried over $Na_2SO_4$ and evaporated completely. The crude product was chromatographed on silica gel with heptane/ethyl acetate 8:2, which gave ethyl 2,4-dibromo-((3-phenylisoxazolin-5-yl)methoxy)-4-benzoate as a colorless oil.

Yield: 4.21 g (79% of theory); $R_f$(ethyl acetate): 0.91 $^1$H NMR: δ [CDCl3] 1.20 (t, 3H), 3.56 (m, 2H), 3.67 (m, 2H), 4.18 (m, 2H), 4.38 (q, 2H), 5.21 (m, 1H), 7.20 (d, 1H), 7.42 (m, 3H), 7.56 (d, 1H), 7.72 (m, 2H).

Step 3: 2,4-Dibromo-(3-phenylisoxazolin-5-yl)methoxy)-4-benzoate 3.70 g (7.70 mmol) of ethyl 2,4-dibromo-((3-phenylisoxazolin-5-yl)methoxy)-4-benzoic acid were dissolved in a mixture of 20 ml of tetrahydrofuran and 20 ml of water and treated with 0.34 g (8.40 mmol) sodium hydroxide. The mixture was stirred for 12 hours at RT and evaporated completely on a rotary evaporator. The residue was taken up in water and treated with 6 N HCl. Then, the mixture was extracted with methylene chloride. The combined organic phases were dried over $Na_2SO_4$ and evaporated completely on a rotary evaporator. This gave 2,4-dibromo(3-phenylisoxazolin-5-yl)methoxy)-4-benzoate of melting point 162–165° C.

Yield: 3.10 g (88% of theory); $R_f$(ethyl acetate): 0.04 $^1$H NMR: δ [d6-DMSO] 4.17 (m, 2H), 5.13 (m, 1H), 7.40 (d, 1H), 7.43 (m, 3H), 7.66 (m, 2H), 7.73 (d, 1H).

Step 4: 3-Oxo-1-cyclohexenyl 2,4-Dibromo-3-(3-phenylisoxazolin-5-yl)methoxy)benzoate 2.60 g (5.70 mmol) of 2,4-dibromo(3-phenylisoxazolin-5-yl)methoxy)-4-benzoic acid, 0.77 g (6.90 mmol) of cyclohexane 1,3-dione and 1.56 g (15.40 mmol) of triethylamine were stirred for 15 minutes at RT in 50 ml of methylene chloride. 1.81 g (6.90 mmol) of 2-chloro-N-methylpyridinium iodide were subsequently added and the mixture was stirred for 10 hours at RT. The reaction mixture was washed with water, dried over $Na_2SO_4$ and concentrated on a rotary evaporator. The crude product was chromatographed on silica gel with heptane/ethyl acetate, and 3-oxo-1-cyclohexenyl 2,4-dibromo-3-((3-phenylisoxazolin-5-yl)methoxy)benzoate was obtained as white solid.

Yield: 1.15 g (36% of theory); $R_f$(ethyl acetate): 0.82 $^1$H NMR: δ [CDCl3] 2.13(m, 2H), 2.45 (m, 2H), 2.68 (m, 2H), 3.56 (m, 2H), 3.69 (m, 2H), 3.28 (s, 3H), 4.20 (m, 2H), 5.23 (m, 1H), 6.05 (s, 1H), 7.43 (m, 3H), 7.49 (d, 1H), 7.63 (d, 1H), 7.72 (m, 2H).

Step 5: 2-((2,4-Dibromo-3-(3-phenylisoxazolin-5-yl)methoxy)-benzoyl)cyclohexane-1,3-dione 0.73 g (1.30 mmol) of 3-oxo-1-cyclohexenyl 2,4-dibromo-3-(3-phenylisoxazolin-5-yl)methoxy)benzoate were dissolved in 20 ml of acetonitrile. 3 drops of acetone cyanohydrin and 0.24 g (2.30 mmol) of triethylamine were added. The mixture was stirred for 2 hours at RT, whereupon 0.036 g (0.6 mmol) of potassium cyanide were added. After a further 10 hours at room temperature, the mixture was evaporated completely, and the residue was taken up in water and treated with 6 N hydrochloric acid. Then, the mixture was extracted with ethylene chloride. After the combined organic phases had been dried over $Na_2SO_4$ and evaporated completely, 2,4-dibromo-3-(3-phenylisoxazolin-5-yl)methoxy)cyclohexane-1,3-dione was obtained in the form of a yellow solid of melting point 59–65° C.

Yield: 0.57 g (71% of theory); $R_f$(ethyl acetate): 0.43 $^1$H NMR: δ [CDCl3] 2.03 (m, 2H), 2.42 (m, 2H), 2.76 (m, 2H), 3.58 (m, 2H), 4.20 (m, 2H), 5.19 (m, 1H), 6.80 (d, 1H), 7.42 (m, 3H), 7.54 (d, 1H), 7.69 (m, 2H).

3. Preparation of 4-(2-Chloro-3-((3-phenylisoxazol-5-yl)methoxy)-4-methylsulfonylbenzoyl)-1,3-dimethylpyrazolone Step 1: 2–Chloro-3-((3-phenylisoxazol-5-yl)methoxy)-4-methylsulfonylbenzoic Acid 1,3-dimethylpyrazol-5-one Enol Ester 0.50 g (1.20 mmol) of 2-chloro-3-((3-phenylisoxazol-5-yl)methoxy)-4-methylsulfonylbenzoic acid, 0.15 g (1.30 mmol) of 1,3-dimethylpyrazol-5-one, 0.26 g (1.30 mmol) of N'-(3-dimethylaminopropyl)-N-ethylcarbodiimide hydrochloride and 0.001 g of dimethylaminopyridine were stirred for 5 hours at room temperature in 10 ml of methylene chloride. The mixture was subsequently diluted with methylene chloride and washed with 0.5 N HCl, with water, with saturated $NaHCO_3$ solution and again with water. After the combined organic phases had been dried over $Na_2SO_4$ and evaporated completely on a rotary evaporator, the crude product was chromatographed on silica gel with heptane/ethyl acetate 8:2. This gave 2-chloro-3-((3-phenylisoxazol-5-yl)methoxy)-4-methylsulfonylbenzoic acid 1,3-dimethylpyrazol-5-one enol ester in the form of a brown resin.

Yield: 0.12 g (20% of theory); $^1$H NMR: δ [$CDCl_3$] 2.27 (s, 3H), 3.32 (s, 3H), 3.74 (s, 3H), 5.45 (s, 2H), 6.15 (s, 1H), 6.88 (s, 1H), 7.28 (m, 3H), 7.85 (m, 2H), 7.93 (d, 1H), 8.09 (d, 1H) $R_f$ (toluene/THF 7:3): 0.25.

Step 2: 4-(2-Chloro-((3-phenylisoxazol-5-yl)methoxy)-4-methyl-sulfonylbenzoyl)-1,3-dimethylpyrazolone 0.12 g (0.20 mmol) of 2-chloro-3-((3-phenylisoxazol-5-yl)methoxy)-4-methylsulfonylbenzoic acid 1,3-dimethylpyrazol-5-one enol ester was dissolved in 5 ml of acetonitrile. 2 drops of acetone cyanohydrin and 0.04 g (0.40 mmol) of triethylamine were added. The mixture was stirred for 2 hours at room temperature, whereupon 0.007 g (0.10 mmol) of potassium cyanide were added. After a further 10 hours at room temperature, the mixture was evaporated completely, and the residue was taken up in water and treated with 6 N hydrochloric acid. The mixture was subsequently extracted with methylene chloride. After the combined organic phases had been dried over Na$_2$SO$_4$ and evaporated completely on a rotary evaporator, the product was chromatographed on silica gel, which gave 4-(2-chloro-3-((3-phenylisoxazol-5-yl)methoxy)-4-methylsulfonylbenzoyl)-1,3-dimethylpyrazolone in the form of a pale brown resin.

Yield: 0.108 g (90% of theory) $^1$H NMR: δ [CDCl$_3$] 1.41 (s, 3H), 3.28 (s, 3H), 3.64 (s, 3H), 5.43 (s, 2H), 6.83 (s, 1H), 7.35 (s, 1H), 7.48 (m, 3H), 7.85 (m, 2H), 8.05 (d, 1H) R$_f$ (ethyl acetate): 0.03.

The examples listed in the tables hereinbelow were prepared analogously to the abovementioned methods or can be obtained analogously to the abovementioned methods.

The abbreviations used in this context mean:

| Et | = | ethyl | Me | = | methyl | Ph | = | phenyl |
|---|---|---|---|---|---|---|---|---|
| Pr | = | propyl | Py | = | pyridyl | c | = | cyclo |
| m.p. | = | melting point | RT | = | room temperature | | | |

TABLE 1

Compounds of the formula (I) according to the invention in which the substituents and symbols have the following meanings:

R$^1$ = 2-Cl  R$^2$ = 4-SO$_2$Me  R$^3$, R$^{19}$ to R$^{22}$ = H
Q = Q1a  X = OCH$_2$
v = 1  w = 2  Y, Z = CH$_2$

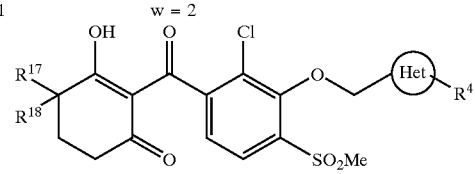

| No. | Het | R$^4$ | R$^{17}$, R$^{18}$ | Physical data |
|---|---|---|---|---|
| 1.1 | (isoxazoline) | c-Pr | H, H | m.p. 81–86° C. |
| 1.2 | (isoxazoline) | c-hexyl | H, H | Resin |
| 1.3 | (isoxazoline) | cyclopentenyl | H, H | |
| 1.4 | (isoxazoline) | CH$_2$O-c-Pr | H, H | |
| 1.5 | (isoxazoline) | CH$_2$O-c-hexyl | H, H | |
| 1.6 | (isoxazoline) | CH$_2$O-cyclopentenyl | H, H | |
| 1.7 | (isoxazoline) | Ph | H, H | m.p. 82–89° C. |
| 1.8 | (isoxazoline) | 2-CF$_3$—Ph | H, H | m.p. 80–86° C. |
| 1.9 | (isoxazoline) | 3-CF$_3$—Ph | H, H | Resin |

TABLE 1-continued

Compounds of the formula (I) according to the invention in which the substituents and symbols have the following meanings:

R¹ = 2-Cl    R² = 4-SO₂Me    R³, R¹⁹ to R²² = H
Q = Q1a      X = OCH₂         Y, Z = CH₂
v = 1        w = 2

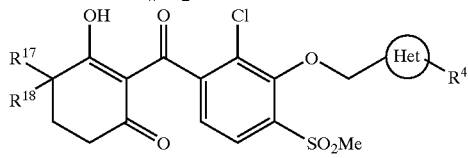

| No. | Het | R⁴ | R¹⁷, R¹⁸ | Physical data |
|---|---|---|---|---|
| 1.10 | (isoxazoline) | 4-CF₃—Ph | H, H | m.p. 100–106° C. |
| 1.11 | (isoxazoline) | 2-F—Ph | H, H | |
| 1.12 | (isoxazoline) | 3-F—Ph | H, H | |
| 1.13 | (isoxazoline) | 4-F—Ph | H, H | |
| 1.14 | (isoxazoline) | 4-NO₂—Ph | H, H | |
| 1.15 | (isoxazoline) | 3-MeO—Ph | H, H | |
| 1.16 | (isoxazoline) | CH₂O—Ph | H, H | |
| 1.17 | (isoxazoline) | CH₂O—Ph | Me, Me | |
| 1.18 | (isoxazoline) | CH₂O-(3-CF₃—Ph) | H, H | |
| 1.19 | (isoxazoline) | CH₂O-(3-F—Ph) | H, H | |
| 1.20 | (isoxazoline) | CH₂O-(4-NO₂—Ph) | H, H | |
| 1.21 | (isoxazoline) | CH₂O-(3-MeO—Ph) | H, H | |

TABLE 1-continued
Compounds of the formula (I) according to the invention in which the substituents and symbols have the following meanings:
$R^1$ = 2-Cl, $R^2$ = 4-SO$_2$Me, $R^3$, $R^{19}$ to $R^{22}$ = H
Q = Q1a, X = OCH$_2$, Y, Z = CH$_2$
v = 1, w = 2
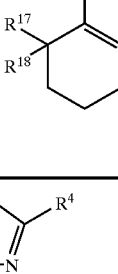
| No. | Het | R$^4$ | R$^{17}$, R$^{18}$ | Physical data |
|---|---|---|---|---|
| 1.22 | 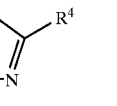 | 2-Py | H, H | Resin |
| 1.23 | 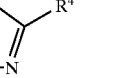 | 2-Py | Me, Me | |
| 1.24 | 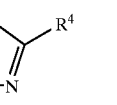 | 3-Py | H, H | |
| 1.25 | 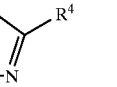 | 4-Py | H, H | Resin |
| 1.26 | 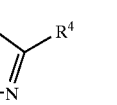 | CH$_2$O-(2-Py) | H, H | |
| 1.27 | 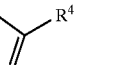 | CH$_2$O-(3-Py) | H, H | |
| 1.28 | 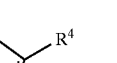 | CH$_2$O-(4-Py) | H, H | |
| 1.29 | 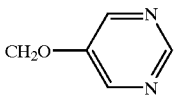 | 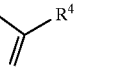 | H, H | |
| 1.30 | 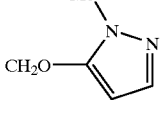 | 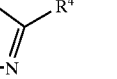 | H, H | |
| 1.31 | 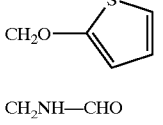 |  | H, H | Resin |
| 1.32 | 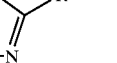 | CH$_2$NH—CHO | H, H | |
| 1.33 | 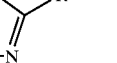 | CH$_2$NH—C(=O)Me | H, H | |

TABLE 1-continued

Compounds of the formula (I) according to the invention in which the substituents and symbols have the following meanings:

$R^1$ = 2-Cl, $R^2$ = 4-SO$_2$Me, $R^3$, $R^{19}$ to $R^{22}$ = H
Q = Q1a, X = OCH$_2$, Y, Z = CH$_2$
v = 1, w = 2

| No. | Het | R$^4$ | R$^{17}$, R$^{18}$ | Physical data |
|---|---|---|---|---|
| 1.34 | isoxazoline-R$^4$ | CH$_2$NH—C(=O)Me | Me, Me | |
| 1.35 | isoxazoline-R$^4$ | CH$_2$—NH—C(=O)-(tetrahydrofuran-2-yl) | H, H | |
| 1.36 | isoxazoline-R$^4$ | CH$_2$—NH—C(=O)-(2-Py) | H, H | |
| 1.37 | isoxazoline-R$^4$ | CH$_2$—NH—C(=O)—CF$_3$ | H, H | |
| 1.38 | isoxazoline-R$^4$ | CH$_2$—N(Me)—CHO | H, H | |
| 1.39 | isoxazoline-R$^4$ | CH$_2$—N(isoxazolidine) | H, H | |
| 1.40 | isoxazoline-R$^4$ | CH$_2$—NH—SO$_2$Me | H, H | |
| 1.41 | isoxazoline-R$^4$ | CH$_2$—NH—SO$_2$Et | H, H | |
| 1.42 | isoxazoline-R$^4$ | CH$_2$—NH—C(=O)—Ph | H, H | |
| 1.43 | isoxazoline-R$^4$ | CH$_2$—C(=O)—NH$_2$ | H, H | |
| 1.44 | isoxazoline-R$^4$ | CH$_2$—C(=O)—NHMe | H, H | |
| 1.45 | isoxazoline-R$^4$ | CH$_2$—C(=O)—NMe$_2$ | H, H | |

TABLE 1-continued

Compounds of the formula (I) according to the invention in which the substituents and symbols have the following meanings:

R$^1$ = 2-Cl  R$^2$ = 4-SO$_2$Me  R$^3$, R$^{19}$ to R$^{22}$ = H
Q = Q1a  X = OCH$_2$  Y, Z = CH$_2$
v = 1  w = 2

| No. | Het | R$^4$ | R$^{17}$, R$^{18}$ | Physical data |
|---|---|---|---|---|
| 1.46 | 4,5-dihydroisoxazol-3-yl | CH$_2$—C(=O)—NMe$_2$ | Me, Me | |
| 1.47 | 4,5-dihydroisoxazol-3-yl | CH$_2$—C(=O)—N(pyrrolidinyl) | H, H | |
| 1.48 | 4,5-dihydroisoxazol-3-yl | CH$_2$—C(=O)—NH—OMe | H, H | |
| 1.49 | 4,5-dihydroisoxazol-3-yl | CH$_2$-(2-Py) | H, H | |
| 1.50 | 4,5-dihydroisoxazol-3-yl | CH$_2$-(3-Py) | H, H | |
| 1.51 | 4,5-dihydroisoxazol-3-yl | CH$_2$-(4-Py) | H, H | |
| 1.52 | 4,5-dihydroisoxazol-3-yl | CH$_2$-(2-furyl) | H, H | |
| 1.53 | 4,5-dihydroisoxazol-3-yl | CH$_2$-(1-pyrrolyl) | H, H | |
| 1.54 | 4,5-dihydroisoxazol-3-yl | CH$_2$-(1-pyrazolyl) | H, H | |
| 1.55 | 4,5-dihydroisoxazol-3-yl | CH$_2$-(2-oxopyrrolidin-1-yl) | H, H | Resin |
| 1.56 | 4,5-dihydroisoxazol-3-yl | 2-tetrahydrofuranyl | H, H | |

TABLE 1-continued

Compounds of the formula (I) according to the invention in which the substituents and symbols have the following meanings:

$R^1$ = 2-Cl, $R^2$ = 4-SO$_2$Me, $R^3$, $R^{19}$ to $R^{22}$ = H
Q = Q1a, X = OCH$_2$, Y, Z = CH$_2$
v = 1, w = 2

| No. | Het | R$^4$ | R$^{17}$, R$^{18}$ | Physical data |
|---|---|---|---|---|
| 1.57 | isoxazoline | 2-oxopyrrolidin-1-yl | H, H | |
| 1.58 | isoxazoline | 2-oxopyrrolidin-1-yl | Me, Me | |
| 1.59 | isoxazoline | imidazol-1-yl | H, H | |
| 1.60 | isoxazoline | pyrrolidin-1-yl | H, H | |
| 1.61 | isoxazoline | piperidin-1-yl | H, H | |
| 1.62 | isoxazoline | morpholin-4-yl | H, H | |
| 1.63 | isoxazoline | CH$_2$—PO(Me)(Et) | H, H | |
| 1.64 | isoxazole | c-Pr | H, H | Resin |
| 1.65 | isoxazole | c-hexyl | H, H | |
| 1.66 | isoxazole | cyclopentenyl | H, H | |
| 1.67 | isoxazole | CH$_2$O-c-Pr | H, H | |

TABLE 1-continued

Compounds of the formula (I) according to the invention in which the substituents and symbols have the following meanings:

R¹ = 2-Cl, R² = 4-SO₂Me, R³, R¹⁹ to R²² = H
Q = Q1a, X = OCH₂, Y, Z = CH₂
v = 1, w = 2

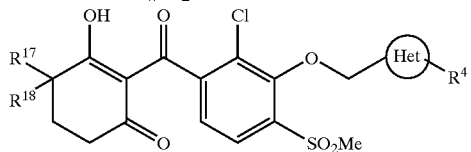

| No. | Het | R⁴ | R¹⁷, R¹⁸ | Physical data |
|---|---|---|---|---|
| 1.68 | isoxazole | CH₂O-c-hexyl | H, H | |
| 1.69 | isoxazole | CH₂O-cyclopentenyl | H, H | |
| 1.70 | isoxazole | Ph | H, H | m.p. 72–78° C. |
| 1.71 | isoxazole | 2-CF₃—Ph | H, H | Resin |
| 1.72 | isoxazole | 3-CF₃—Ph | H, H | m.p. 80–90° C. |
| 1.73 | isoxazole | 4-CF₃—Ph | H, H | Resin |
| 1.74 | isoxazole | 2-F—Ph | H, H | |
| 1.75 | isoxazole | 3-F—Ph | H, H | |
| 1.76 | isoxazole | 4-F—Ph | H, H | |
| 1.77 | isoxazole | 4-NO₂—Ph | H, H | |
| 1.78 | isoxazole | 3-MeO—Ph | H, H | |
| 1.79 | isoxazole | CH₂O—Ph | H, H | |

TABLE 1-continued

Compounds of the formula (I) according to the invention in which the substituents and symbols have the following meanings:

$R^1$ = 2-Cl, $R^2$ = 4-SO$_2$Me, $R^3$, $R^{19}$ to $R^{22}$ = H
Q = Q1a, X = OCH$_2$, Y, Z = CH$_2$
v = 1, w = 2

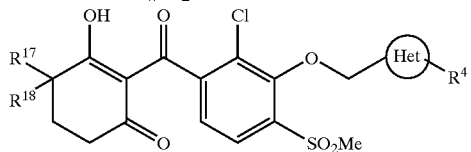

| No. | Het | R$^4$ | R$^{17}$, R$^{18}$ | Physical data |
|---|---|---|---|---|
| 1.80 | isoxazole | CH$_2$O—Ph | Me, Me | |
| 1.81 | isoxazole | CH$_2$O-(3-CF$_3$—Ph) | H, H | |
| 1.82 | isoxazole | CH$_2$O-(3-F—Ph) | H, H | |
| 1.83 | isoxazole | CH$_2$O-(4-NO$_2$—Ph) | H, H | |
| 1.84 | isoxazole | CH$_2$O-(3-MeO—Ph) | H, H | |
| 1.85 | isoxazole | 2-Py | H, H | Resin |
| 1.86 | isoxazole | 2-Py | Me, Me | |
| 1.87 | isoxazole | 3-Py | H, H | |
| 1.88 | isoxazole | 4-Py | H, H | |
| 1.89 | isoxazole | CH$_2$O-(2-Py) | H, H | |
| 1.90 | isoxazole | CH$_2$O-(3-Py) | H, H | |
| 1.91 | isoxazole | CH$_2$O-(4-Py) | H, H | |

TABLE 1-continued

Compounds of the formula (I) according to the invention in which the substituents and symbols have the following meanings:

| $R^1$ = 2-Cl | $R^2$ = 4-SO$_2$Me | $R^3$, $R^{19}$ to $R^{22}$ = H |
| Q = Q1a | X = OCH$_2$ | Y, Z = CH$_2$ |
| v = 1 | w = 2 | |

| No. | Het | $R^4$ | $R^{17}$, $R^{18}$ | Physical data |
|---|---|---|---|---|
| 1.92 | isoxazole-$R^4$ | CH$_2$O-pyrimidine | H, H | |
| 1.93 | isoxazole-$R^4$ | CH$_2$O-(N-Me-pyrazole) | H, H | |
| 1.94 | isoxazole-$R^4$ | CH$_2$O-thiophene | H, H | |
| 1.95 | isoxazole-$R^4$ | CH$_2$NH—CHO | H, H | |
| 1.96 | isoxazole-$R^4$ | CH$_2$NH—C(=O)Me | H, H | |
| 1.97 | isoxazole-$R^4$ | CH$_2$NH—C(=O)Me | Me, Me | |
| 1.98 | isoxazole-$R^4$ | CH$_2$—NH—C(=O)-(tetrahydrofuran-2-yl) | H, H | |
| 1.99 | isoxazole-$R^4$ | CH$_2$—NH—C(=O)-(2-Py) | H, H | |
| 1.100 | isoxazole-$R^4$ | CH$_2$—NH—C(=O)—CF$_3$ | H, H | |
| 1.101 | isoxazole-$R^4$ | CH$_2$—N(Me)—CHO | H, H | |
| 1.102 | isoxazole-$R^4$ | CH$_2$—N(isoxazolidine) | H, H | |

TABLE 1-continued

Compounds of the formula (I) according to the invention in which the substituents and symbols have the following meanings:

R¹ = 2-Cl, Q = Q1a, v = 1, R² = 4-SO₂Me, X = OCH₂, w = 2, R³, R¹⁹ to R²² = H, Y, Z = CH₂

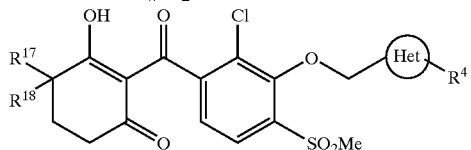

| No. | Het | R⁴ | R¹⁷, R¹⁸ | Physical data |
|---|---|---|---|---|
| 1.103 | isoxazole | CH₂—NH—SO₂Me | H, H | |
| 1.104 | isoxazole | CH₂—NH—SO₂Et | H, H | |
| 1.105 | isoxazole | CH₂—NH—C(=O)—Ph | H, H | |
| 1.106 | isoxazole | CH₂—C(=O)—NH₂ | H, H | |
| 1.107 | isoxazole | CH₂—C(=O)—NHMe | H, H | |
| 1.108 | isoxazole | CH₂—C(=O)—NMe₂ | H, H | |
| 1.109 | isoxazole | CH₂—C(=O)—NMe₂ | Me, Me | |
| 1.110 | isoxazole | CH₂—C(=O)—N-pyrrolidinyl | H, H | Resin |
| 1.111 | isoxazole | CH₂—C(=O)—NH—OMe | H, H | |
| 1.112 | isoxazole | CH₂-(2-Py) | H, H | Resin |
| 1.113 | isoxazole | CH₂-(3-Py) | H, H | |
| 1.114 | isoxazole | CH₂-(4-Py) | H, H | |

TABLE 1-continued

Compounds of the formula (I) according to the invention in which the substituents and symbols have the following meanings:

$R^1 = 2\text{-Cl}$     $R^2 = 4\text{-SO}_2\text{Me}$     $R^3$, $R^{19}$ to $R^{22} = H$
$Q = Q1a$     $X = \text{OCH}_2$     $Y, Z = \text{CH}_2$
$v = 1$     $w = 2$

| No. | Het | $R^4$ | $R^{17}$, $R^{18}$ | Physical data |
|---|---|---|---|---|
| 1.115 | isoxazolyl-R⁴ | CH₂-(2-furanyl) | H, H | |
| 1.116 | isoxazolyl-R⁴ | CH₂-(1-pyrrolyl) | H, H | |
| 1.117 | isoxazolyl-R⁴ | CH₂-(1-pyrazolyl) | H, H | |
| 1.118 | isoxazolyl-R⁴ | CH₂-(2-oxopyrrolidin-1-yl) | H, H | |
| 1.119 | isoxazolyl-R⁴ | 2-tetrahydrofuranyl | H, H | |
| 1.120 | isoxazolyl-R⁴ | (2-oxopyrrolidin-1-yl) | H, H | |
| 1.121 | isoxazolyl-R⁴ | (2-oxopyrrolidin-1-yl) | Me, Me | |
| 1.122 | isoxazolyl-R⁴ | (1-imidazolyl) | H, H | |
| 1.123 | isoxazolyl-R⁴ | (1-pyrrolidinyl) | H, H | |
| 1.124 | isoxazolyl-R⁴ | (1-piperidinyl) | H, H | |
| 1.125 | isoxazolyl-R⁴ | (4-morpholinyl) | H, H | |

TABLE 1-continued

Compounds of the formula (I) according to the invention in which the substituents and symbols have the following meanings:

$R^1$ = 2-Cl, $R^2$ = 4-SO$_2$Me, $R^3$, $R^{19}$ to $R^{22}$ = H
Q = Q1a, X = OCH$_2$, Y, Z = CH$_2$
v = 1, w = 2

| No. | Het | R$^4$ | R$^{17}$, R$^{18}$ | Physical data |
|---|---|---|---|---|
| 1.126 | isoxazole (O—N) | CH$_2$—PO(Me)(Et) | H, H | |
| 1.127 | isoxazoline (N—O) | c-Pr | H, H | |
| 1.128 | isoxazoline (N—O) | c-hexyl | H, H | |
| 1.129 | isoxazoline (N—O) | cyclopentenyl | H, H | |
| 1.130 | isoxazoline (N—O) | CH$_2$O-c-Pr | H, H | |
| 1.131 | isoxazoline (N—O) | CH$_2$O-c-hexyl | H, H | |
| 1.132 | isoxazoline (N—O) | CH$_2$O-cyclopentenyl | H, H | |
| 1.133 | isoxazoline (N—O) | Ph | H, H | |
| 1.134 | isoxazoline (N—O) | 2-CF$_3$—Ph | H, H | |
| 1.135 | isoxazoline (N—O) | 3-CF$_3$—Ph | H, H | |
| 1.136 | isoxazoline (N—O) | 4-CF$_3$—Ph | H, H | |
| 1.137 | isoxazoline (N—O) | 2-F—Ph | H, H | |

TABLE 1-continued

Compounds of the formula (I) according to the invention in which the substituents and symbols have the following meanings:

$R^1$ = 2-Cl, $R^2$ = 4-SO$_2$Me, $R^3$, $R^{19}$ to $R^{22}$ = H
Q = Q1a, X = OCH$_2$, Y, Z = CH$_2$
v = 1, w = 2

| No. | Het | R$^4$ | R$^{17}$, R$^{18}$ | Physical data |
|---|---|---|---|---|
| 1.138 | 4,5-dihydroisoxazol-3,5-diyl | 3-F—Ph | H, H | |
| 1.139 | 4,5-dihydroisoxazol-3,5-diyl | 4-F—Ph | H, H | |
| 1.140 | 4,5-dihydroisoxazol-3,5-diyl | 4-NO$_2$—Ph | H, H | |
| 1.141 | 4,5-dihydroisoxazol-3,5-diyl | 3-MeO—Ph | H, H | |
| 1.142 | 4,5-dihydroisoxazol-3,5-diyl | CH$_2$O—Ph | H, H | |
| 1.143 | 4,5-dihydroisoxazol-3,5-diyl | CH$_2$O—Ph | Me, Me | |
| 1.144 | 4,5-dihydroisoxazol-3,5-diyl | CH$_2$O-(3-CF$_3$—Ph) | H, H | |
| 1.145 | 4,5-dihydroisoxazol-3,5-diyl | CH$_2$O-(3-F—Ph) | H, H | |
| 1.146 | 4,5-dihydroisoxazol-3,5-diyl | CH$_2$O-(4-NO$_2$—Ph) | H, H | |
| 1.147 | 4,5-dihydroisoxazol-3,5-diyl | CH$_2$O-(3-MeO—Ph) | H, H | |
| 1.148 | 4,5-dihydroisoxazol-3,5-diyl | 2-Py | H, H | |
| 1.149 | 4,5-dihydroisoxazol-3,5-diyl | 2-Py | Me, Me | |

TABLE 1-continued

Compounds of the formula (I) according to the invention in which the substituents and symbols have the following meanings:

R¹ = 2-Cl, R² = 4-SO₂Me, R³, R¹⁹ to R²² = H
Q = Q1a, X = OCH₂, Y, Z = CH₂
v = 1, w = 2

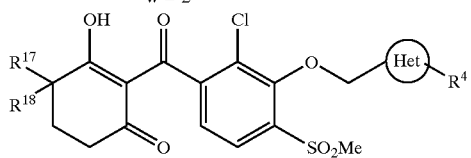

| No. | Het | R⁴ | R¹⁷, R¹⁸ | Physical data |
|---|---|---|---|---|
| 1.150 | isoxazoline | 3-Py | H, H | |
| 1.151 | isoxazoline | 4-Py | H, H | |
| 1.152 | isoxazoline | CH₂O-(2-Py) | H, H | |
| 1.153 | isoxazoline | CH₂O-(3-Py) | H, H | |
| 1.154 | isoxazoline | CH₂O-(4-Py) | H, H | |
| 1.155 | isoxazoline | CH₂O-(5-pyrimidinyl) | H, H | |
| 1.156 | isoxazoline | CH₂O-(1-Me-pyrazol-5-yl) | H, H | |
| 1.157 | isoxazoline | CH₂O-(2-thienyl) | H, H | |
| 1.158 | isoxazoline | CH₂NH—CHO | H, H | |
| 1.159 | isoxazoline | CH₂NH—C(=O)Me | H, H | |
| 1.160 | isoxazoline | CH₂NH—C(=O)Me | Me, Me | |

TABLE 1-continued

Compounds of the formula (I) according to the invention in which the substituents and symbols have the following meanings:

$R^1$ = 2-Cl $\quad R^2$ = 4-SO$_2$Me $\quad R^3$, $R^{19}$ to $R^{22}$ = H
Q = Q1a $\quad X$ = OCH$_2$ $\quad Y$, Z = CH$_2$
v = 1 $\quad w$ = 2

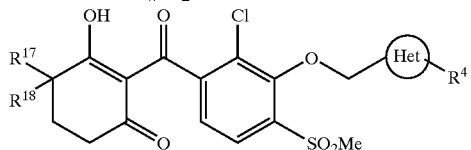

| No. | Het | $R^4$ | $R^{17}$, $R^{18}$ | Physical data |
|---|---|---|---|---|
| 1.161 | isoxazoline-R$^4$ | CH$_2$—NH—C(=O)-(tetrahydrofuran-2-yl) | H, H | |
| 1.162 | isoxazoline-R$^4$ | CH$_2$—NH—C(=O)-(2-Py) | H, H | |
| 1.163 | isoxazoline-R$^4$ | CH$_2$—NH—C(=O)—CF$_3$ | H, H | |
| 1.164 | isoxazoline-R$^4$ | CH$_2$—N(Me)—CHO | H, H | |
| 1.165 | isoxazoline-R$^4$ | CH$_2$—N(isoxazolidine) | H, H | |
| 1.166 | isoxazoline-R$^4$ | CH$_2$—NH—SO$_2$Me | H, H | |
| 1.167 | isoxazoline-R$^4$ | CH$_2$—NH—SO$_2$Et | H, H | |
| 1.168 | isoxazoline-R$^4$ | CH$_2$—NH—C(=O)—Ph | H, H | |
| 1.169 | isoxazoline-R$^4$ | CH$_2$—C(=O)—NH$_2$ | H, H | |
| 1.170 | isoxazoline-R$^4$ | CH$_2$—C(=O)—NHMe | H, H | |
| 1.171 | isoxazoline-R$^4$ | CH$_2$—C(=O)—NMe$_2$ | H, H | |
| 1.172 | isoxazoline-R$^4$ | CH$_2$—C(=O)—NMe$_2$ | Me, Me | |

TABLE 1-continued

Compounds of the formula (I) according to the invention in which the substituents and symbols have the following meanings:
R¹ = 2-Cl, R² = 4-SO₂Me, R³, R¹⁹ to R²² = H
Q = Q1a, X = OCH₂, Y, Z = CH₂
v = 1, w = 2

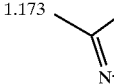

| No. | Het | R⁴ | R¹⁷, R¹⁸ | Physical data |
|---|---|---|---|---|
| 1.173 | isoxazoline-R⁴ | CH₂—C(=O)—N(pyrrolidine) | H, H | |
| 1.174 | isoxazoline-R⁴ | CH₂—C(=O)—NH—OMe | H, H | |
| 1.175 | isoxazoline-R⁴ | CH₂-(2-Py) | H, H | |
| 1.176 | isoxazoline-R⁴ | CH₂-(3-Py) | H, H | |
| 1.177 | isoxazoline-R⁴ | CH₂-(4-Py) | H, H | |
| 1.178 | isoxazoline-R⁴ | CH₂-(2-furyl) | H, H | |
| 1.179 | isoxazoline-R⁴ | CH₂—N(pyrrole) | H, H | |
| 1.180 | isoxazoline-R⁴ | CH₂—N(pyrazole) | H, H | |
| 1.181 | isoxazoline-R⁴ | CH₂—N(2-pyrrolidinone) | H, H | |
| 1.182 | isoxazoline-R⁴ | 2-tetrahydrofuranyl | H, H | |
| 1.183 | isoxazoline-R⁴ | N(2-pyrrolidinone) | H, H | |

TABLE 1-continued

Compounds of the formula (I) according to the invention in which the substituents and symbols have the following meanings:

$R^1$ = 2-Cl $\quad$ $R^2$ = 4-SO$_2$Me $\quad$ $R^3$, $R^{19}$ to $R^{22}$ = H
Q = Q1a $\quad$ X = OCH$_2$ $\quad$ Y, Z = CH$_2$
v = 1 $\quad$ w = 2

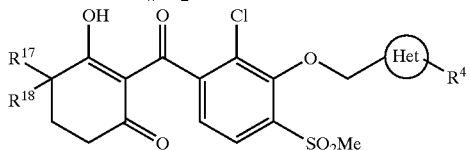

| No. | Het | $R^4$ | $R^{17}$, $R^{18}$ | Physical data |
|---|---|---|---|---|
| 1.184 | isoxazoline-R⁴ | N-pyrrolidinonyl | Me, Me | |
| 1.185 | isoxazoline-R⁴ | N-imidazolyl | H, H | |
| 1.186 | isoxazoline-R⁴ | N-pyrrolidinyl | H, H | |
| 1.187 | isoxazoline-R⁴ | N-piperidinyl | H, H | |
| 1.188 | isoxazoline-R⁴ | N-morpholinyl | H, H | |
| 1.189 | isoxazoline-R⁴ | CH$_2$—PO(Me)(Et) | H, H | |
| 1.190 | isoxazoline-R⁴ | c-Pr | H, H | |
| 1.191 | isoxazoline-R⁴ | c-hexyl | H, H | |
| 1.192 | isoxazoline-R⁴ | cyclopentenyl-CH$_2$ | H, H | |
| 1.193 | isoxazoline-R⁴ | CH$_2$O-c-Pr | H, H | |
| 1.194 | isoxazoline-R⁴ | CH$_2$O-c-hexyl | H, H | |
| 1.195 | isoxazoline-R⁴ | CH$_2$O-cyclopentenyl | H, H | |

TABLE 1-continued

Compounds of the formula (I) according to the invention in which the substituents and symbols have the following meanings:

R¹ = 2-Cl, Q = Q1a, v = 1, R² = 4-SO₂Me, X = OCH₂, w = 2, R³, R¹⁹ to R²² = H, Y, Z = CH₂

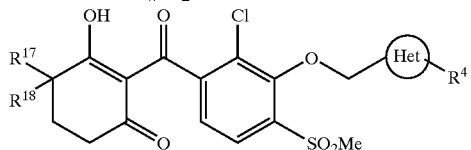

| No. | Het | R⁴ | R¹⁷, R¹⁸ | Physical data |
|-----|-----|-----|----------|---------------|
| 1.196 | isoxazole (3,5) | Ph | H, H | |
| 1.197 | isoxazole (3,5) | 2-CF₃—Ph | H, H | |
| 1.198 | isoxazole (3,5) | 3-CF₃—Ph | H, H | |
| 1.199 | isoxazole (3,5) | 4-CF₃—Ph | H, H | |
| 1.200 | isoxazole (3,5) | 2-F—Ph | H, H | |
| 1.201 | isoxazole (3,5) | 3-F—Ph | H, H | |
| 1.202 | isoxazole (3,5) | 4-F—Ph | H, H | |
| 1.203 | isoxazole (3,5) | 4-NO₂—Ph | H, H | |
| 1.204 | isoxazole (3,5) | 3-MeO—Ph | H, H | |
| 1.205 | isoxazole (3,5) | CH₂O—Ph | H, H | |
| 1.206 | isoxazole (3,5) | CH₂O—Ph | Me, Me | |
| 1.207 | isoxazole (3,5) | CH₂O-(3-CF₃—Ph) | H, H | |

TABLE 1-continued

Compounds of the formula (I) according to the invention in which the substituents and symbols have the following meanings:

R¹ = 2-Cl, R² = 4-SO₂Me, R³, R¹⁹ to R²² = H
Q = Q1a, X = OCH₂, Y, Z = CH₂
v = 1, w = 2

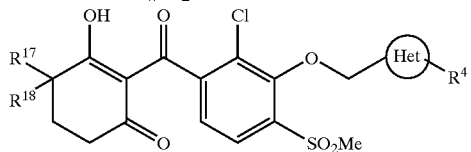

| No. | Het | R⁴ | R¹⁷, R¹⁸ | Physical data |
|---|---|---|---|---|
| 1.208 | 3-isoxazolyl-R⁴ | CH₂O-(3-F—Ph) | H, H | |
| 1.209 | 3-isoxazolyl-R⁴ | CH₂O-(4-NO₂—Ph) | H, H | |
| 1.210 | 3-isoxazolyl-R⁴ | CH₂O-(3-MeO—Ph) | H, H | |
| 1.211 | 3-isoxazolyl-R⁴ | 2-Py | H, H | |
| 1.212 | 3-isoxazolyl-R⁴ | 2-Py | Me, Me | |
| 1.213 | 3-isoxazolyl-R⁴ | 3-Py | H, H | |
| 1.214 | 3-isoxazolyl-R⁴ | 4-Py | H, H | |
| 1.215 | 3-isoxazolyl-R⁴ | CH₂O-(2-Py) | H, H | |
| 1.216 | 3-isoxazolyl-R⁴ | CH₂O-(3-Py) | H, H | |
| 1.217 | 3-isoxazolyl-R⁴ | CH₂O-(4-Py) | H, H | |
| 1.218 | 3-isoxazolyl-R⁴ | CH₂O-(5-pyrimidinyl) | H, H | |
| 1.219 | 3-isoxazolyl-R⁴ | CH₂O-(1-Me-pyrazol-5-yl) | H, H | |

TABLE 1-continued

Compounds of the formula (I) according to the invention in which the substituents and symbols have the following meanings:

$R^1$ = 2-Cl, $R^2$ = 4-SO$_2$Me, $R^3$, $R^{19}$ to $R^{22}$ = H
Q = Q1a, X = OCH$_2$, Y, Z = CH$_2$
v = 1, w = 2

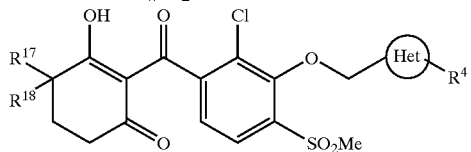

| No. | Het | R$^4$ | R$^{17}$, R$^{18}$ | Physical data |
|---|---|---|---|---|
| 1.220 | isoxazole-R$^4$ | CH$_2$O-(2-thienyl) | H, H | |
| 1.221 | isoxazole-R$^4$ | CH$_2$NH—CHO | H, H | |
| 1.222 | isoxazole-R$^4$ | CH$_2$NH—C(=O)Me | H, H | |
| 1.223 | isoxazole-R$^4$ | CH$_2$NH—C(=O)Me | Me, Me | |
| 1.224 | isoxazole-R$^4$ | CH$_2$—NH—C(=O)-(tetrahydrofuran-2-yl) | H, H | |
| 1.225 | isoxazole-R$^4$ | CH$_2$—NH—C(=O)-(2-Py) | H, H | |
| 1.226 | isoxazole-R$^4$ | CH$_2$—NH—C(=O)—CF$_3$ | H, H | |
| 1.227 | isoxazole-R$^4$ | CH$_2$—N(Me)—CHO | H, H | |
| 1.228 | isoxazole-R$^4$ | CH$_2$-(isoxazolidin-2-yl) | H, H | |
| 1.229 | isoxazole-R$^4$ | CH$_2$—NH—SO$_2$Me | H, H | |
| 1.230 | isoxazole-R$^4$ | CH$_2$—NH—SO$_2$Et | H, H | |
| 1.231 | isoxazole-R$^4$ | CH$_2$—NH—C(=O)—Ph | H, H | |

TABLE 1-continued

Compounds of the formula (I) according to the invention in which the substituents and symbols have the following meanings:
$R^1$ = 2-Cl, $R^2$ = 4-SO$_2$Me, $R^3$, $R^{19}$ to $R^{22}$ = H
Q = Q1a, X = OCH$_2$, Y, Z = CH$_2$
v = 1, w = 2

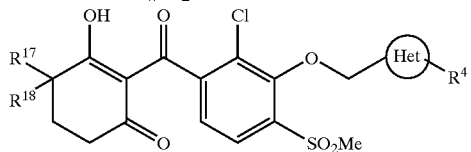

| No. | Het | R$^4$ | R$^{17}$, R$^{18}$ | Physical data |
|---|---|---|---|---|
| 1.232 | 3-methylisoxazol-5-yl | CH$_2$—C(=O)—NH$_2$ | H, H | |
| 1.233 | 3-methylisoxazol-5-yl | CH$_2$—C(=O)—NHMe | H, H | |
| 1.234 | 3-methylisoxazol-5-yl | CH$_2$—C(=O)—NMe$_2$ | H, H | |
| 1.235 | 3-methylisoxazol-5-yl | CH$_2$—C(=O)—NMe$_2$ | Me, Me | |
| 1.236 | 3-methylisoxazol-5-yl | CH$_2$—C(=O)-pyrrolidin-1-yl | H, H | |
| 1.237 | 3-methylisoxazol-5-yl | CH$_2$—C(=O)—NH—OMe | H, H | |
| 1.238 | 3-methylisoxazol-5-yl | CH$_2$-(2-Py) | H, H | |
| 1.239 | 3-methylisoxazol-5-yl | CH$_2$-(3-Py) | H, H | |
| 1.240 | 3-methylisoxazol-5-yl | CH$_2$-(4-Py) | H, H | |
| 1.241 | 3-methylisoxazol-5-yl | CH$_2$-(2-furyl) | H, H | |
| 1.242 | 3-methylisoxazol-5-yl | CH$_2$-(pyrrol-1-yl) | H, H | |
| 1.243 | 3-methylisoxazol-5-yl | CH$_2$-(pyrazol-1-yl) | H, H | |

TABLE 1-continued

Compounds of the formula (I) according to the invention in which the substituents and symbols have the following meanings:

$R^1$ = 2-Cl, $R^2$ = 4-$SO_2$Me, $R^3$, $R^{19}$ to $R^{22}$ = H
Q = Q1a, X = $OCH_2$, Y, Z = $CH_2$
v = 1, w = 2

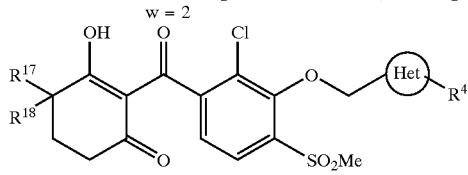

| No. | Het | $R^4$ | $R^{17}$, $R^{18}$ | Physical data |
|---|---|---|---|---|
| 1.244 | 3-isoxazolyl-$R^4$ | $CH_2$—N-pyrrolidinone | H, H | |
| 1.245 | 3-isoxazolyl-$R^4$ | 2-tetrahydrofuranyl | H, H | |
| 1.246 | 3-isoxazolyl-$R^4$ | N-pyrrolidinone | H, H | |
| 1.247 | 3-isoxazolyl-$R^4$ | N-pyrrolidinone | Me, Me | |
| 1.248 | 3-isoxazolyl-$R^4$ | N-imidazolyl | H, H | |
| 1.249 | 3-isoxazolyl-$R^4$ | N-pyrrolidinyl | H, H | |
| 1.250 | 3-isoxazolyl-$R^4$ | N-piperidinyl | H, H | |
| 1.251 | 3-isoxazolyl-$R^4$ | N-morpholinyl | H, H | |
| 1.252 | 3-isoxazolyl-$R^4$ | $CH_2$—PO(Me)(Et) | H, H | |
| 1.253 | 1,2,4-oxadiazolyl-$R^4$ | Ph | H, H | |
| 1.254 | 1,2,4-oxadiazolyl-$R^4$ | Ph | Me, Me | |

TABLE 1-continued

Compounds of the formula (I) according to the invention in which the substituents and symbols have the following meanings:

$R^1$ = 2-Cl $\quad$ $R^2$ = 4-SO$_2$Me $\quad$ $R^3$, $R^{19}$ to $R^{22}$ = H
Q = Q1a $\quad$ X = OCH$_2$ $\quad$ Y, Z = CH$_2$
v = 1 $\quad$ w = 2

| No. | Het | R$^4$ | R$^{17}$, R$^{18}$ | Physical data |
|---|---|---|---|---|
| 1.255 | 1,2,4-oxadiazol-3,5-diyl (N–O) | 3-F—Ph | H, H | |
| 1.256 | 1,2,4-oxadiazol-3,5-diyl (N–O) | CH$_2$—Ph | H, H | |
| 1.257 | 1,2,4-oxadiazol-3,5-diyl (N–O) | CH$_2$-(3-Me—Ph) | H, H | |
| 1.258 | 1,2,4-oxadiazol-5,3-diyl (O–N) | Ph | H, H | |
| 1.259 | 1,2,4-oxadiazol-5,3-diyl (O–N) | Ph | Me, Me | |
| 1.260 | 1,2,4-oxadiazol-5,3-diyl (O–N) | 3-F—Ph | H, H | |
| 1.261 | 1,2,4-oxadiazol-5,3-diyl (O–N) | CH$_2$—Ph | H, H | |
| 1.262 | 1,2,4-oxadiazol-5,3-diyl (O–N) | CH$_2$-(3-Me—Ph) | H, H | |
| 1.263 | 1,3,4-oxadiazol-2,5-diyl (N–N) | Ph | H, H | |
| 1.264 | 1,3,4-oxadiazol-2,5-diyl (N–N) | Ph | Me, Me | |
| 1.265 | 1,3,4-oxadiazol-2,5-diyl (N–N) | 3-F—Ph | H, H | |
| 1.266 | 1,3,4-oxadiazol-2,5-diyl (N–N) | CH$_2$—Ph | H, H | |

TABLE 1-continued

Compounds of the formula (I) according to the invention in which the substituents and symbols have the following meanings:

$R^1$ = 2-Cl  $R^2$ = 4-SO$_2$Me  $R^3$, $R^{19}$ to $R^{22}$ = H
Q = Q1a  X = OCH$_2$  Y, Z = CH$_2$
v = 1  w = 2

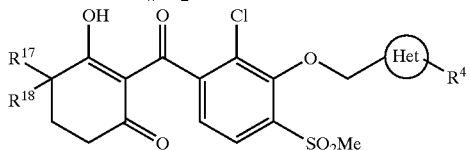

| No. | Het | R$^4$ | R$^{17}$, R$^{18}$ | Physical data |
|---|---|---|---|---|
| 1.267 | 2,5-oxadiazole | CH$_2$-(3-Me—Ph) | H, H | |
| 1.268 | 2,5-oxazole (N at 3) | Ph | H, H | |
| 1.269 | 2,5-oxazole (N at 3) | Ph | Me, Me | |
| 1.270 | 2,5-oxazole (N at 3) | 3-F—Ph | H, H | |
| 1.271 | 2,5-oxazole (N at 3) | CH$_2$—Ph | H, H | |
| 1.272 | 2,5-oxazole (N at 3) | CH$_2$-(3-Me—Ph) | H, H | |
| 1.273 | 2,5-oxazole (N at 4) | Ph | H, H | |
| 1.274 | 2,5-oxazole (N at 4) | Ph | Me, Me | |
| 1.275 | 2,5-oxazole (N at 4) | 3-F—Ph | H, H | |
| 1.276 | 2,5-oxazole (N at 4) | CH$_2$—Ph | H, H | |
| 1.277 | 2,5-oxazole (N at 4) | CH$_2$-(3-Me-Ph) | H, H | |
| 1.278 | 2,5-thiazole | Ph | H, H | |

TABLE 1-continued
Compounds of the formula (I) according to the invention in which the substituents and symbols have the following meanings:
$R^1$ = 2-Cl  $R^2$ = 4-SO$_2$Me  $R^3$, $R^{19}$ to $R^{22}$ = H
Q = Q1a  X = OCH$_2$  Y, Z = CH$_2$
v = 1  w = 2
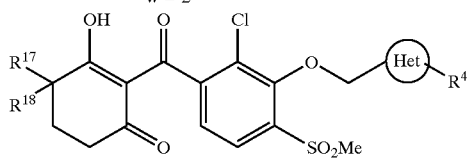
| No. | Het | $R^4$ | $R^{17}$, $R^{18}$ | Physical data |
|---|---|---|---|---|
| 1.279 |  | Ph | Me, Me | |
| 1.280 |  | 3-F—Ph | H, H | |
| 1.281 |  | CH$_2$—Ph | H, H | |
| 1.282 |  | CH$_2$-(3-Me—Ph) | H, H | |
| 1.283 |  | Ph | H, H | |
| 1.284 |  | Ph | Me, Me | |
| 1.285 |  | 3-F—Ph | H, H | |
| 1.286 |  | CH$_2$—Ph | H, H | |
| 1.287 |  | CH$_2$-(3-Me—Ph) | H, H | |
| 1.288 |  | — | H, H | Resin |
| 1.289 |  | — | Me, Me | |

TABLE 1-continued

Compounds of the formula (I) according to the invention in which the substituents and symbols have the following meanings:

$R^1 = 2\text{-Cl}$  $R^2 = 4\text{-SO}_2\text{Me}$  $R^3, R^{19}$ to $R^{22} = H$
$Q = Q1a$  $X = OCH_2$  $Y, Z = CH_2$
$v = 1$  $w = 2$

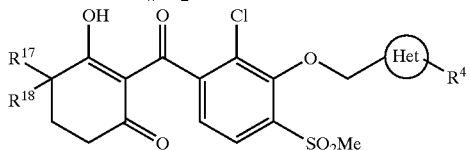

| No. | Het | $R^4$ | $R^{17}, R^{18}$ | Physical data |
|---|---|---|---|---|
| 1.290 | (2-methyl-5,6,7,8-tetrahydroquinoline) | — | H, H | |
| 1.291 | (2-methylbenzoxazole) | — | H, H | |
| 1.292 | (2-methylbenzothiazole) | — | H, H | |

TABLE 2

Compounds of the formula (I) according to the invention in which the substituents and symbols have the following meanings:

$R^1 =$ 2-Cl  $R^2 =$ 4-SO$_2$Me  $R^3 =$ H  $R^9 =$ H
$Q =$ Q2  $X =$ OCH$_2$  $K =$ 0 or 1

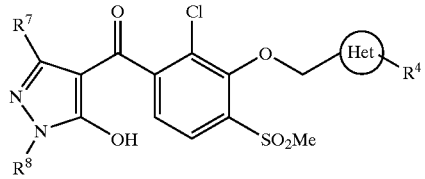

| No. | Het | $R^4$ | $R^7$ | $R^8$ | Physical data |
|---|---|---|---|---|---|
| 2.1 | (isoxazoline) $R^4$ | c-Pr | Me | Me | Resin |
| 2.2 | (isoxazoline) $R^4$ | c-hexyl | Me | Me | Resin |
| 2.3 | (isoxazoline) $R^4$ | (cyclopentenyl) | Me | Me | |
| 2.4 | (isoxazoline) $R^4$ | CH$_2$O-c-Pr | Me | Me | |
| 2.5 | (isoxazoline) $R^4$ | CH$_2$O-c-hexyl | Me | Me | |

TABLE 2-continued
| 2.6 | 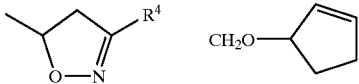 | 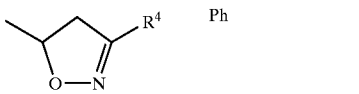 CH₂O— | Me | Me | |
|---|---|---|---|---|---|
| 2.7 | 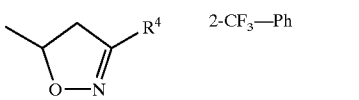 | Ph | Me | Me | m.p. 117–123° C. |
| 2.8 | 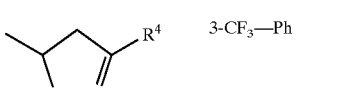 | 2-CF₃—Ph | Me | Me | |
| 2.9 | 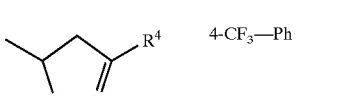 | 3-CF₃—Ph | Me | Me | |
| 2.10 | 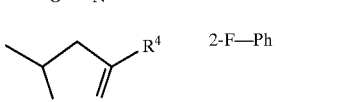 | 4-CF₃—Ph | Me | Me | Resin |
| 2.11 | 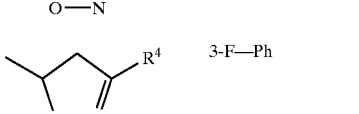 | 2-F—Ph | Me | Me | m.p. 108–112° C. |
| 2.12 | 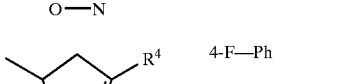 | 3-F—Ph | Me | Me | |
| 2.13 | 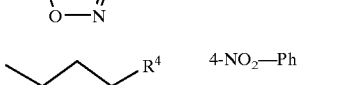 | 4-F—Ph | Me | Me | |
| 2.14 | 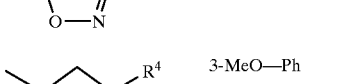 | 4-NO₂—Ph | Me | Me | |
| 2.15 | 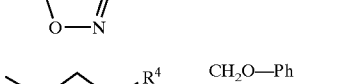 | 3-MeO—Ph | Me | Me | |
| 2.16 | 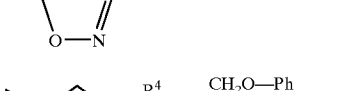 | CH₂O—Ph | Me | Me | |
| 2.17 | 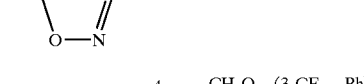 | CH₂O—Ph | H | Et | |
| 2.18 |  | CH₂O—(3-CF₃—Ph) | Me | Me | |
| 2.19 |  | CH₂O—(3-F—Ph) | Me | Me | |
| 2.20 | | CH₂O—(4-NH₂—Ph) | Me | Me | |

TABLE 2-continued
| | | | | |
|---|---|---|---|---|
| 2.21 | 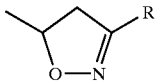 | CH₂O—(3-MeO—Ph) | Me | Me |
| 2.22 | 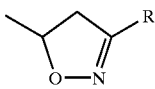 | 2-Py | Me | Me |
| 2.23 | 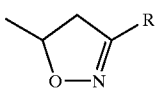 | 2-Py | H | Et |
| 2.24 | 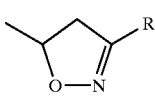 | 3-Py | Me | Me |
| 2.25 | 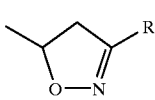 | 4-Py | Me | Me |
| 2.26 | 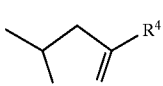 | CH₂O—(2-Py) | Me | Me |
| 2.27 | 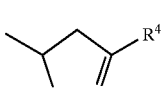 | CH₂O—(3-Py) | Me | Me |
| 2.28 | 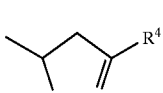 | CH₂O—(4-Py) | Me | Me |
| 2.29 | 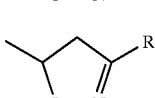 | 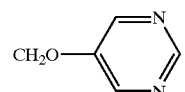 | Me | Me |
| 2.30 | 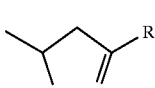 | 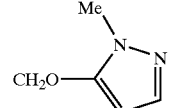 | Me | Me |
| 2.31 | 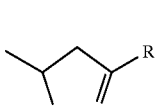 | 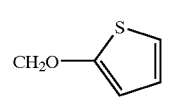 | Me Me Resin | |
| 2.32 | 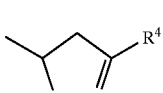 | CH₂NH—CHO | Me | Me |
| 2.33 | 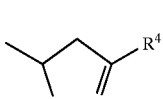 | CH₂NH—C(=O)Me | Me | Me |
| 2.34 | 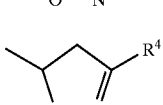 | CH₂NH—C(=O)Me | H | Et |
| 2.35 | 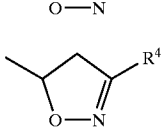 | 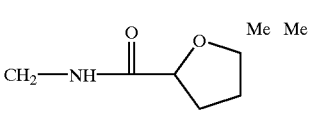 | Me | Me |

TABLE 2-continued

| | Structure | R | R² | R³ |
|---|---|---|---|---|
| 2.36 | isoxazoline-R⁴ | CH₂—NH—C(=O)—(2-Py) | Me | Me |
| 2.37 | isoxazoline-R⁴ | CH₂—NH—C(=O)—CF₃ | Me | Me |
| 2.38 | isoxazoline-R⁴ | CH₂—N(Me)—CHO | Me | Me |
| 2.39 | isoxazoline-R⁴ | CH₂-N(isoxazolidine) | Me | Me |
| 2.40 | isoxazoline-R⁴ | CH₂—NH—SO₂Me | Me | Me |
| 2.41 | isoxazoline-R⁴ | CH₂—NH—SO₂Et | Me | Me |
| 2.42 | isoxazoline-R⁴ | CH₂—NH—C(=O)—Ph | Me | Me |
| 2.43 | isoxazoline-R⁴ | CH₂—C(=O)—NH₂ | Me | Me |
| 2.44 | isoxazoline-R⁴ | CH₂—C(=O)—NHMe | Me | Me |
| 2.45 | isoxazoline-R⁴ | CH₂—C(=O)—NMe₂ | Me | Me |
| 2.46 | isoxazoline-R⁴ | CH₂—C(=O)—NMe₂ | H | Et |
| 2.47 | isoxazoline-R⁴ | CH₂—C(=O)—N(pyrrolidine) | Me | Me |
| 2.48 | isoxazoline-R⁴ | CH₂—C(=O)—NH—OMe | Me | Me |
| 2.49 | isoxazoline-R⁴ | CH₂—(2-Py) | Me | Me |
| 2.50 | isoxazoline-R⁴ | CH₂—(3-Py) | Me | Me |

TABLE 2-continued
| | | | | | |
|---|---|---|---|---|---|
| 2.51 | 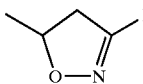 | CH$_2$—(4-Py) | Me | Me | |
| 2.52 | 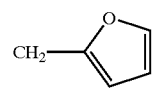 | 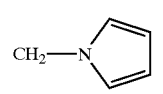 | Me | Me | |
| 2.53 | 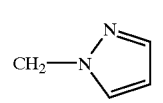 | 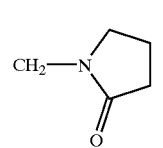 | Me | Me | |
| 2.54 | 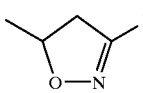 | 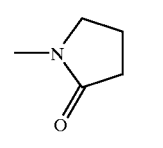 | Me | Me | |
| 2.55 | 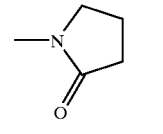 | 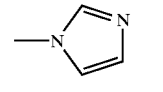 | Me | Me | Resin |
| 2.56 | 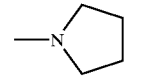 | 2-tetrahydrofuranyl | Me | Me | |
| 2.57 | 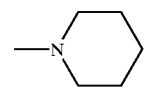 | 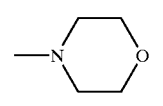 | Me | Me | |
| 2.58 | 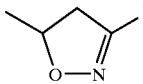 | 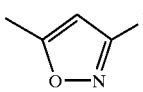 | H | Et | |
| 2.59 |  |  | Me | Me | |
| 2.60 |  |  | Me | Me | |
| 2.61 |  |  | Me | Me | |
| 2.62 |  |  | Me | Me | |
| 2.63 |  | CH$_2$—PO(Me)(Et) | Me | Me | |
| 2.64 |  | c-Pr | Me | Me | Resin |

TABLE 2-continued

| | | | | | |
|---|---|---|---|---|---|
| 2.65 | 5-Me-isoxazol-3-yl (R⁴) | c-hexyl | Me | Me | |
| 2.66 | 5-Me-isoxazol-3-yl (R⁴) | cyclopent-2-enyl-methyl | Me | Me | |
| 2.67 | 5-Me-isoxazol-3-yl (R⁴) | CH₂O-c-Pr | Me | Me | |
| 2.68 | 5-Me-isoxazol-3-yl (R⁴) | CH₂O-c-hexyl | Me | Me | |
| 2.69 | 5-Me-isoxazol-3-yl (R⁴) | CH₂O-cyclopent-2-enyl | Me | Me | |
| 2.70 | 5-Me-isoxazol-3-yl (R⁴) | Ph | Me | Me | Resin |
| 2.71 | 5-Me-isoxazol-3-yl (R⁴) | 2-CF₃—Ph | Me | Me | Resin |
| 2.72 | 5-Me-isoxazol-3-yl (R⁴) | 3-CF₃—Ph | Me | Me | |
| 2.73 | 5-Me-isoxazol-3-yl (R⁴) | 4-CF₃—Ph | Me | Me | Resin |
| 2.74 | 5-Me-isoxazol-3-yl (R⁴) | 2-F—Ph | Me | Me | |
| 2.75 | 5-Me-isoxazol-3-yl (R⁴) | 3-F—Ph | Me | Me | |
| 2.76 | 5-Me-isoxazol-3-yl (R⁴) | 4-F—Ph | Me | Me | |
| 2.77 | 5-Me-isoxazol-3-yl (R⁴) | 4-NO₂—Ph | Me | Me | |
| 2.78 | 5-Me-isoxazol-3-yl (R⁴) | 3-MeO—Ph | Me | Me | |
| 2.79 | 5-Me-isoxazol-3-yl (R⁴) | CH₂O—Ph | Me | Me | |

TABLE 2-continued

| | | | | |
|---|---|---|---|---|
| 2.80 | 5-methyl-isoxazol-3-yl (R⁴) | CH₂O—Ph | H | Et |
| 2.81 | 5-methyl-isoxazol-3-yl (R⁴) | CH₂O—(3-CF₃—Ph) | Me | Me |
| 2.82 | 5-methyl-isoxazol-3-yl (R⁴) | CH₂O—(3-F—Ph) | Me | Me |
| 2.83 | 5-methyl-isoxazol-3-yl (R⁴) | CH₂O—(4-NO₂—Ph) | Me | Me |
| 2.84 | 5-methyl-isoxazol-3-yl (R⁴) | CH₂O—(3-MeO—Ph) | Me | Me |
| 2.85 | 5-methyl-isoxazol-3-yl (R⁴) | 2-Py | Me | Me |
| 2.86 | 5-methyl-isoxazol-3-yl (R⁴) | 2-Py | H | Et |
| 2.87 | 5-methyl-isoxazol-3-yl (R⁴) | 3-Py | Me | Me |
| 2.88 | 5-methyl-isoxazol-3-yl (R⁴) | 4-Py | Me | Me |
| 2.89 | 5-methyl-isoxazol-3-yl (R⁴) | CH₂O—(2-Py) | Me | Me |
| 2.90 | 5-methyl-isoxazol-3-yl (R⁴) | CH₂O—(3-Py) | Me | Me |
| 2.91 | 5-methyl-isoxazol-3-yl (R⁴) | CH₂O—(4-Py) | Me | Me |
| 2.92 | 5-methyl-isoxazol-3-yl (R⁴) | CH₂O-pyrimidin-5-yl | Me | Me |
| 2.93 | 5-methyl-isoxazol-3-yl (R⁴) | CH₂O-(1-Me-pyrazol-5-yl) | Me | Me |
| 2.94 | 5-methyl-isoxazol-3-yl (R⁴) | CH₂O-(2-thienyl) | Me | Me |

TABLE 2-continued
| | | | | |
|---|---|---|---|---|
| 2.95 | 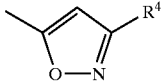 | CH₂NH—CHO | Me | Me |
| 2.96 | 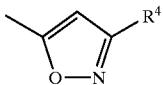 | CH₂NH—C(=O)Me | Me | Me |
| 2.97 | 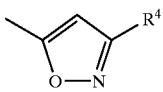 | CH₂NH—C(=O)Me | H | Et |
| 2.98 | 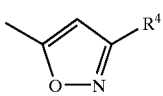 | 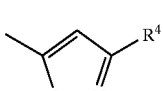 | Me | Me |
| 2.99 | 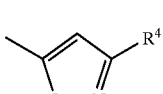 | CH₂—NH—C(=O)—(2-Py) | Me | Me |
| 2.100 | 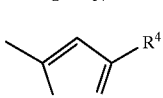 | CH₂—NH—C(=O)—CF₃ | Me | Me |
| 2.101 | 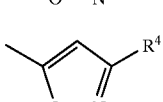 | CH₂—N(Me)—CHO | Me | Me |
| 2.102 | 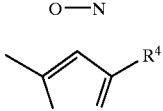 | 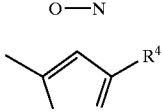 | Me | Me |
| 2.103 | 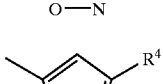 | CH₂—NH—SO₂Me | Me | Me |
| 2.104 | 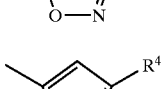 | CH₂—NH—SO₂Et | Me | Me |
| 2.105 | 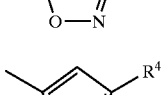 | CH₂—NH—C(=O)—Ph | Me | Me |
| 2.106 | 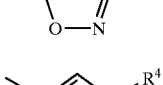 | CH₂—C(=O)—NH₂ | Me | Me |
| 2.107 | 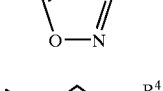 | CH₂—C(=O)—NHMe | Me | Me |
| 2.108 |  | CH₂—C(=O)—NMe₂ | Me | Me |
| 2.109 |  | CH₂—C(=O)—NMe₂ | H | Et |

TABLE 2-continued

| # | Isoxazole | Group | R | R' | Other |
|---|---|---|---|---|---|
| 2.110 | 5-Me-isoxazol-3-yl (R⁴) | CH₂—C(=O)—N(pyrrolidinyl) | Me | Me | Resin |
| 2.111 | 5-Me-isoxazol-3-yl (R⁴) | CH₂—C(=O)—NH—OMe | Me | Me | |
| 2.112 | 5-Me-isoxazol-3-yl (R⁴) | CH₂—(2-Py) | Me | Me | Resin |
| 2.113 | 5-Me-isoxazol-3-yl (R⁴) | CH₂—(3-Py) | Me | Me | |
| 2.114 | 5-Me-isoxazol-3-yl (R⁴) | CH₂—(4-Py) | Me | Me | |
| 2.115 | 5-Me-isoxazol-3-yl (R⁴) | CH₂-(2-furyl) | Me | Me | |
| 2.116 | 5-Me-isoxazol-3-yl (R⁴) | CH₂-(1-pyrrolyl) | Me | Me | |
| 2.117 | 5-Me-isoxazol-3-yl (R⁴) | CH₂-(1-pyrazolyl) | Me | Me | |
| 2.118 | 5-Me-isoxazol-3-yl (R⁴) | CH₂-(2-oxo-pyrrolidin-1-yl) | Me | Me | |
| 2.119 | 5-Me-isoxazol-3-yl (R⁴) | 2-tetrahydrofuranyl | Me | Me | |
| 2.120 | 5-Me-isoxazol-3-yl (R⁴) | (2-oxo-pyrrolidin-1-yl) | Me | Me | |
| 2.121 | 5-Me-isoxazol-3-yl (R⁴) | (2-oxo-pyrrolidin-1-yl) | H | Et | |
| 2.122 | 5-Me-isoxazol-3-yl (R⁴) | (1-imidazolyl) | Me | Me | |
| 2.123 | 5-Me-isoxazol-3-yl (R⁴) | (1-pyrrolidinyl) | Me | Me | |

TABLE 2-continued

| | | | | |
|---|---|---|---|---|
| 2.124 | 5-Me-isoxazol-3-yl (R⁴) | N-piperidinyl | Me | Me |
| 2.125 | 5-Me-isoxazol-3-yl (R⁴) | N-morpholinyl | Me | Me |
| 2.126 | 5-Me-isoxazol-3-yl (R⁴) | CH₂—PO(Me)(Et) | Me | Me |
| 2.127 | 3-Me-4,5-dihydroisoxazol-5-yl (R⁴) | c-Pr | Me | Me |
| 2.128 | 3-Me-4,5-dihydroisoxazol-5-yl (R⁴) | c-hexyl | Me | Me |
| 2.129 | 3-Me-4,5-dihydroisoxazol-5-yl (R⁴) | cyclopent-2-enyl | Me | Me |
| 2.130 | 3-Me-4,5-dihydroisoxazol-5-yl (R⁴) | CH₂O-c-Pr | Me | Me |
| 2.131 | 3-Me-4,5-dihydroisoxazol-5-yl (R⁴) | CH₂O-c-hexyl | Me | Me |
| 2.132 | 3-Me-4,5-dihydroisoxazol-5-yl (R⁴) | CH₂O-cyclopent-2-enyl | Me | Me |
| 2.133 | 3-Me-4,5-dihydroisoxazol-5-yl (R⁴) | Ph | Me | Me |
| 2.134 | 3-Me-4,5-dihydroisoxazol-5-yl (R⁴) | 2-CF₃—Ph | Me | Me |
| 2.135 | 3-Me-4,5-dihydroisoxazol-5-yl (R⁴) | 3-CF₃—Ph | Me | Me |
| 2.136 | 3-Me-4,5-dihydroisoxazol-5-yl (R⁴) | 4-CF₃—Ph | Me | Me |
| 2.137 | 3-Me-4,5-dihydroisoxazol-5-yl (R⁴) | 2-F—Ph | Me | Me |
| 2.138 | 3-Me-4,5-dihydroisoxazol-5-yl (R⁴) | 3-F—Ph | Me | Me |

TABLE 2-continued

| | | | | |
|---|---|---|---|---|
| 2.139 | 3-Me-isoxazoline-R⁴ | 4-F—Ph | Me | Me |
| 2.140 | 3-Me-isoxazoline-R⁴ | 4-NO₂—Ph | Me | Me |
| 2.141 | 3-Me-isoxazoline-R⁴ | 3-MeO—Ph | Me | Me |
| 2.142 | 3-Me-isoxazoline-R⁴ | CH₂O—Ph | Me | Me |
| 2.143 | 3-Me-isoxazoline-R⁴ | CH₂O—Ph | H | Et |
| 2.144 | 3-Me-isoxazoline-R⁴ | CH₂O—(3-CF₃—Ph) | Me | Me |
| 2.145 | 3-Me-isoxazoline-R⁴ | CH₂O—(3-F—Ph) | Me | Me |
| 2.146 | 3-Me-isoxazoline-R⁴ | CH₂O—(4-NO₂—Ph) | Me | Me |
| 2.147 | 3-Me-isoxazoline-R⁴ | CH₂O—(3-MeO—Ph) | Me | Me |
| 2.148 | 3-Me-isoxazoline-R⁴ | 2-Py | Me | Me |
| 2.149 | 3-Me-isoxazoline-R⁴ | 2-Py | H | Et |
| 2.150 | 3-Me-isoxazoline-R⁴ | 3-Py | Me | Me |
| 2.151 | 3-Me-isoxazoline-R⁴ | 4-Py | Me | Me |
| 2.152 | 3-Me-isoxazoline-R⁴ | CH₂O—(2-Py) | Me | Me |
| 2.153 | 3-Me-isoxazoline-R⁴ | CH₂O—(3-Py) | Me | Me |

TABLE 2-continued

| | | | | |
|---|---|---|---|---|
| 2.154 | isoxazoline-R⁴ | CH₂O—(4-Py) | Me | Me |
| 2.155 | isoxazoline-R⁴ | CH₂O-(pyrimidinyl) | Me | Me |
| 2.156 | isoxazoline-R⁴ | CH₂O-(1-Me-pyrazolyl) | Me | Me |
| 2.157 | isoxazoline-R⁴ | CH₂O-(thienyl) | Me | Me |
| 2.158 | isoxazoline-R⁴ | CH₂NH—CHO | Me | Me |
| 2.159 | isoxazoline-R⁴ | CH₂NH—C(=O)Me | Me | Me |
| 2.160 | isoxazoline-R⁴ | CH₂NH—C(=O)Me | H | Et |
| 2.161 | isoxazoline-R⁴ | CH₂—NH—C(=O)-(tetrahydrofuryl) | Me | Me |
| 2.162 | isoxazoline-R⁴ | CH₂—NH—C(=O)—(2-Py) | Me | Me |
| 2.163 | isoxazoline-R⁴ | CH₂—NH—C(=O)—CF₃ | Me | Me |
| 2.164 | isoxazoline-R⁴ | CH₂—N(Me)—CHO | Me | Me |
| 2.165 | isoxazoline-R⁴ | CH₂-(isoxazolidinyl) | Me | Me |
| 2.166 | isoxazoline-R⁴ | CH₂—NH—SO₂Me | Me | Me |
| 2.167 | isoxazoline-R⁴ | CH₂—NH—SO₂Et | Me | Me |
| 2.168 | isoxazoline-R⁴ | CH₂—NH—C(=O)—Ph | Me | Me |

TABLE 2-continued
| | | | | |
|---|---|---|---|---|
| 2.169 | 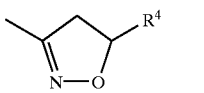 | CH$_2$—C(=O)—NH$_2$ | Me | Me |
| 2.170 | 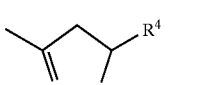 | CH$_2$—C(=O)—NHMe | Me | Me |
| 2.171 | 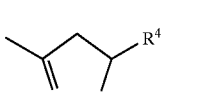 | CH$_2$—C(=O)—NMe$_2$ | Me | Me |
| 2.172 | 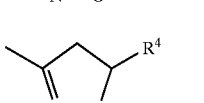 | CH$_2$—C(=O)—NMe$_2$ | H | Et |
| 2.173 | 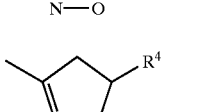 | 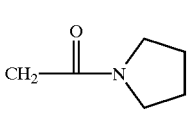 | Me | Me |
| 2.174 | 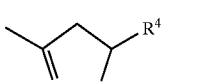 | CH$_2$—C(=O)—NH—OMe | Me | Me |
| 2.175 | 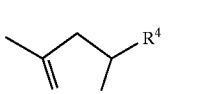 | CH$_2$—(2-Py) | Me | Me |
| 2.176 | 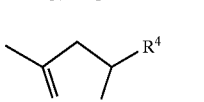 | CH$_2$—(3-Py) | Me | Me |
| 2.177 | 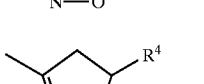 | CH$_2$—(4-Py) | Me | Me |
| 2.178 | 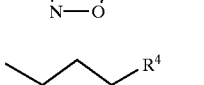 | 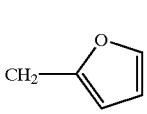 | Me | Me |
| 2.179 | 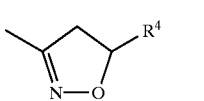 | 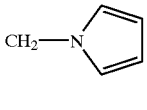 | Me | Me |
| 2.180 | 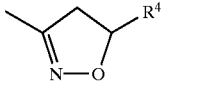 | 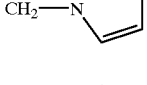 | Me | Me |
| 2.181 | 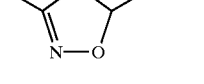 | 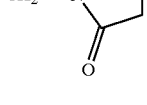 | Me | Me |
| 2.182 | 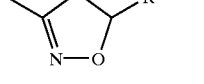 | 2-tetrahydrofuranyl | Me | Me |

TABLE 2-continued
| | | | | |
|---|---|---|---|---|
| 2.183 | 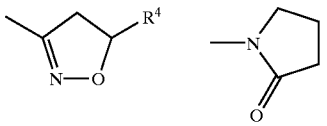 | 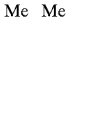 | Me | Me |
| 2.184 | 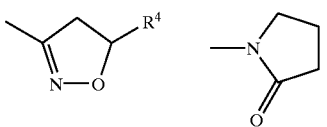 | 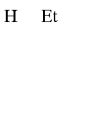 | H | Et |
| 2.185 | 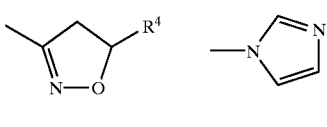 |  | Me | Me |
| 2.186 | 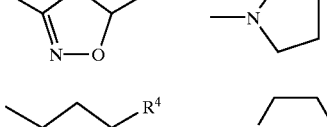 | 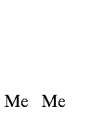 | Me | Me |
| 2.187 | 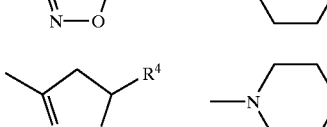 | 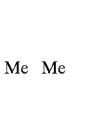 | Me | Me |
| 2.188 | 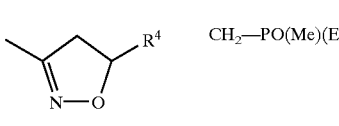 | 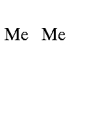 | Me | Me |
| 2.189 | 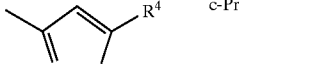 | CH$_2$—PO(Me)(Et) | Me | Me |
| 2.190 | 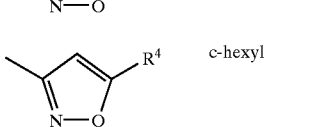 | c-Pr | Me | Me |
| 2.191 |  | c-hexyl | Me | Me |
| 2.192 | 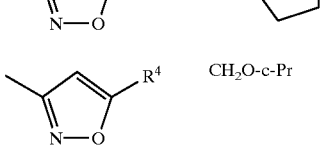 | 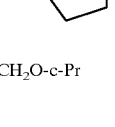 | Me | Me |
| 2.193 |  | CH$_2$O-c-Pr | Me | Me |
| 2.194 | 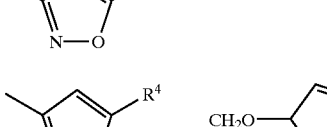 | CH$_2$O-c-hexyl | Me | Me |
| 2.195 |  |  | Me | Me |
| 2.196 | 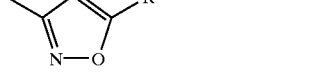 | Ph | Me | Me |

TABLE 2-continued
| | | | | |
|---|---|---|---|---|
| 2.197 | 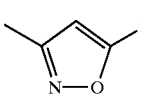 | 2-CF$_3$—Ph | Me | Me |
| 2.198 | 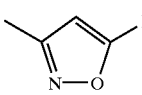 | 3-CF$_3$—Ph | Me | Me |
| 2.199 | 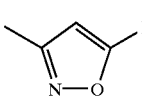 | 4-CF$_3$—Ph | Me | Me |
| 2.200 | 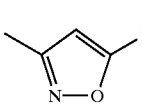 | 2-F—Ph | Me | Me |
| 2.201 | 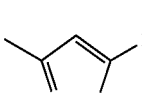 | 3-F—Ph | Me | Me |
| 2.202 | 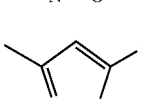 | 4-F—Ph | Me | Me |
| 2.203 | 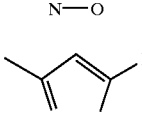 | 4-NO$_2$—Ph | Me | Me |
| 2.204 | 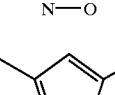 | 3-MeO—Ph | Me | Me |
| 2.205 | 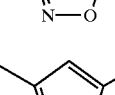 | CH$_2$O—Ph | Me | Me |
| 2.206 | 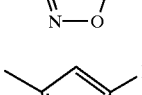 | CH$_2$O—Ph | H | Et |
| 2.207 | 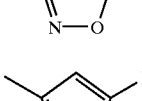 | CH$_2$O—(3-CF$_3$—Ph) | Me | Me |
| 2.208 | 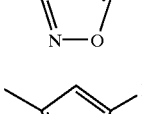 | CH$_2$O—(3-F—Ph) | Me | Me |
| 2.209 | 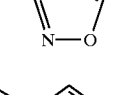 | CH$_2$O—(4-NO$_2$—Ph) | Me | Me |
| 2.210 | 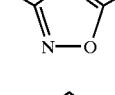 | CH$_2$O—(3-MeO—Ph) | Me | Me |
| 2.211 | 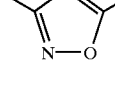 | 2-Py | Me | Me |

TABLE 2-continued
| | | | | |
|---|---|---|---|---|
| 2.212 | 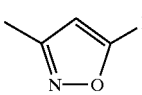 | 2-Py | H | Et |
| 2.213 | 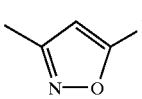 | 3-Py | Me | Me |
| 2.214 | 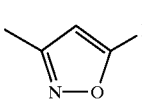 | 4-Py | Me | Me |
| 2.215 | 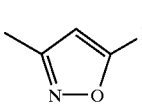 | CH$_2$O—(2-Py) | Me | Me |
| 2.216 | 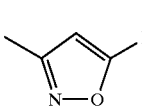 | CH$_2$O—(3-Py) | Me | Me |
| 2.217 | 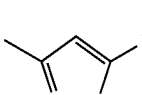 | CH$_2$O—(4-Py) | Me | Me |
| 2.218 | 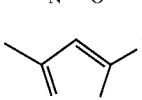 | 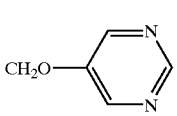 | Me | Me |
| 2.219 | 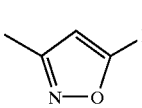 | 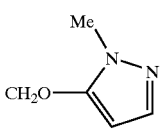 | Me | Me |
| 2.220 | 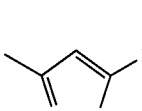 | 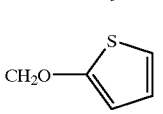 | Me | Me |
| 2.221 | 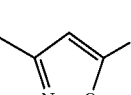 | CH$_2$NH—CHO | Me | Me |
| 2.222 | 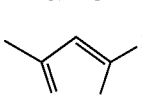 | CH$_2$NH—C(=O)Me | Me | Me |
| 2.223 | 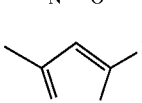 | CH$_2$NH—C(=O)Me | H | Et |
| 2.224 | 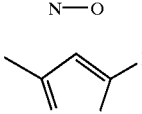 | 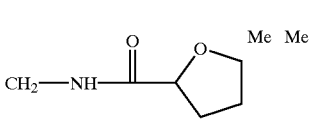 | Me | Me |
| 2.225 | 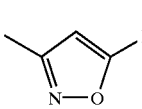 | CH$_2$—NH—C(=O)—(2-Py) | Me | Me |
| 2.226 | 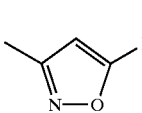 | CH$_2$—NH—C(=O)—CF$_3$ | Me | Me |

TABLE 2-continued

| | | | | |
|---|---|---|---|---|
| 2.227 | 3-Me-isoxazol-5-yl, R⁴ | CH₂—N(Me)—CHO | Me | Me |
| 2.228 | 3-Me-isoxazol-5-yl, R⁴ | CH₂—(isoxazolidin-2-yl) | Me | Me |
| 2.229 | 3-Me-isoxazol-5-yl, R⁴ | CH₂—NH—SO₂Me | Me | Me |
| 2.230 | 3-Me-isoxazol-5-yl, R⁴ | CH₂—NH—SO₂Et | Me | Me |
| 2.231 | 3-Me-isoxazol-5-yl, R⁴ | CH₂—NH—C(=O)—Ph | Me | Me |
| 2.232 | 3-Me-isoxazol-5-yl, R⁴ | CH₂—C(=O)—NH₂ | Me | Me |
| 2.233 | 3-Me-isoxazol-5-yl, R⁴ | CH₂—C(=O)—NHMe | Me | Me |
| 2.234 | 3-Me-isoxazol-5-yl, R⁴ | CH₂—C(=O)—NMe₂ | Me | Me |
| 2.235 | 3-Me-isoxazol-5-yl, R⁴ | CH₂—C(=O)—NMe₂ | H | Et |
| 2.236 | 3-Me-isoxazol-5-yl, R⁴ | CH₂—C(=O)—(pyrrolidin-1-yl) | Me | Me |
| 2.237 | 3-Me-isoxazol-5-yl, R⁴ | CH₂—C(=O)—NH—OMe | Me | Me |
| 2.238 | 3-Me-isoxazol-5-yl, R⁴ | CH₂—(2-Py) | Me | Me |
| 2.239 | 3-Me-isoxazol-5-yl, R⁴ | CH₂—(3-Py) | Me | Me |
| 2.240 | 3-Me-isoxazol-5-yl, R⁴ | CH₂—(4-Py) | Me | Me |
| 2.241 | 3-Me-isoxazol-5-yl, R⁴ | CH₂—(furan-2-yl) | Me | Me |

TABLE 2-continued

| # | Structure | Substituent | R | R' |
|---|---|---|---|---|
| 2.242 | 3-methylisoxazol-5-yl (R⁴) | CH₂-N-pyrrolyl | Me | Me |
| 2.243 | 3-methylisoxazol-5-yl (R⁴) | CH₂-N-pyrazolyl | Me | Me |
| 2.244 | 3-methylisoxazol-5-yl (R⁴) | CH₂-N-(2-oxopyrrolidinyl) | Me | Me |
| 2.245 | 3-methylisoxazol-5-yl (R⁴) | 2-tetrahydrofuranyl | Me | Me |
| 2.246 | 3-methylisoxazol-5-yl (R⁴) | N-(2-oxopyrrolidinyl) | Me | Me |
| 2.247 | 3-methylisoxazol-5-yl (R⁴) | N-(2-oxopyrrolidinyl) | H | Et |
| 2.248 | 3-methylisoxazol-5-yl (R⁴) | N-imidazolyl | Me | Me |
| 2.249 | 3-methylisoxazol-5-yl (R⁴) | N-pyrrolidinyl | Me | Me |
| 2.250 | 3-methylisoxazol-5-yl (R⁴) | N-piperidinyl | Me | Me |
| 2.251 | 3-methylisoxazol-5-yl (R⁴) | N-morpholinyl | Me | Me |
| 2.252 | 3-methylisoxazol-5-yl (R⁴) | CH₂—PO(Me)(Et) | Me | Me |
| 2.253 | 3-methylisoxazol-5-yl (R⁴) | Ph | Me | Me |
| 2.254 | 3-methyl-1,3,4-oxadiazol-5-yl (R⁴) | Ph | H | Et |
| 2.255 | 3-methyl-1,3,4-oxadiazol-5-yl (R⁴) | 3-F—Ph | Me | Me |

TABLE 2-continued

| | | | | |
|---|---|---|---|---|
| 2.256 | 1,2,4-oxadiazole (3-Me, 5-R⁴) | CH₂—Ph | Me | Me |
| 2.257 | 1,2,4-oxadiazole (3-Me, 5-R⁴) | CH₂—(3-Me—Ph) | Me | Me |
| 2.258 | 1,2,4-oxadiazole (5-Me, 3-R⁴) | Ph | Me | Me |
| 2.259 | 1,2,4-oxadiazole (5-Me, 3-R⁴) | Ph | H | Et |
| 2.260 | 1,2,4-oxadiazole (5-Me, 3-R⁴) | 3-F—Ph | Me | Me |
| 2.261 | 1,2,4-oxadiazole (5-Me, 3-R⁴) | CH₂—Ph | Me | Me |
| 2.262 | 1,2,4-oxadiazole (5-Me, 3-R⁴) | CH₂—(3-Me—Ph) | Me | Me |
| 2.263 | 1,3,4-oxadiazole (2-Me, 5-R⁴) | Ph | Me | Me |
| 2.264 | 1,3,4-oxadiazole (2-Me, 5-R⁴) | Ph | H | Et |
| 2.265 | 1,3,4-oxadiazole (2-Me, 5-R⁴) | 3-F—Ph | Me | Me |
| 2.266 | 1,3,4-oxadiazole (2-Me, 5-R⁴) | CH₂—Ph | Me | Me |
| 2.267 | 1,3,4-oxadiazole (2-Me, 5-R⁴) | CH₂—(3-Me—Ph) | Me | Me |
| 2.268 | oxazole (2-Me, 5-R⁴) | Ph | Me | Me |
| 2.269 | oxazole (2-Me, 5-R⁴) | Ph | H | Et |
| 2.270 | oxazole (2-Me, 5-R⁴) | 3-F—Ph | Me | Me |

TABLE 2-continued
| 2.271 | 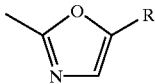 | CH₂—Ph | Me | Me |
| 2.272 | 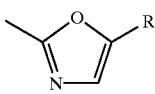 | CH₂—(3-Me—Ph) | Me | Me |
| 2.273 | 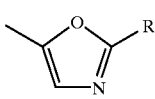 | Ph | Me | Me |
| 2.274 | 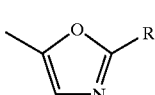 | Ph | H | Et |
| 2.275 | 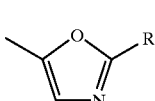 | 3-F—Ph | Me | Me |
| 2.276 | 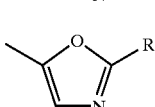 | CH₂—Ph | Me | Me |
| 2.277 | 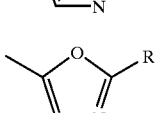 | CH₂—(3-Me—Ph) | Me | Me |
| 2.278 | 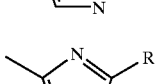 | Ph | Me | Me |
| 2.279 | 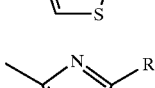 | Ph | H | Et |
| 2.280 | 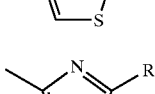 | 3-F—Ph | Me | Me |
| 2.281 | 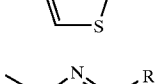 | CH₂—Ph | Me | Me |
| 2.282 | 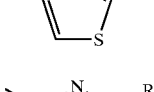 | CH₂—(3-Me—Ph) | Me | Me |
| 2.283 | 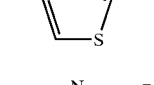 | Ph | Me | Me |
| 2.284 | 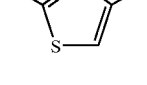 | Ph | H | Et |
| 2.285 | 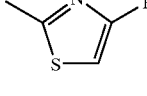 | 3-F—Ph | Me | Me |

TABLE 2-continued
| No. | Structure | | R⁴ | | |
|---|---|---|---|---|---|
| 2.286 | 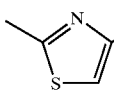 | CH₂—Ph | | Me | Me |
| 2.287 | 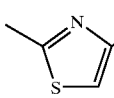 | CH₂—(3-Me—Ph) | | Me | Me |
| 2.288 | 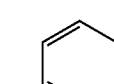 | — | | Me | Me |
| 2.289 | 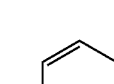 | — | | H | Et |
| 2.290 | 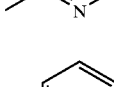 | — | | Me | Me |
| 2.291 | 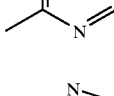 | — | | Me | Me |
| 2.292 | 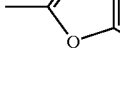 | — | | Me | Me |
TABLE 3
Compounds of the formula (I) according to the invention in which the substituents and symbols have the following meanings:
Q = Q1    R³, R⁶ = H    X = OCH₂    Y, Z = CH₂
v = 1     w = 2         k = 1
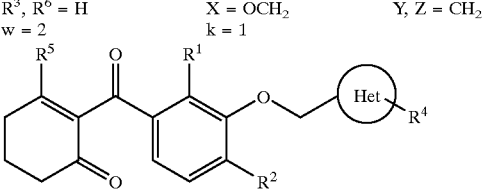
| No. | R¹ | R² | R⁵ | Het | R⁴ | Physical data |
|---|---|---|---|---|---|---|
| 3.1 | Cl | SO₂Me | OC(O)—Ph | 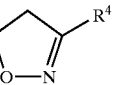 | c-hexyl | m.p. 65–72° C. |
| 3.2 | Cl | SO₂Me | OC(O)—Ph | 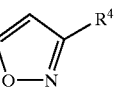 | c-hexyl | Resin |
| 3.3 | Cl | SO₂Me | OC(O)—Ph | 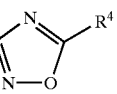 | Ph | |

TABLE 3-continued

Compounds of the formula (I) according to the invention in which the substituents and symbols have the following meanings:

Q = Q1   $R^3, R^6$ = H   X = $OCH_2$   Y, Z = $CH_2$
v = 1    w = 2            k = 1

| No. | $R^1$ | $R^2$ | $R^5$ | Het | $R^4$ | Physical data |
|---|---|---|---|---|---|---|
| 3.4 | Cl | $CF_3$ | OC(O)—Ph | isoxazoline | c-hexyl | |
| 3.5 | Cl | $SO_2Me$ | $OSO_2Me$ | isoxazoline | c-hexyl | |
| 3.6 | Cl | $SO_2Me$ | $OSO_2Et$ | isoxazoline | $CH_2O$—c-hexenyl | |
| 3.7 | Cl | $SO_2Me$ | $OSO_2Ph$ | isoxazoline | c-Pr | |
| 3.8 | Cl | $SO_2Me$ | $OSO_2Ph$ | isoxazoline | $CH_2$—NH—CHO | Resin |
| 3.9 | Cl | $SO_2Me$ | $OSO_2Ph$ | isoxazoline | $CH_2$—N-pyrrolidinone | |
| 3.10 | Cl | $SO_2Me$ | $OSO_2Ph$ | oxadiazole | Ph | |
| 3.11 | Cl | $SO_2Me$ | $OSO_2$-(4-Me-Ph) | isoxazoline | c-hexyl | |
| 3.12 | Cl | $SO_2Me$ | $OSO_2$-(4-Me-Ph) | isoxazoline | $CH_2$—NH—CHO | |
| 3.13 | Cl | $SO_2Me$ | $OSO_2$-(4-Me-Ph) | oxadiazole | Ph | |
| 3.14 | Cl | $SO_2Me$ | $OSO_2$—Pr | isoxazoline | $CH_2$—NH—CHO | |
| 3.15 | Cl | $SO_2Me$ | $OSO_2Bu$ | isoxazoline | $CH_2$—NH—CHO | |

TABLE 3-continued

Compounds of the formula (I) according to the invention in which the substituents and symbols have the following meanings:

| Q = Q1 | $R^3, R^6$ = H | X = $OCH_2$ | Y, Z = $CH_2$ |
|---|---|---|---|
| v = 1 | w = 2 | k = 1 | |

| No. | $R^1$ | $R^2$ | $R^5$ | Het | $R^4$ | Physical data |
|---|---|---|---|---|---|---|
| 3.16 | Cl | $SO_2Me$ | $OSO_2Ph$ | isoxazole | c-Pr | Resin |
| 3.17 | Cl | $SO_2Me$ | $OSO_2Ph$ | isoxazole | 2-Py | |
| 3.18 | Cl | $SO_2Me$ | $OSO_2Ph$ | isoxazole | $CH_2$—N(Me)—CHO | |
| 3.19 | Cl | $SO_2Me$ | $OSO_2Ph$ | 1,2,4-oxadiazole | $CH_2$—N-pyrrolidin-2-one | |
| 3.20 | Cl | $CF_3$ | $OSO_2Ph$ | 1,2,4-oxadiazole | Ph | |

TABLE 4

Compounds of the formula (I) according to the invention in which the substituents and symbols have the following meanings:

| Q = Q1a | $R^5$ = OH | X = $OCH_2$ | Y, Z = $CH_2$ |
|---|---|---|---|
| v = 1 | k = 0 or 1 | $R^3, R^{17}$ to $R^{22}$ = H | |

| No. | $R^1$ | $R^2$ | Het | $R^4$ | Physical data |
|---|---|---|---|---|---|
| 4.1 | Cl | Cl | isoxazoline | c-Pr | Resin |
| 4.2 | Cl | Cl | isoxazoline | Ph | m.p. 63–69° C. |
| 4.3 | Cl | Cl | isoxazoline | 2-Py | m.p. 110–118° C. |
| 4.4 | Br | Br | isoxazoline | c-Pr | Resin |

TABLE 4-continued

Compounds of the formula (I) according to the invention in which the substituents and symbols have the following meanings:

Q = Q1a, v = 1, R⁵ = OH, k = 0 or 1, X = OCH₂, Y, Z = CH₂, R³, R¹⁷ to R²² = H

| No. | R¹ | R² | Het | R⁴ | Physical data |
|---|---|---|---|---|---|
| 4.5 | Br | Br | 5-methyl-4,5-dihydroisoxazol-3-yl | Ph | m.p. 59–65° C. |
| 4.6 | Br | Br | 5-methyl-4,5-dihydroisoxazol-3-yl | 2-Py | Resin |
| 4.7 | Br | Br | 5-methyl-4,5-dihydroisoxazol-3-yl | 3-Py | Resin |
| 4.8 | Cl | SO₂Et | 5-methyl-4,5-dihydroisoxazol-3-yl | c-Pr | Resin |
| 4.9 | Cl | SO₂Et | 5-methyl-4,5-dihydroisoxazol-3-yl | Ph | Resin |
| 4.10 | Cl | SO₂Et | 5-methyl-4,5-dihydroisoxazol-3-yl | 2-Py | Resin |
| 4.11 | Cl | SO₂Et | 5-methyl-4,5-dihydroisoxazol-3-yl | 3-Py | |
| 4.12 | Cl | SO₂Pr | 5-methyl-4,5-dihydroisoxazol-3-yl | 2-Py | |
| 4.13 | NO₂ | SO₂Me | 5-methyl-4,5-dihydroisoxazol-3-yl | Ph | |
| 4.14 | NO₂ | SO₂Me | 5-methyl-4,5-dihydroisoxazol-3-yl | c-Pr | m.p. 121–124° C. |
| 4.15 | NO₂ | SO₂Et | 5-methyl-4,5-dihydroisoxazol-3-yl | c-Pr | |
| 4.16 | NO₂ | SO₂Pr | 5-methyl-4,5-dihydroisoxazol-3-yl | c-Pr | |
| 4.17 | NO₂ | SO₂Bu | 5-methyl-4,5-dihydroisoxazol-3-yl | c-Pr | |
| 4.18 | NO₂ | SO₂Me | 5-methyl-4,5-dihydroisoxazol-3-yl | 2-Py | Resin |
| 4.19 | NO₂ | SO₂Me | 5-methyl-4,5-dihydroisoxazol-3-yl | 3-Py | |
| 4.20 | Me | SO₂Me | 5-methyl-4,5-dihydroisoxazol-3-yl | Ph | |
| 4.21 | Me | SO₂Me | 5-methyl-4,5-dihydroisoxazol-3-yl | 2-Py | |
| 4.22 | Cl | Cl | 5-methyl-4,5-dihydroisoxazol-3-yl | c-Pr | Resin |
| 4.23 | Cl | Cl | 5-methyl-4,5-dihydroisoxazol-3-yl | Ph | Resin |
| 4.24 | Cl | Cl | 5-methyl-4,5-dihydroisoxazol-3-yl | 2-Py | Resin |
| 4.25 | Br | Br | 5-methyl-4,5-dihydroisoxazol-3-yl | c-Pr | Resin |
| 4.26 | Br | Br | 5-methyl-4,5-dihydroisoxazol-3-yl | Ph | Resin |
| 4.27 | Br | Br | 5-methyl-4,5-dihydroisoxazol-3-yl | 2-Py | Resin |

TABLE 4-continued

Compounds of the formula (I) according to the invention in which the substituents and symbols have the following meanings:

Q = Q1a  R$^5$ = OH  X = OCH$_2$  Y, Z = CH$_2$
v = 1  k = 0 or 1  R$^3$, R$^{17}$ to R$^{22}$ = H

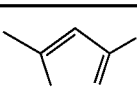

| No. | R$^1$ | R$^2$ | Het | R$^4$ | Physical data |
|---|---|---|---|---|---|
| 4.28 | Br | Br | 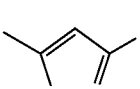 | 3-Py | |
| 4.29 | Cl | SO$_2$Et | 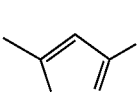 | c-Pr | |
| 4.30 | Cl | SO$_2$Et | 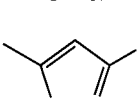 | Ph | |
| 4.31 | Cl | SO$_2$Et | 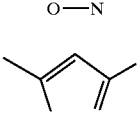 | 2-Py | |
| 4.32 | Cl | SO$_2$Et | 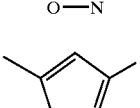 | 3-Py | |
| 4.33 | Cl | SO$_2$Pr | 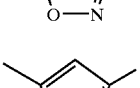 | 2-Py | |
| 4.34 | NO$_2$ | SO$_2$Me | 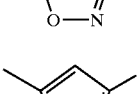 | Ph | |
| 4.35 | NO$_2$ | SO$_2$Me | 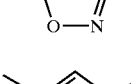 | c-Pr | |
| 4.36 | NO$_2$ | SO$_2$Et | 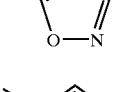 | c-Pr | |
| 4.37 | NO$_2$ | SO$_2$Pr | 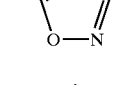 | c-Pr | |
| 4.38 | NO$_2$ | SO$_2$Bu | 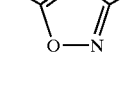 | c-Pr | |
| 4.39 | NO$_2$ | SO$_2$Me | 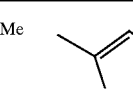 | 2-Py | Resin |

TABLE 4-continued

Compounds of the formula (I) according to the invention in which the substituents and symbols have the following meanings:

Q = Q1a  R$^5$ = OH  X = OCH$_2$  Y, Z = CH$_2$
v = 1  k = 0 or 1  R$^3$, R$^{17}$ to R$^{22}$ = H

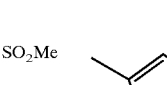

| No. | R$^1$ | R$^2$ | Het | R$^4$ | Physical data |
|---|---|---|---|---|---|
| 4.40 | NO$_2$ | SO$_2$Me | 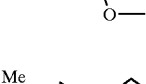 | 3-Py | |
| 4.41 | Me | SO$_2$Me | 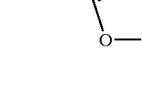 | Ph | |
| 4.42 | Me | SO$_2$Me | 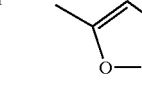 | 2-Py | |
| 4.43 | Cl | Cl | 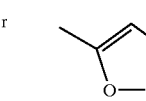 | Ph | |
| 4.44 | Br | Br | 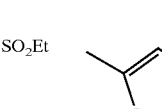 | Ph | Resin |
| 4.45 | Cl | SO$_2$Et | 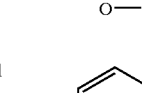 | Ph | |
| 4.46 | Cl | Cl | 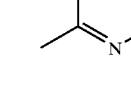 | — | |
| 4.47 | Br | Br | 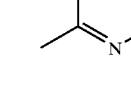 | — | m.p. 74–82° C. |
| 4.48 | Cl | SO$_2$Et | 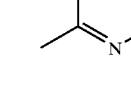 | — | |

TABLE 5

Compounds of the formula (I) according to the invention in which the substituents and symbols have the following meanings:

R¹ = 2-Cl  R² = 4-SO₂Me  X = OCH₂  $R^3, R^9$ = H
Q = Q2  k = 0 or 1  $R^7, R^8$ = Me

| No. | R¹ | R² | Het | R⁴ | Physical data |
|---|---|---|---|---|---|
| 5.1 | Cl | Cl | isoxazoline | c-Pr | |
| 5.2 | Cl | Cl | isoxazoline | Ph | Resin |
| 5.3 | Cl | Cl | isoxazoline | 2-Py | Resin |
| 5.4 | Br | Br | isoxazoline | c-Pr | |
| 5.5 | Br | Br | isoxazoline | Ph | m.p. 67–71° C. |
| 5.6 | Br | Br | isoxazoline | 2-Py | |
| 5.7 | Br | Br | isoxazoline | 3-Py | |
| 5.8 | Cl | SO₂Et | isoxazoline | c-Pr | Resin |
| 5.9 | Cl | SO₂Et | isoxazoline | Ph | |
| 5.10 | Cl | SO₂Et | isoxazoline | 2-Py | Resin |
| 5.11 | Cl | SO₂Et | isoxazoline | 3-Py | |
| 5.12 | Cl | SO₂Pr | isoxazoline | 2-Py | |
| 5.13 | NO₂ | SO₂Me | isoxazoline | Ph | |
| 5.14 | NO₂ | SO₂Me | isoxazoline | c-Pr | |
| 5.15 | NO₂ | SO₂Et | isoxazoline | c-Pr | |
| 5.16 | NO₂ | SO₂Pr | isoxazoline | c-Pr | |
| 5.17 | NO₂ | SO₂Bu | isoxazoline | c-Pr | |
| 5.18 | NO₂ | SO₂Me | isoxazoline | 2-Py | Resin |
| 5.19 | NO₂ | SO₂Me | isoxazoline | 3-Py | |
| 5.20 | Me | SO₂Me | isoxazoline | Ph | |
| 5.21 | Me | SO₂Me | isoxazoline | 2-Py | |
| 5.22 | Cl | Cl | isoxazole | c-Pr | |
| 5.23 | Cl | Cl | isoxazole | Ph | |

TABLE 5-continued

Compounds of the formula (I) according to the invention in which the substituents and symbols have the following meanings:

R¹ = 2-Cl, Q = Q2, R² = 4-SO$_2$Me, k = 0 or 1, X = OCH$_2$, R³, R⁹ = H, R⁷, R⁸ = Me

| No. | R¹ | R² | Het | R⁴ | Physical data |
|---|---|---|---|---|---|
| 5.24 | Cl | Cl | 5-Me-isoxazol-3-yl | 2-Py | Resin |
| 5.25 | Br | Br | 5-Me-isoxazol-3-yl | c-Pr | |
| 5.26 | Br | Br | 5-Me-isoxazol-3-yl | Ph | Resin |
| 5.27 | Br | Br | 5-Me-isoxazol-3-yl | 2-Py | |
| 5.28 | Br | Br | 5-Me-isoxazol-3-yl | 3-Py | |
| 5.29 | Cl | SO$_2$Et | 5-Me-isoxazol-3-yl | c-Pr | |
| 5.30 | Cl | SO$_2$Et | 5-Me-isoxazol-3-yl | Ph | |
| 5.31 | Cl | SO$_2$Et | 5-Me-isoxazol-3-yl | 2-Py | |
| 5.32 | Cl | SO$_2$Et | 5-Me-isoxazol-3-yl | 3-Py | |
| 5.33 | Cl | SO$_2$Pr | 5-Me-isoxazol-3-yl | 2-Py | |
| 5.34 | NO$_2$ | SO$_2$Me | 5-Me-isoxazol-3-yl | Ph | |
| 5.35 | NO$_2$ | SO$_2$Me | 5-Me-isoxazol-3-yl | c-Pr | |
| 5.36 | NO$_2$ | SO$_2$Et | 5-Me-isoxazol-3-yl | c-Pr | |
| 5.37 | NO$_2$ | SO$_2$Pr | 5-Me-isoxazol-3-yl | c-Pr | |
| 5.38 | NO$_2$ | SO$_2$Bu | 5-Me-isoxazol-3-yl | c-Pr | |
| 5.39 | NO$_2$ | SO$_2$Me | 5-Me-isoxazol-3-yl | 2-Py | Resin |
| 5.40 | NO$_2$ | SO$_2$Me | 5-Me-isoxazol-3-yl | 3-Py | |
| 5.41 | Me | SO$_2$Me | 5-Me-isoxazol-3-yl | Ph | |
| 5.42 | Me | SO$_2$Me | 5-Me-isoxazol-3-yl | 2-Py | |
| 5.43 | Cl | Cl | 5-Me-isoxazol-3-yl | Ph | |
| 5.44 | Br | Br | 5-Me-isoxazol-3-yl | Ph | Resin |
| 5.45 | Cl | SO$_2$Et | 5-Me-isoxazol-3-yl | Ph | |
| 5.46 | Cl | Cl | 2-methylquinolin-yl | — | |

TABLE 5-continued

Compounds of the formula (I) according to the invention in which the substituents and symbols have the following meanings:

$R^1$ = 2-Cl, $R^2$ = 4-SO$_2$Me, X = OCH$_2$, $R^3$, $R^9$ = H
Q = Q2, k = 0 or 1, $R^7$, $R^8$ = Me

| No. | $R^1$ | $R^2$ | Het | $R^4$ | Physical data |
|-----|-------|-------|-----|-------|---------------|
| 5.47 | Br | Br | quinoline | — | |
| 5.48 | Cl | SO$_2$Et | quinoline | — | |

B. FORMULATION EXAMPLES

1. Dust

A dust is obtained by mixing 10 parts by weight of a compound of the formula (I) and 90 parts by weight of talc as inert substance and comminuting the mixture in a hammer mill.

2. Dispersible Powder

A wettable powder which is readily dispersible in water is obtained by mixing 25 parts by weight of a compound of the formula (I), 64 parts by weight of kaolin-containing quarz as inert substance, 10 parts by weight of potassium liginosulfonate and 1 part by weight of sodium oleoylmethyltaurinate as wetter and dispersant and grinding the mixture in a pinned-disk mill.

3. Dispersion Concentrate

A dispersion concentrate which is readily dispersible in water is obtained by mixing 20 parts by weight of a compound of the formula (I), 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to above 277° C.) and grinding the mixture in a bowl mill to a fineness of below 5 microns.

4. Emulsifiable Concentrate

An emulsifiable concentrate is obtained from 15 parts by weight of a compound of the formula (I), 75 parts by weight of cyclohexanone as solvent and 10 parts by weight of oxethylated nonylphenol as emulsifier.

5. Water-dispersible Granules

Water-dispersible granules are obtained by mixing 75 parts by weight of a compound of the formula (I)

10" of calcium lignosulfonate,

5" of sodium lauryl sulfate,

3" of polyvinyl alcohol and

7" of kaolin, grinding the mixture on a pinned-disk mill and granulating the powder in a fluidized bed by spraying on water as granulation liquid.

Water-dispersible granules are also obtained by homogenizing and precomminuting, on a colloid mill, 25 parts by weight of a compound of the formula (I), 5" of sodium 2,2'-dinaphthylmethane-6,6'-disulfonate, 2" of sodium oleoylmethyltaurinate, 1" of polyvinyl alcohol, 17" of calcium carbonate and 50" of water, subsequently grinding the mixture in a bead mill, and atomizing and drying the resulting suspension in a spray tower by means of a single-substance nozzle.

C. BIOLOGICAL EXAMPLES

1. Pre-emergence Effect on Weeds

Seeds of monocotyledonous and dicotyledonous weed plants are placed in sandy loam soil in cardboard pots and covered with soil. The compounds according to the invention which were formulated in the form of wettable powders or emulsion concentrates are then applied to the surface of the soil cover in the form of aqueous suspensions or emulsions at an application rate of 600 to 800 l of water/ha (converted) at a dosage of 1 kg of active substance or less per hectare (converted). After the treatment, the az pots are placed in the greenhouse and kept under good growth conditions for the weeds. Visual scoring of the damage to the plants or the emergence is carried out after the test plants have emerged after a test period of 3 to 4 weeks in comparison with untreated controls. For example the compounds of Example Nos. 4.5 and 4.44 exhibit at least 70% action against *Amaranthus retroflexus* and at least 60% action against *Stellaria media*.

2. Post-emergence Effect on Weeds

Seeds of monocotyledonous and dicotyledonous weed plants are placed in sandy loam soil in cardboard pots, covered with soil and grown in the greenhouse under good growth conditions. Two to three weeks after sowing, the test plants are treated in the three-leaf stage. The compounds according to the invention which are formulated as wettable powders or emulsion concentrates are sprayed onto the green parts of the plants at a dosage of 1 kg of active substance or less per hectare (converted) at an application rate of 600 to 800 l of water/ha (converted). After the test plants have remained in the greenhouse for approximately 3 to 4 weeks under optimal growth conditions, the effect of the preparations is scored in comparison with untreated controls. The compositions according to the invention also have a good herbicidal activity against a broad spectrum of economically important grass weeds and broad-leaved weeds when used post-emergence. For example, the compounds of Example Nos. 4.2 and 4.26 have at least 70% action against *Amaranthus retroflexus*. The compounds of Example Nos. 4.5, 4.26 and 4.44 have at least 80% action against *Sinapis alba* and *Stellaria media*.

3. Effect on Harmful Plants in Rice

Typical harmful plants in rice crops are grown in a greenhouse under paddy rice conditions (flooding level of the water: 2–3 cm). After the treatment with the formulated compounds according to the invention at a dosage of 1 kg of active substance or less per hectar (converted), the test plants are placed in the greenhouse under optimal growth conditions, and kept over the entire test period like this. Approximately three weeks after application, they are evaluated by means of visual scoring of the plant damage in comparison with untreated controls. The compounds according to the invention have a very good herbicidal action against harmful plants. For example, the compounds of Example Nos. 4.5, 4.26 and 4.44 have at least 70% action against *Echinocloa crus-galli*.

4. Crop Plant Tolerance

In further greenhouse experiments, seeds of a substantial number of crop plants and weeds are placed in sandy loam soil and covered with soil. Some of the pots are treated immediately as described in Section 1, while the remaining ones are placed in the greenhouse until the plants have developed two to three true leaves and are then sprayed with various dosages of the substances of the formula (I) according to the invention as described in Section 2. Visual scoring four to five weeks after the application and after the plants have remained in the greenhouse reveals that the compounds according to the invention generally do not inflict substantial damage, if any, to dicotyledonous crops such as soya beans and sugar beet when applied pre- and post-emergence, even when high doages of active substance are used. Moreover, some substances also leave Gramineae crops such as, for example, barley, wheat and rice unharmed. Some of the compounds of the formula (I) are highly selective and are therefore suitable for controlling undesired plant growth in agricultural crops.

We claim:

1. A benzoyl compound of the formula (I)

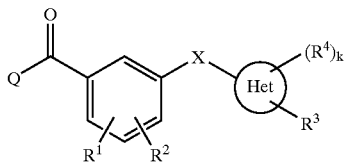

(I)

in which

Q is a radical of the formula (Q1) which is linked in the 2-position

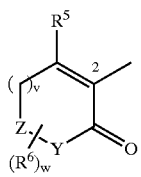

(Q1)

X is a straight-chain or branched $(C_1-C_6)$-alkylene, $(C_2-C_6)$-alkenylene or $(C_2-C_6)$-alkynylene chain, which is substituted by w radicals selected from the group consisting of $OR^{3a}$, $OCOR^{3a}$, $(C_1-C_6)$alkyl, $(C_2-C_6)$alkenyl $(C_2-C_6)$alkynyl, phenyl and phenyl-$(C_1-C_6)$-alkyl, and which is interrupted by a hetero atom selected from the group consisting of oxygen and sulfur or which has this hetero atom attached to one of its chain ends, the abovementioned alkyl, alkenyl, alkynyl and phenyl radicals optionally being substituted by one or more radicals selected from the group consisting of halogen, hydroxyl, mercapto, amino, cyano, nitro, formyl, $(C_1-C_4)$-alkylamino, $(C_1-C_4)$-dialkylamino, $(C_1-C_4)$-alkoxycarbonyl, $(C_1-C_4)$-alkylcarbonyl, $(C_1-C_4)$-alkoxycarbonyloxy, $(C_1-C_4)$-alkyl, halo-$(C_1-C_4)$-alkyl, $(C_1-C_4)$-alkylthio, halo-$(C_1-C_4)$-alkylthio, $(C_1-C_4)$-alkoxy, halo-$(C_1-C_4)$-alkoxy;

Het is heterocydyl or heteroaryl containing, as ring atom, at least one nitrogen atom and optionally additionally one, two or three hetero atoms selected from the group consisting of nitrogen, oxygen and sulfur, $R^1$ and $R^2$ independently of one another are hydrogen, mercapto, nitro, halogen, cyano, thiocyanato, $(C_1-C_6)$-alkyl, $(C_1-C_6)$-alkoxy-$(C_1-C_6)$-alkyl, halo-$(C_1-C_6)$-alkyl, $(C_2-C_6)$-alkenyl, $(C_2-C_6)$-alkynyl, $OS(O)_nR^{10}$, $(C_1-C_6)$-alkyl-A, $(C_2-C_6)$-alkenyl-A, $(C_2-C_6)$-alkynyl-A, $(C_1-C_6)$-alkoxy-$(C_1-C_6)$-alkyl-A, or are $(C_2-C_6)$-alkenyloxy-$(C_1-C_6)$-alkyl-$(A)_p$, $(C_2-C_6)$-alkynyloxy-$(C_1-C_6)$-alkyl-$(A)_p$, $(C_3-C_9)$-cycloalkyl-$(A)_p$, $(C_3-C_9)$-cycloalkenyl-$(A)_p$, $(C_1-C_6)$-alkyl-$(C_3-C_9)$-cycloalkyl-$(A)_p$, $(C_1-C_6)$-alkyl-$(C_3-C_9)$-cycloalkyl-$(C_1-C_6)$-alkyl-$(A)_p$, $(C_1-C_6)$-alkyl-$(C_3-C_9)$-cycloalkenyl-$(A)_p$, $(C_1-C_6)$-alkyl-$(C_3-C_9)$-cycloalkenyl-$(C_1-C_6)$-alkyl-$(A)_p$, $(C_2-C_6)$-alkenyl-$(C_3-C_9)$-cycloalkyl-$(A)_p$, $(C_2-C_6)$-alkenyl-$(C_3-C_9)$-cycloalkyl-$(C_1-C_6)$-alkyl-$(A)_p$, $(C_2-C_6)$-alkenyl-$(C_3-C_9)$-cycloalkenyl-$(A)_p$, $(C_2-C_6)$-alkenyl-$(C_3-C_9)$-cycloalkenyl-$(C_1-C_6)$-alkyl-$(A)_p$, $(C_2-C_6)$-alkynyl-$(C_3-C_9)$-cycloalkyl-$(A)_p$, $(C_2-C_6)$-alkynyl-$(C_3-C_9)$-cycloalkyl-$(C_1-C_6)$-alkyl-$(A)_p$, $(C_2-C_6)$-alkynyl-$(C_3-C_9)$-cycloalkyenyl-$(A)_p$, $(C_2-C_6)$-alkynyl-$(C_3-C_6)$-cycloalkenyl-$(C_1-C_6)$-alkyl-$(A)_p$, $OR^{10}$, $OCOR^{10}$, $S(O)_nR^{10}$, $SO_2N(R^{10})_2$, $NR^{10}SO_2R^{10}$ or $NR^{10}COR^{10}$, each of which is substituted by m radicals selected from the group consisting of cyano and nitro and w radicals selected from the halogen group;

$R^3$ is hydrogen, hydroxyl, halogen, mercapto, amino, cyano, nitro, formyl, or is $(C_1-C_4)$-alkylamino, $(C_1-C_4)$-dialkylamino, $(C_1-C_4)$-alkoxycarbonyl, $(C_1-C_4)$-alkylcarbonyl, $(C_1-C_4)$-alkylcarbonyloxy, $(C_1-C_4)$-alkyl, halo-$(C_1-C_4)$-alkyl, $(C_1-C_4)$-alkylthio, halo-$(C_1-C_4)$-alkylthio, $(C_1-C_4)$-alkoxy or halo-$(C_1-C_4)$-alkoxy, each of which is substituted by m radicals selected from the group consisting of cyano, nitro, formyl, $(C_1-C_4)$-alkylamino, $(C_1-C_4)$-dialkylamino, $(C_1-C_4)$-alkoxycarbonyl, $(C_1-C_4)$-alkylcarbonyl, $(C_1-C_4)$-alkylcarbonyloxy, $(C_1-C_4)$-alkyl, $(C_2-C_4)$-alkenyl, $(C_2-C_4)$-alkynyl, halo-$(C_1-C_4)$-alkyl, $(C_2-C_4)$-haloalkenyl, $(C_2-C_4)$-haloalkynyl, $(C_1-C_4)$-alkylthio, halo-$(C_1-C_4)$-alkylthio, $(C_1-C_4)$-alkoxy and halo-$(C_1-C_4)$-alkoxy;

$R^{3a}$ is hydrogen, $(C_1-C_6)$-alkyl, $(C_2-C_6)$-alkenyl, $(C_2-C_6)$-alkynyl, phenyl, phenyl-$(C_1-C_6)$-alkyl, it being possible for the five last-mentioned radicals to be substituted in their nonaromatic moiety by w radicals selected from the group consisting of hydroxy, halogen, mercapto, amino, cyano, nitro, formyl, $(C_1-C_4)$-alkylamino, $(C_1-C_4)$-dialkylamino, $(C_1-C_4)$-alkoxycarbonyl, $(C_1-C_4)$-alkylcarbonyl, halo-$(C_1-C_4)$-alkyl, $(C_1-C_4)$-alkylthio, halo-$(C_1-C_4)$-alkylthio, $(C_1-C_4)$-alkoxy and halo$(C_1-C_4)$-alkoxy;

$R^4$ is straight-chain or branched $[C(R^{11})_2]_m$-$(A)_p$-$[C(R^{11})_2]_m$-$R^{12}$;

A is oxygen or sulfur, $R^5$ is $OR^{16}$, $(C_1-C_6)$-alkylthio, halo-$(C_1-C_6)$-alkylthio, $(C_2-C_6)$-alkenylthio, halo-$(C_2-C_6)$-alkenylthio, $(C_2-C_6)$-alkynylthio, halo-$(C_2-C_6)$-alkynylthio, $(C_1-C_6)$-alkylsulfinyl, halo-$(C_1-C_6)$-alkylsulfinyl, $(C_2-C_6)$-alkenylsulfinyl, halo-$(C_2C_6)$-alkenylsulfinyl, $(C_2-C_6)$-alkynylsulfinyl, halo-$(C_2-C_6)$-alkynylsulfinyl, $(C_1-C_6)$-alkylsulfonyl, halo-$(C_1-C_6)$-alkylsulfonyl, $(C_2-C_6)$-alkenylsulfonyl, halo-$(C_2-C_6)$-alkenylsulfonyl, $(C_2-C_6)$-alkynylsulfonyl, halo-$(C_2-C_6)$-alkynylsulfonyl, cyano, cyanato, thiocyanato or halogen;

$R^6$ is hydrogen, tetrahydropyran-3-yl, tetrahydropyran-4-yl, tetrahydrothiopyran-3-yl, or is $(C_1-C_6)$-alkyl, $(C_3-C_6)$-cycloalkyl, $(C_1-C_6)$-alkoxy, $(C_1-C_6)$-alkylcarbonyl, $(C_1-C_6)$-alkoxy-$(C_1-C_6)$-alkyl, ($C_1$–$C_6$)-alkoxycarbonyl, ($C_1$–$C_6$)-alkylthio or phenyl, each of which is substituted by w radicals selected from the group consisting of halogen, ($C_1$–$C_6$)-alkylthio and ($C_1$–$C_6$)-alkoxy, or two radicals $R^6$ bound to a joint carbon atom form a chain selected from the group consisting of $OCH_2CH_2O$, $OCH_2CH_2CH_2O$, $SCH_2CH_2S$ and $SCH_2CH_2CH_2S$ which is optionally substituted by one to four methyl groups;

$R^7$ is hydrogen, ($C_1$–$C_6$)-alkyl or ($C_1$–$C_6$)-haloalkyl;

$R^8$ is ($C_1$–$C_6$)-alkyl, halo-($C_1$–$C_6$)-alkyl, or is phenyl which is optionally substituted by one or more radicals selected from the group consisting of halogen, nitro, cyano, ($C_1$–$C_4$)-alkyl, halo-($C_1$–$C_4$)-alkyl, ($C_1$–$C_4$)-alkoxy and halo-($C_1$–$C_4$)-alkoxy;

$R^9$ is hydrogen, ($C_1$–$C_6$)-alkyl, halo-($C_1$–$C_6$)-alkyl, ($C_1$–$C_6$)-alkylcarbonyl, halo-($C_1$–$C_6$)-alkylcarbonyl, ($C_1$–$C_6$)-alkoxycarbonyl, ($C_1$–$C_6$)-alkylsufonyl, halo-($C_1$–$C_6$)-alkylsulfonyl, or is benzoyl, benzoylmethyl, phenoxycarbonyl or phenylsulfonyl, each of which is optionally substituted by one or more radicals selected from the group consisting of halogen, nitro, cyano, ($C_1$–$C_4$)-alkyl, halo-($C_1$–$C_4$)-alkyl, ($C_1$–$C_4$)-alkoxy and halo-($C_1$–$C_4$)-alkoxy;

$R^{10}$ is hydrogen, or is ($C_1$–$C_6$)-alkyl, halo-($C_1$–$C_6$)-alkyl, ($C_1$–$C_6$)-alkoxy, ($C_2$–$C_6$)-alkenyl, ($C_2$–$C_6$)-alkynyl, phenyl or phenyl-($C_1$–$C_6$)-alkyl, each of which is substituted by w radicals selected from the group consisting of hydroxyl, halogen, mercapto, amino, cyano, ($C_1$–$C_4$)-alkyl, ($C_1$–$C_4$)-alkoxy, ($C_1$–$C_4$)-alkylthio, di-($C_1$–$C_4$)-alkylamino, ($C_1$–$C_4$)-alkoxyimino, ($C_1$–$C_4$)-alkoxythiocarbonyl, ($C_1$–$C_4$)-alkylcarbonyl-($C_1$–$C_4$)-alkylamino, ($C_1$–$C_4$)-alkoxycarbonyl, ($C_1$–$C_4$)-alkylthiocarbonyl, di-($C_1$–$C_4$)-alkylaminocarbonyl, ($C_1$–$C_4$)-alkyliminooxy, ($C_1$–$C_4$)-alkoxyamino, ($C_1$–$C_4$)-alkylcarbonyl, ($C_1$–$C_4$)-alkoxy-($C_2$–$C_6$)-alkoxycarbonyl, ($C_1$–$C_4$)-alkylsulfonyl, heterocyclyl, heterocyclyloxy, phenyl, benzyl, heteroaryl, phenoxy, benzyloxy and heteroaryloxy;

$R^{11}$ is hydrogen, ($C_1$–$C_4$)-alkyl or halogen;

$R^{12}$ is cycloalkyl, cycloalkenyl, aryl, a heterocyclyl or heteroaryl containing one to four hetero atoms selected from the group consisting of oxygen, nitrogen, and sulfur, each of which is substituted by w radicals selected from the group consisting of halogen, cyano, formyl, nitro, ($C_1$–$C_4$)-alkyl, halo-($C_1$–$C_4$)-alkyl, ($C_1$–$C_4$)-alkoxy, halo-($C_1$–$C_4$)-alkoxy, ($C_1$–$C_4$)-alkylthio, halo-($C_1$–$C_4$)-alkylthio and $R^{13}$, or is a radical of the formula (Va) to (Vt):

137

-continued

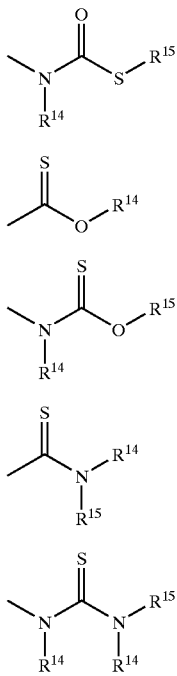

(Vp)

(Vq)

(Vr)

(Vs)

(Vt)

$R^{13}$ is [($C_1$–$C_4$)-alkylene-O—($C_1$–$C_4$)-alkylene]$_o$-O—($C_1$–$C_4$)-alkyl, or is ($C_1$–$C_4$)-alkyl, ($C_2$–$C_4$)-alkenyl or ($C_2$–$C_4$)-alkynyl, each of which is substituted by w halogen atoms;

$R^{14}$ is hydrogen, ($C_1$–$C_4$)-alkyl, ($C_1$–$C_4$)-alkoxy, ($C_2$–$C_4$)-alkenyl, ($C_2$–$C_4$)-alkynyl, ($C_3$–$C_9$)-cycloalkyl, aryl, aryl-($C_1$–$C_6$)-alkyl, heteroaryl, heterocydyl, halo-($C_1$–$C_4$)-alkyl;

$R^{15}$ is hydrogen, tetrahydrofuran-2-yl, ($C_1$–$C_4$)-alkyl, ($C_2$–$C_4$)-alkenyl, ($C_2$–$C_4$)-alkynyl, ($C_3$–$C_9$)-cycloalkyl, aryl, aryl-($C_1$–$C_6$)-alkyl, heteroaryl, heterocyclyl, halo-($C_1$–$C_4$)-alkyl, or, if $R^{14}$ and $R^{15}$ are bound to one atom or to two directly adjacent atoms, they form together with the atoms binding them a saturated or partially or fully unsaturated five- to six-membered ring which optionally additionally contains a hetero atom selected from the group consisting of oxygen, nitrogen and sulfur;

$R^{16}$ is hydrogen, ($C_1$–$C_6$)-alkyl, halo-($C_1$–$C_6$)-alkyl, ($C_1$–$C_6$)-alkoxy($C_1$–$C_6$)-alkyl, formyl, ($C_1$–$C_6$)-alkylcarbonyl, ($C_1$–$C_6$)-alkoxycarbonyl, ($C_1$–$C_6$)-alkylaminocarbonyl, di-($C_1$–$C_6$)-alkylaminocarbonyl, ($C_1$–$C_6$)-alkylsulfonyl, halo-($C_1$–$C_6$)-alkylsulfonyl, benzoyl or phenylsulfonyl, the two last-mentioned groups being substituted by w identical or different radicals selected from the group consisting of ($C_1$–$C_6$)-alkyl, halo-($C_1$–$C_6$)-alkyl, ($C_1$–$C_6$)-alkoxy, halo-($C_1$–$C_6$)-alkoxy, halogen, cyano and nitro;

Y is a divalent unit selected from the group consisting of O, S, N—H, N—($C_1$–$C_6$)-alkyl, CHR$^6$ and C(R$^6$)$_2$;

Z is a direct bond or a divalent unit selected from the group consisting of O, S, SO, SO$_2$, N—H, N—($C_1$–$C_6$)-alkyl, CHR$^7$ or C(R$^7$)$_2$;

k in the event that Het is a bicyclic heteroaromatic ring or heterocycle, is 0, 1 or 2, and in the event that Het is a monocyclic heteroaromatic ring or heterocycle, 1 or 2;

138 m is 0, 1 or 2;

n is 0, 1 or 2;

o is 1, 2, 3 or 4;

p is 0 or 1;

v is 1 or 2;

w is 0, 1, 2, 3 or 4, or an agriculturally useful salt thereof.

2. A benzoyl compound of the formula (I) as claimed in claim 1, in which $R^1$ is nitro, halogen, cyano, ($C_1$–$C_6$)-alkyl, halo-($C_1$–$C_6$)-alkyl, ($C_2$–$C_6$)-alkenyl, ($C_2$–$C_6$)-alkynyl, OR$^{10}$ or S(O)$_n$R$^{10}$;

$R^2$ is hydrogen, nitro, halogen, cyano, ($C_1$–$C_6$)-alkyl, halo-($C_1$–$C_6$)-alkyl, ($C_2$–$C_6$)-alkenyl, ($C_2$–$C_6$)-alkynyl, OR$^{10}$ or S(O)$_n$R$^{10}$ and $R^{12}$ is ($C_3$–$C_6$)-cycloalkyl, substituted ($C_3$–$C_6$)-cycloalkenyl, phenyl, or a 5- to 6-membered heterocyclyl or heteroaryl—which contains one to four hetero atoms selected from the group consisting of oxygen, nitrogen and sulfur—each of which is substituted by w radicals selected from the group consisting of halogen, cyano, formyl, nitro, ($C_1$–$C_4$)-alkyl, halo-($C_1$–$C_4$)-alkyl, ($C_1$–$C_4$)-alkoxy, halo-($C_1$–$C_4$)-alkoxy, ($C_1$–$C_4$)-alkylthio, halo-($C_1$–$C_4$)-alkylthio and R$^{13}$, or is a radical of the formula (Va) to (Vh).

3. A benzoyl compound of the formula (I) as claimed in claim 1, in which X is a ($C_1$–$C_3$)-alkylene, ($C_2$–$C_4$)-alkenylene or ($C_2$–$C_4$)-alkynylene chain which is interrupted by an oxygen atom or which has an oxygen atom attached to one of the chain ends, and R$^1$ is in the 2-position and R$^2$ in the 4-position of the benzoyl ring.

4. A benzoyl compound of the formula (I) as claimed in claim 1, in which $R^1$ is chlorine, bromine, iodine, nitro or methyl;

$R^2$ is chlorine, bromine, trifluoromethyl or ($C_1$–$C_4$)-alkylsulfonyl;

$R^3$ is hydrogen and

X is a chain selected from the group consisting of OCH$_2$, CH$_2$O, OCH$_2$CH$_2$, CH$_2$OCH$_2$, CH$_2$OCH$_2$CH=CH, CH=CHCH$_2$O and C≡C—CH$_2$O.

5. A benzoyl compound of the formula (I) as claimed in claim 1, in which k is 1;

Het is a radical selected from the group consisting of isoxazolidinyl, isoxazolinyl and isoxazolyl, and A is oxygen.

6. A benzoyl compound of the formula (I) as claimed in claim 1, in which

Het is a radical selected from the group consisting of 1,2,4-oxadiazolyl, 1,3,4-oxadiazolyl, oxazolyl and thiazolyl, and k is 1.

7. A benzoyl compound of the formula (I) as claimed in claim 1, in which

Het is a radical selected from the group consisting of quinolinyl, 5,6,7,8-tetrahydroquinolinyl, benzoxazolyl and benzothiazolyl, and k is 0.

8. A benzoyl compound as claimed in claim 1, in which Q is the radical of the formula (Q1).

9. A benzoyl compound as claimed in claim 8, in which

Q1 is a cyclohexane-1,3-dione ring of the formula (Q1a) which is linked in the 2-position;

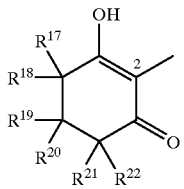

(Q1a)

$R^{17}$, $R^{18}$, $R^{20}$ and $R^{22}$ independently of one another are hydrogen or ($C_1$–$C_4$)-alkyl;

$R^{19}$ is hydrogen, tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, which is optionally substituted by one to three ($C_1$–$C_4$)-alkyl radicals, or is ($C_1$–$C_4$)-alkyl or ($C_1$–$C_3$)-cycloalkyl, each of which is substituted by w radicals selected from the group consisting of halogen, ($C_1$–$C_4$)-alkylthio and ($C_1$–$C_4$)-alkoxy;

$R^{21}$ is hydrogen, ($C_1$–$C_4$)-alkyl or ($C_1$–$C_6$)-alkoxycarbonyl, or $R^{19}$ and $R^{22}$ form a bond or a three- to six-membered ring, or $R^{19}$ and $R^{20}$ together with the carbon atom binding them form a carbonyl group.

10. A process for the preparation of benzoyl compounds of the formula (I) as claimed in claim 1, in which Q is Q1 and $R^5$ is hydroxyl, in which a compound of the formula (Q1b) is reacted in the presence of dehydrating agents with base catalysis and in the presence of a cyanide source or directly with base catalysis with a benzoic acid derivative of the formula (IVa) in which R is a nucleophilically exchangeable leaving group, an alkoxy group or hydroxyl.

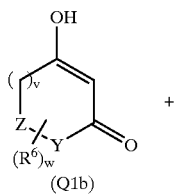

(Q1b)

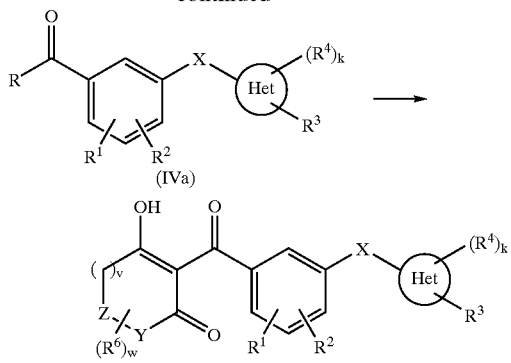

(IVa)

11. A benzoic acid derivative of the formula (IVa) as claimed in claim 10 for the preparation of compounds of the formula (I) as claimed in claim 1.

12. A herbicidal composition, comprising a herbicidally active amount of at least one compound of the formula (I) as claimed in claim 1 and at least one formulation auxiliary.

13. A method of controlling undesired plants, which comprises applying a herbicidal composition as claimed in claim 12 to said undesired plants or to a site where said undesired plants reside.

14. A method of controlling undesired plants, which comprises applying an effective amount of at least one compound of the formula (I) as claimed in claim 1 or of a herbicidal composition as claimed in claim 12 to the plants or to the site sustaining undesired plant growth.

15. A method of controlling undesired plants, which comprises of applying at least one compound of the formula (I) as claimed in claim 1 to said undesired plants or to a site where said undesired plants reside.

16. The method of claim 15, wherein the undesired plants are in crops of useful plants.

17. The method of claim 16, wherein the crop plants are transgenic useful plants.

* * * * *